US010045761B2

(12) United States Patent
Weber

(10) Patent No.: US 10,045,761 B2
(45) Date of Patent: Aug. 14, 2018

(54) SYSTEMS, APPARATUS AND METHODS FOR TISSUE DISSECTION

(71) Applicant: Paul Joseph Weber, Queenstown (NZ)

(72) Inventor: Paul Joseph Weber, Queenstown (NZ)

(73) Assignee: TDM Surgitech, Inc., Palm Harbor, FL (US)

( * ) Notice: Subject to any disclaimer, the term of this patent is extended or adjusted under 35 U.S.C. 154(b) by 1313 days.

(21) Appl. No.: 13/767,876

(22) Filed: Feb. 14, 2013

(65) Prior Publication Data

US 2014/0187870 A1 Jul. 3, 2014

Related U.S. Application Data

(63) Continuation-in-part of application No. 13/759,969, filed on Feb. 5, 2013.

(60) Provisional application No. 61/760,628, filed on Feb. 4, 2013, provisional application No. 61/751,239, filed
(Continued)

(51) Int. Cl.
*A61B 5/1455* (2006.01)
*A61B 10/02* (2006.01)
*A61B 18/14* (2006.01)
*A61B 18/12* (2006.01)
*A61B 18/18* (2006.01)
*A61B 18/00* (2006.01)

(52) U.S. Cl.
CPC ...... *A61B 10/0266* (2013.01); *A61B 5/14552* (2013.01); *A61B 18/12* (2013.01); *A61B 18/14* (2013.01); *A61B 18/00* (2013.01); *A61B 18/1815* (2013.01)

(58) Field of Classification Search
None
See application file for complete search history.

(56) References Cited

U.S. PATENT DOCUMENTS

| 4,221,997 A | 9/1980 | Flemming |
| 4,259,876 A | 4/1981 | Belyanin et al. |
| 4,462,748 A | 7/1984 | Inaba et al. |

(Continued)

FOREIGN PATENT DOCUMENTS

| EP | 1276423 B1 | 1/2003 |
| EP | 1695662 A1 | 8/2006 |
| EP | 2526427 A2 | 11/2012 |

OTHER PUBLICATIONS

Miniaturized Ultrasound Arrays for Interstitial Ablation and Imaging (Makin, Mast, Faidi, et al.; Ultrasound Med Biol 2005;31(11)1539-50.).

(Continued)

*Primary Examiner* — Eric Winakur
*Assistant Examiner* — Marjan Fardanesh
(74) *Attorney, Agent, or Firm* — Thayne and Davis LLC; Matthew D. Thayne

(57) ABSTRACT

Methods, apparatus and systems for tissue dissection and testing are disclosed herein. A method for tissue dissection and testing may comprise inserting a tissue dissecting wand (TD) through an incision in a patient's body. The TD may comprise a tip having a plurality of protrusions with lysing segments positioned between the protrusions to dissect and/or modify tissue. The TD may also comprise a sensor dock positioned on top of the TD that is configured to allow tissue and/or body fluid contact to a sensor. After separating tissue using the lysing segment(s) to access a target region, the sensor may be activated and moved around within the target region to assess tissues.

50 Claims, 23 Drawing Sheets

Related U.S. Application Data on Jan. 10, 2013, provisional application No. 61/748,037, filed on Dec. 31, 2012.

(56) References Cited

U.S. PATENT DOCUMENTS

| | | |
|---|---|---|
| 4,494,417 A | 1/1985 | Larson et al. |
| 4,582,057 A | 4/1986 | Auth et al. |
| 4,631,689 A | 12/1986 | Arimura et al. |
| 4,806,066 A | 2/1989 | Rhodes et al. |
| 4,862,890 A | 9/1989 | Stasz |
| 5,244,462 A | 9/1993 | Delahuerga |
| 5,395,363 A | 3/1995 | Billings et al. |
| 5,647,867 A | 7/1997 | Neuberger et al. |
| 5,693,043 A | 12/1997 | Kittrell et al. |
| 5,695,510 A | 12/1997 | Hood |
| 5,755,753 A | 5/1998 | Knowlton |
| 5,776,092 A | 7/1998 | Farin et al. |
| 5,791,231 A | 8/1998 | Cohn et al. |
| 5,827,267 A | 10/1998 | Savage et al. |
| 5,860,976 A | 1/1999 | Billings et al. |
| 5,871,524 A | 2/1999 | Knowlton |
| 5,873,855 A | 2/1999 | Eggers |
| 5,919,219 A | 7/1999 | Knowlton |
| 5,935,143 A | 8/1999 | Hood |
| 5,948,011 A | 9/1999 | Knowlton |
| 5,951,550 A | 9/1999 | Shirley et al. |
| 5,984,915 A | 11/1999 | Loeb et al. |
| 6,033,398 A | 3/2000 | Farley et al. |
| 6,135,999 A | 10/2000 | Fanton et al. |
| 6,176,854 B1 | 1/2001 | Cone |
| 6,203,540 B1 | 3/2001 | Weber |
| 6,241,753 B1 | 6/2001 | Knowlton |
| 6,277,116 B1 | 8/2001 | Utley et al. |
| 6,311,090 B1 | 10/2001 | Knowlton |
| 6,346,105 B1 | 2/2002 | Tu et al. |
| 6,391,023 B1 | 5/2002 | Weber et al. |
| 6,432,101 B1 | 8/2002 | Weber et al. |
| 6,440,121 B1 | 8/2002 | Weber et al. |
| 6,593,093 B1 | 7/2003 | Uhl |
| 6,699,186 B1 | 3/2004 | Wolinsky et al. |
| 6,974,450 B2 | 12/2005 | Weber et al. |
| 7,199,545 B2 | 4/2007 | Oleynikov et al. |
| 7,316,681 B2 | 1/2008 | Madhani et al. |
| 7,494,488 B2 | 2/2009 | Weber |
| 7,959,633 B2 | 6/2011 | Sartor et al. |
| 8,182,418 B2 | 5/2012 | Durant et al. |
| 8,224,485 B2 | 7/2012 | Unsworth |
| 2006/0223080 A1 | 10/2006 | Pollner et al. |
| 2007/0225550 A1 | 9/2007 | Gattani et al. |
| 2009/0186774 A1 | 7/2009 | Turner et al. |
| 2009/0281419 A1 | 11/2009 | Troesken et al. |
| 2010/0280409 A1 | 11/2010 | Mark |
| 2011/0144729 A1 | 6/2011 | Weber |
| 2012/0228155 A1 | 3/2012 | Clare et al. |

OTHER PUBLICATIONS

Design and Preliminary Results of an Ultrasound Applicator for Interstitial Thermal Coagulation (Lafon, Chapelon, Prat, et al.; Ultrasound Med Biol 1998;24(1):113-22.).

Optimizing the Shape of Ultrasound Transducers for Interstitial Thermal Ablation (Lafon, Theillere, et al.; Med Phys 2002;29(3):290-7.).

Rapid Skin Permeablization by the Simultaneous Application of Dual Frequency, High-Intensity Ultrasound (Schoelhammer, Polat, Mendenhall, Langer, et al; Journal of Controlled Release, 2012, 163(2):154-160.).

Interstitial Devices for Minimally Invasive Thermal Ablation by High Intensity Ultrasound (Lafon, Melodelima, Salomir, Chaelon; Int J. Hyperther 2007; 23(2):153-63.).

Theoretical Comparison of Two Interstitial Ultrasound Applicators Designed to Induce Cylindrical Zones of Tissue Ablation (Lafon, Chavrier, Prat, et al.; Med Biol Eng Comput 1999;37(3):298-303.)

Feasibility of Linear Arrays for Interstitial Ultrasound Thermal Therapy (Chopra, Bronskill, Foster; Med Phys 2000;27(6):1281-6.).

Development of an Interstitial Ultrasound Applicator for Endoscopic Procedures: Animal Experimentation (Lafon, Theillere, Prat, et al.; Ultrasound Med Biol 2000;26(4):669-75.).

Multisectored Interstitial Ultrasound Applicators for Dynamic Angular Control of Thermal Therapy (Kinsey, Diederich, Tyreus, et al.; Med Phys 2006;33(5):1352-63.).

Evaluation of Multielement catheter-cooled interstitial ultrasound applicators for high-temperature thermal therapy (Nau, Diederich, Burdette; Med Phys 2001;28(7):1525-34.).

Feasibility of Ultrasound Hyperthermia with Waveguide Interstitial Applicator (Jarosz; IEEE Trans Biomed Eng 1996;43(11):1106-15.).

Transurethral Ultrasound Array for Prostate Thermal Therapy: Initial Studies (Diederich, Burdette; IEEE Trans Ultrason Ferroelectr Freq Control 1996;43(6):1011-22.).

Scanometric DNA Array Detection with Nanoparticle Probes (Taton, Mirkin, Lestinger; Science, Sep. 8, 2000, vol. 289, No. 5485, pp. 1757-1760.).

Detection of Methicillin-Resistant *Staphylococcus aureus* (MRSA) using the NanoLantern Biosensor (Strohsahl, Miller, Krauss; Proc. of SPIE, vol. 7167OS pp. 1-12.).

Ultrasensitive and Selective Multiplexing Detection of Cancer Markers Using Nanowire Nanosensors (Ciu, Wang, Huynh, Lieber; Harvard University, pp. 1-21.).

Field Effect Transistor Nanosensor for Breast Cancer Diagnostics (Mohanty, Chen, Wang, Hong, Rosenberg, Weaver, Erramilli; Boston University, pp. 1-25.).

EPO Office Action, Application No. 14752036.5, 6 pgs.

Supplementary European Search Report, EP14752036, 3 pgs.

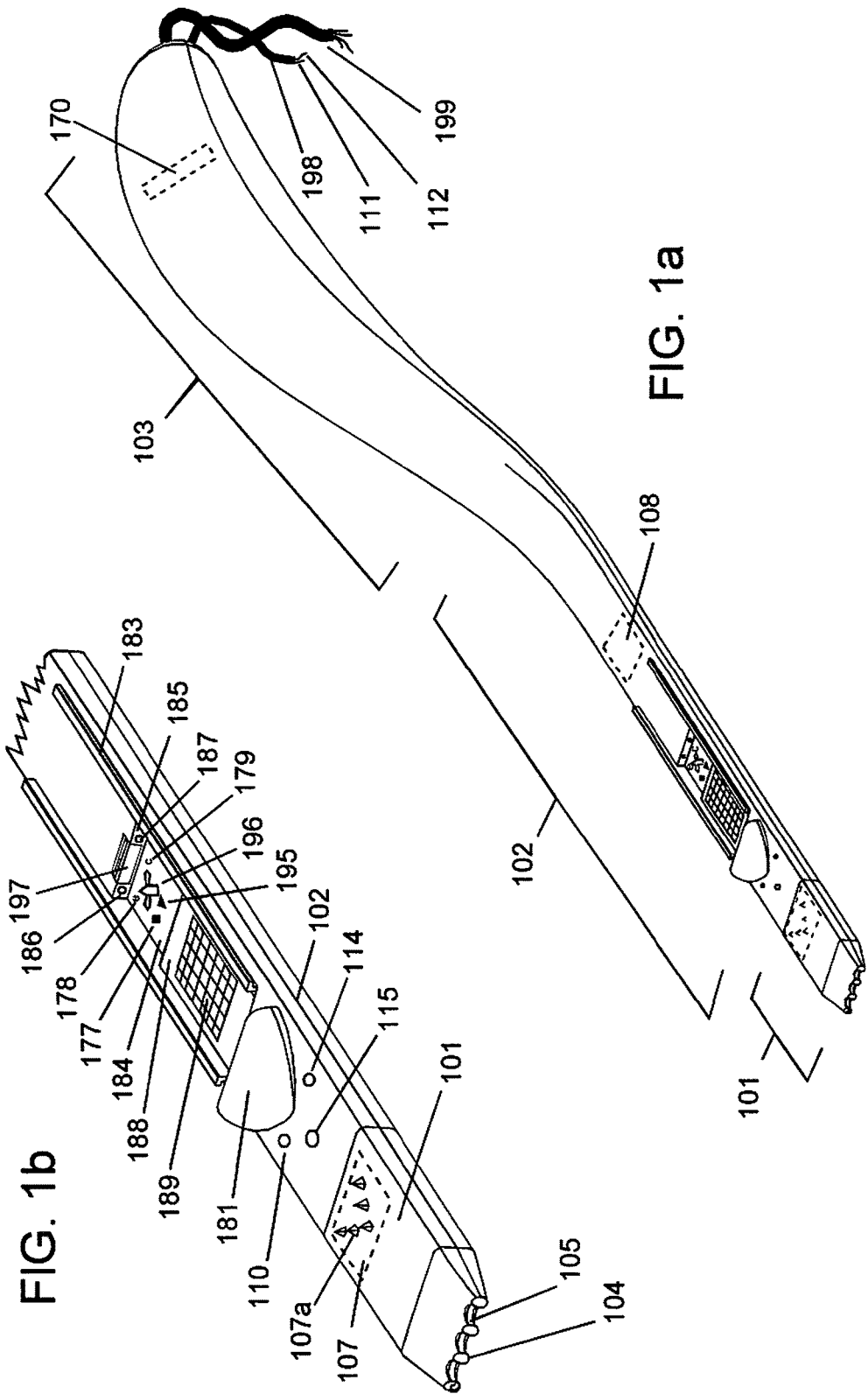

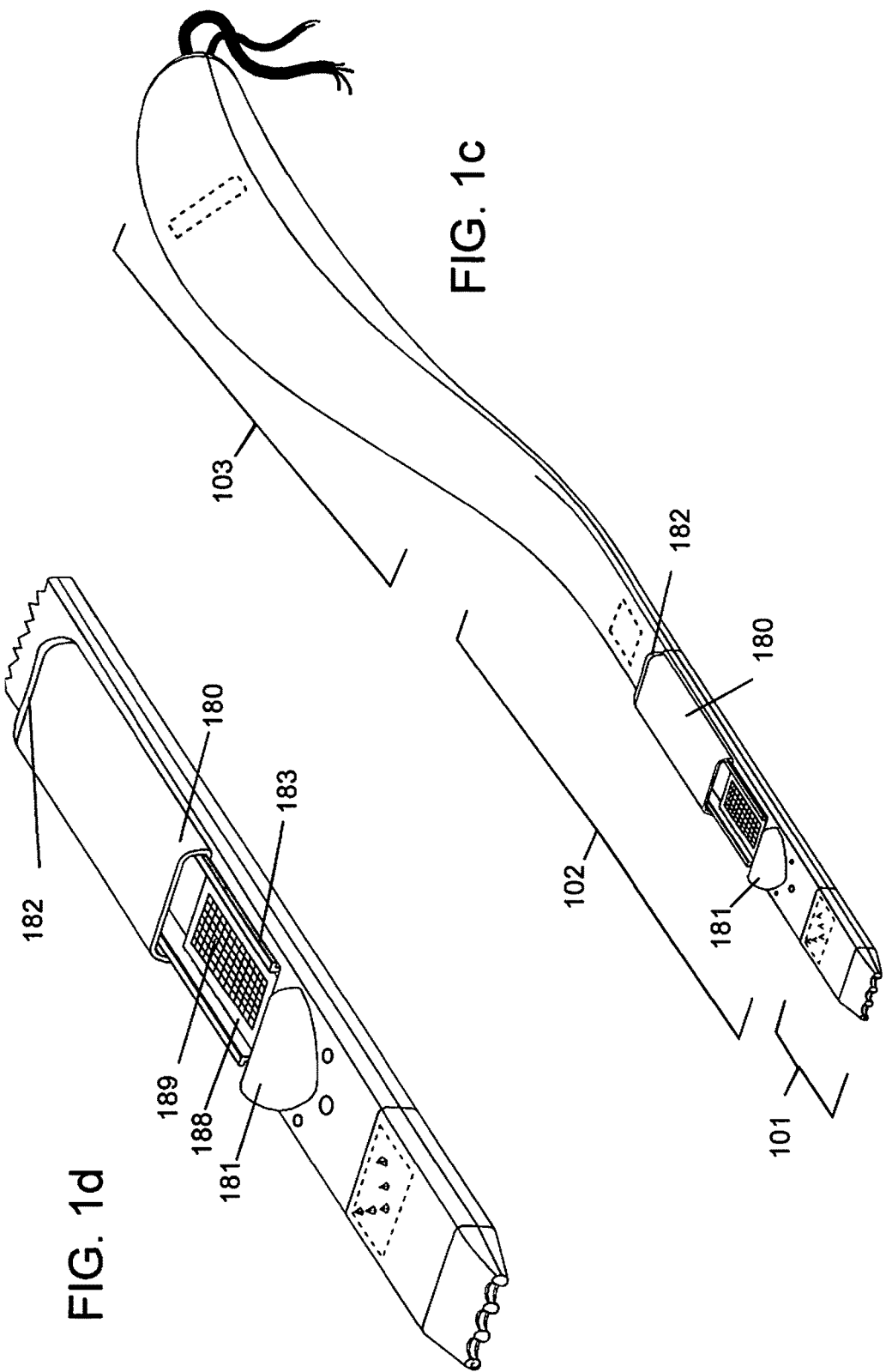

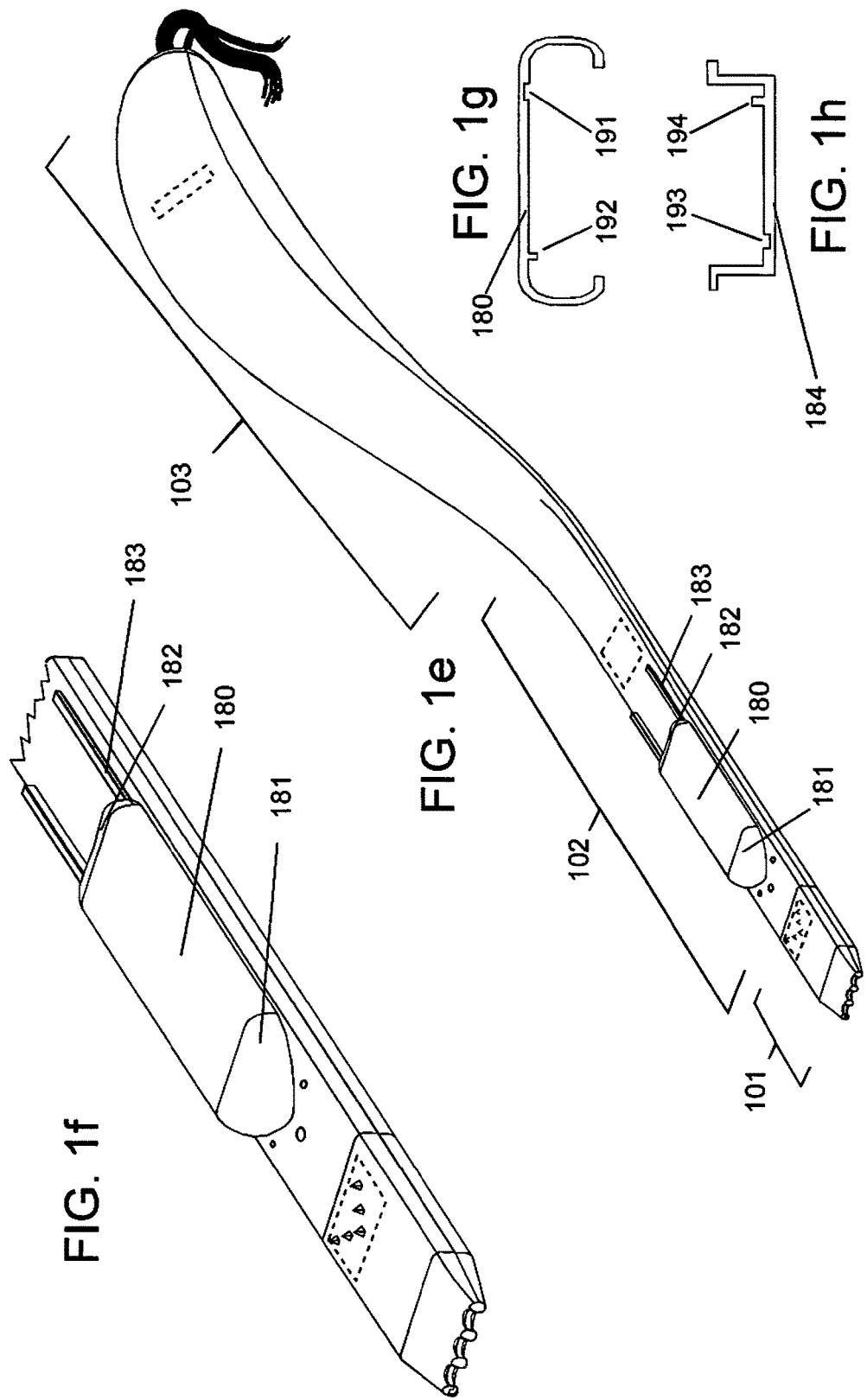

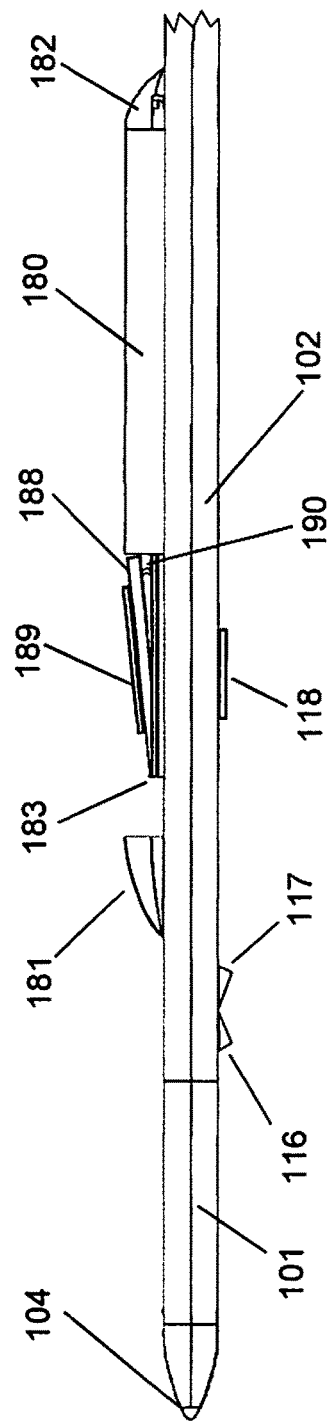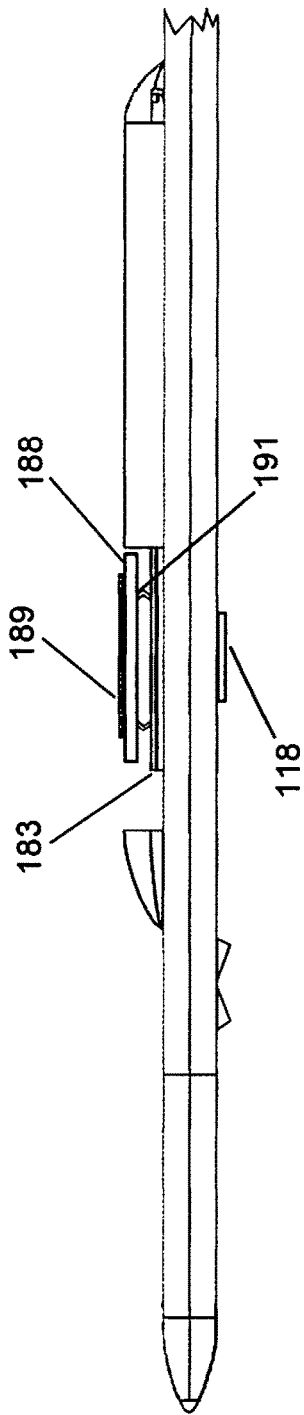

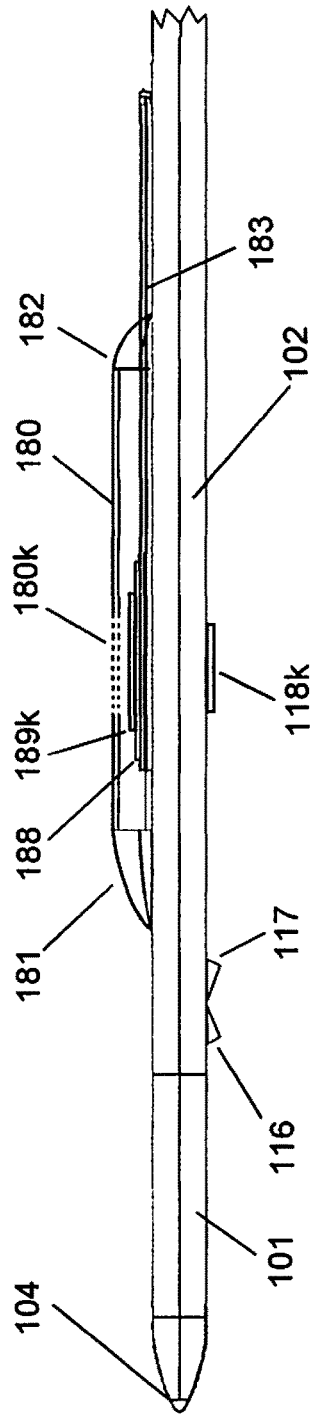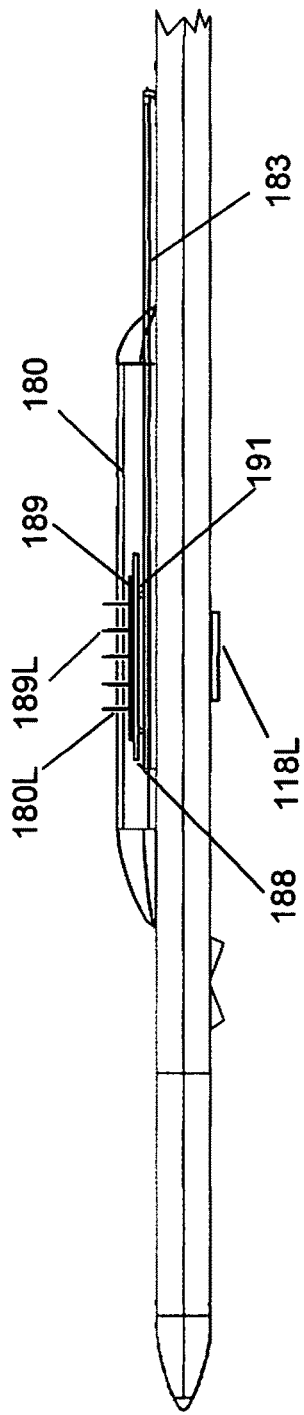

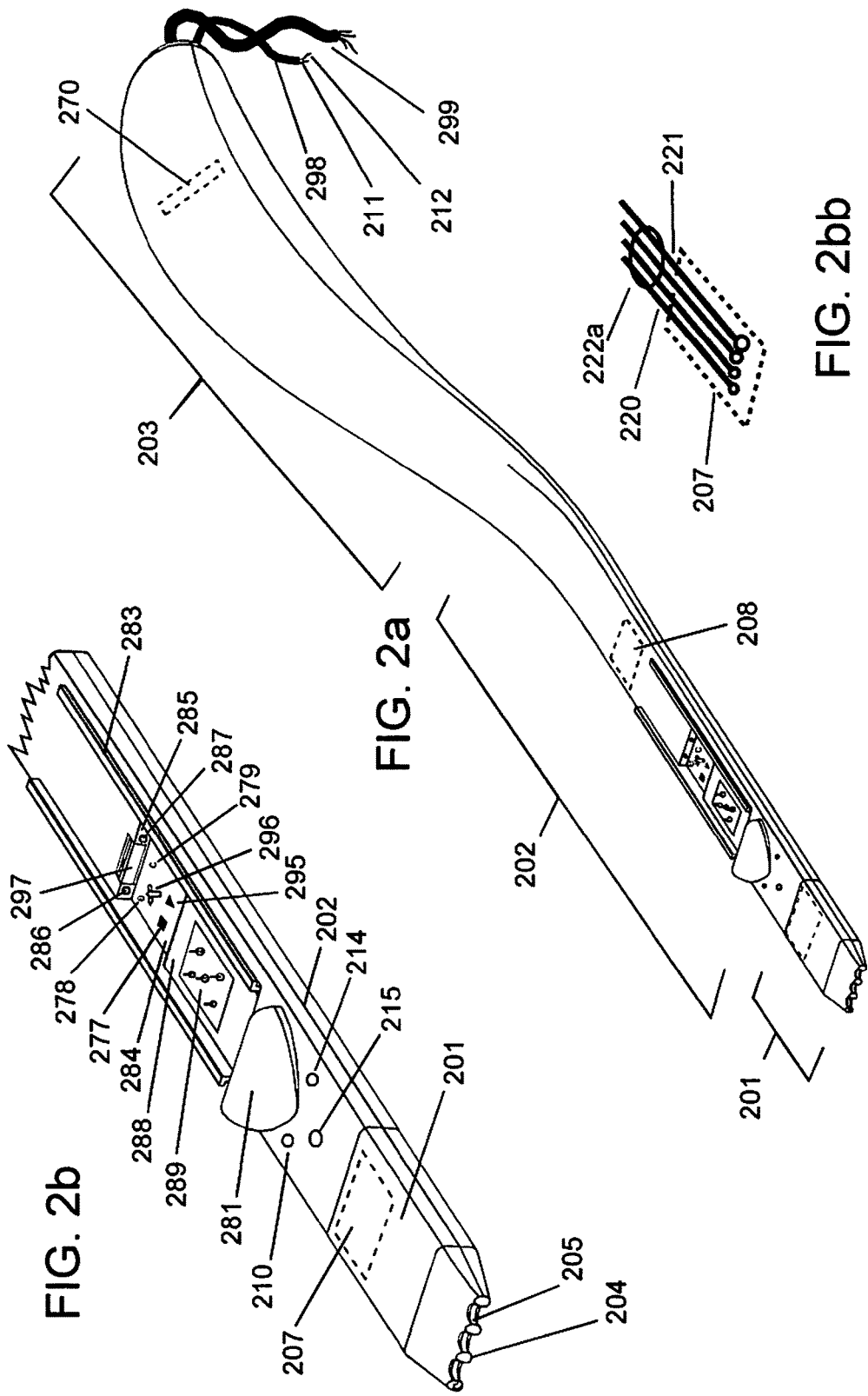

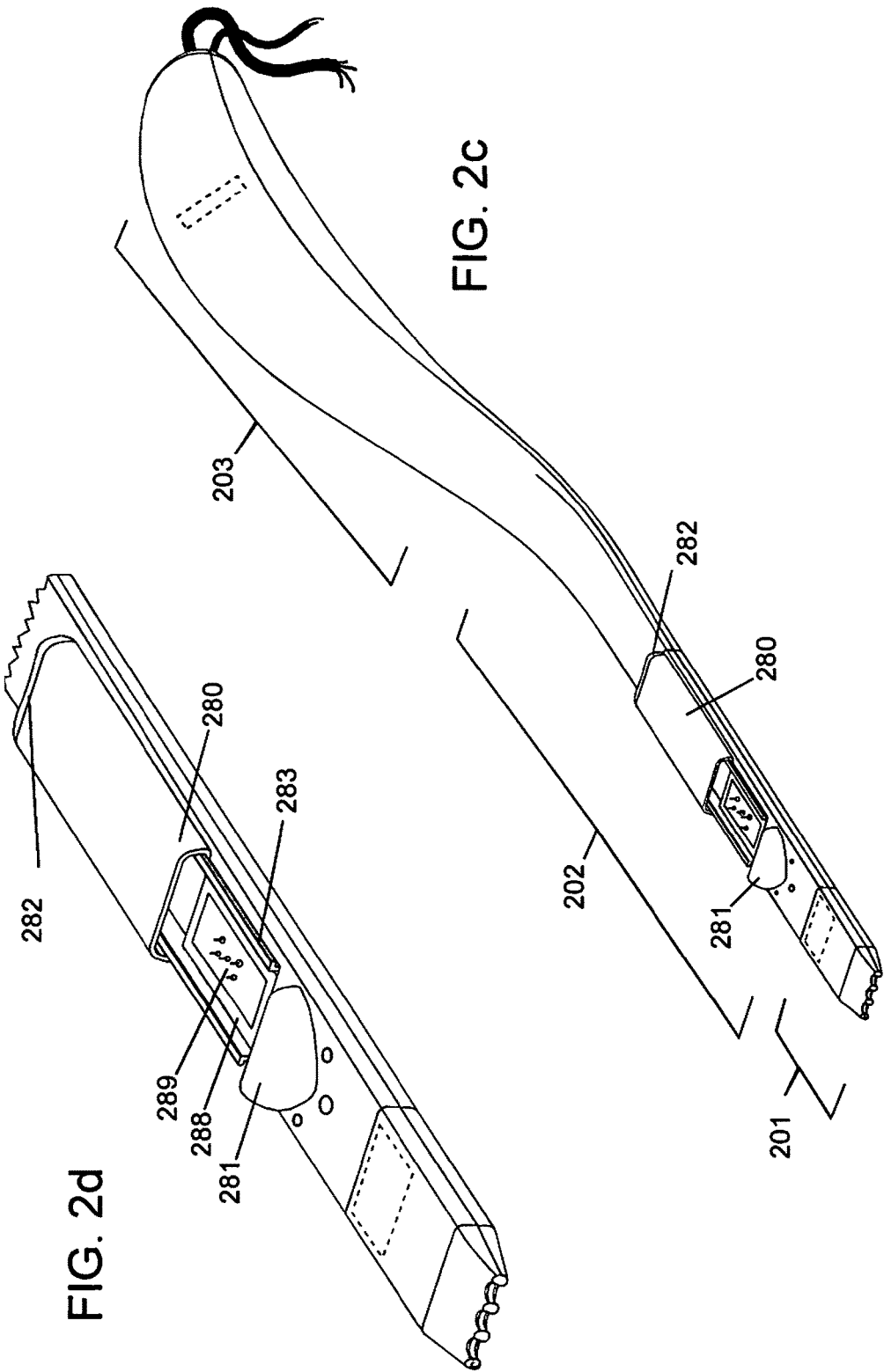

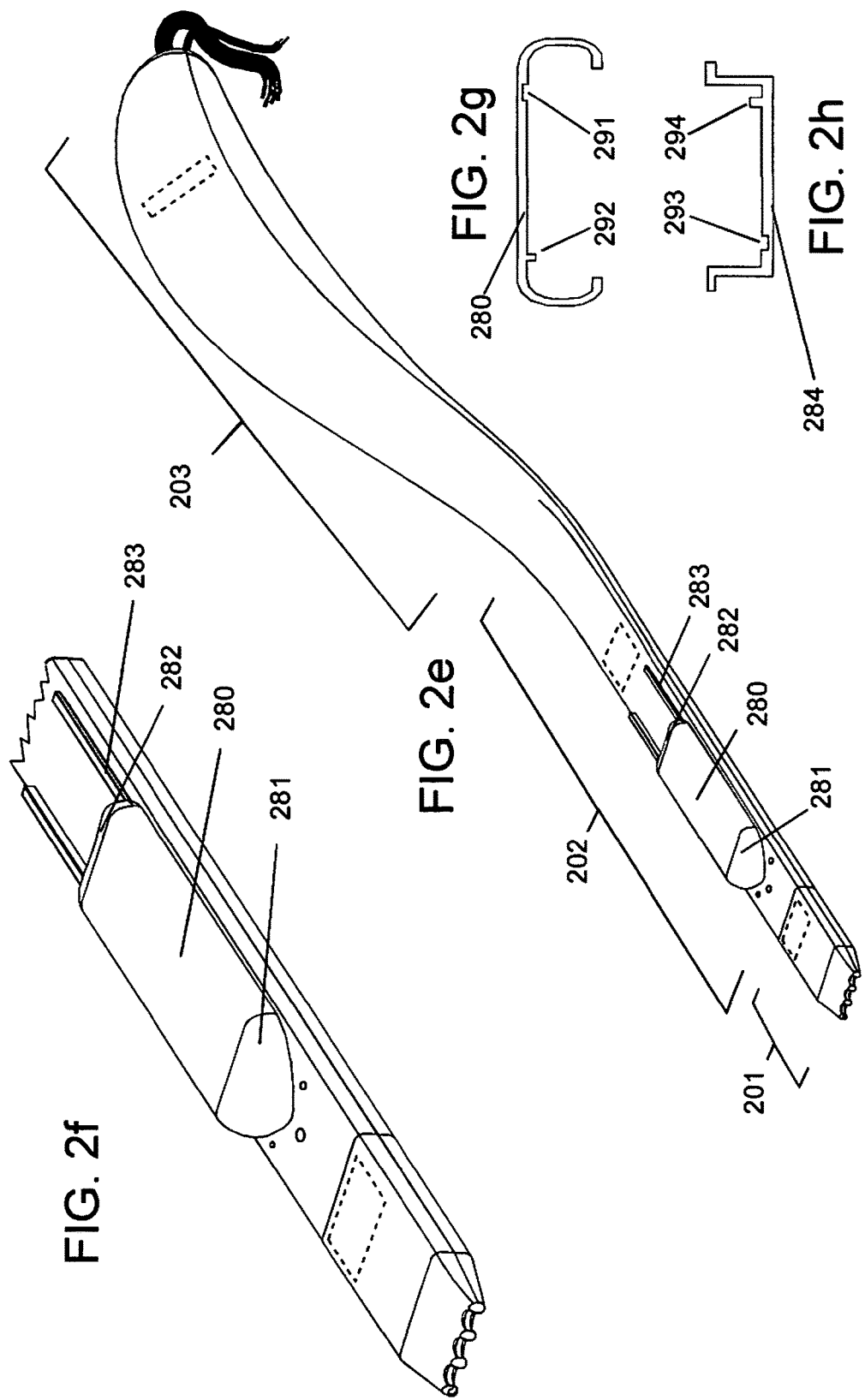

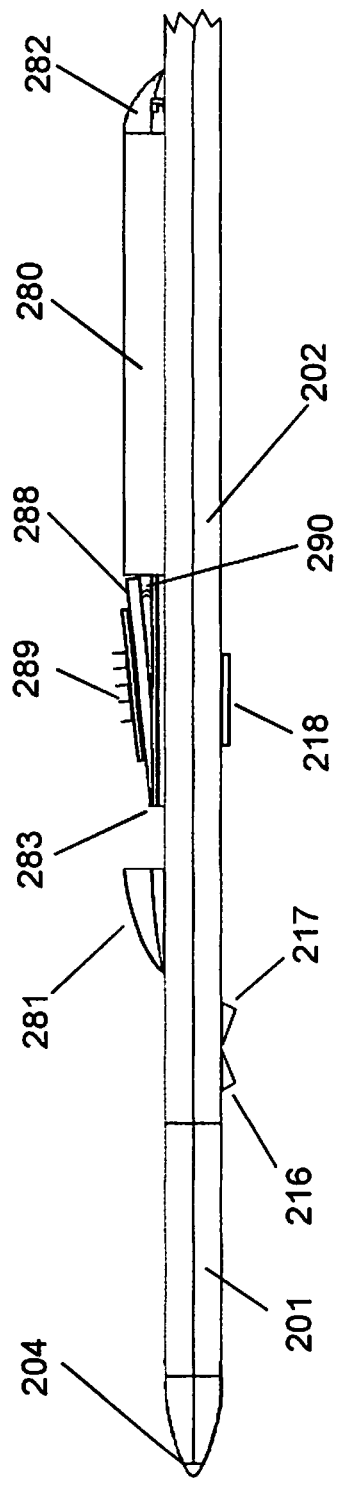

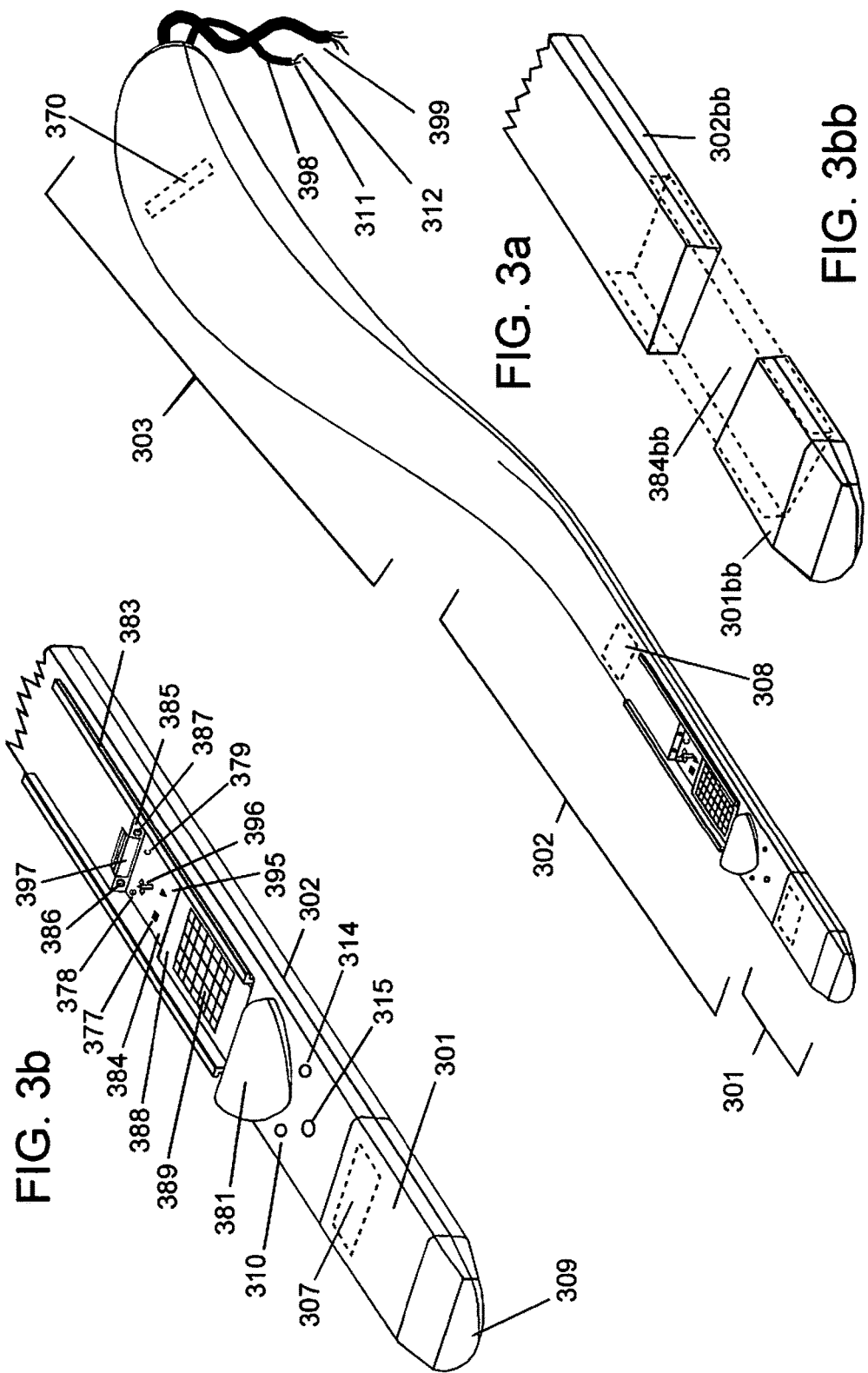

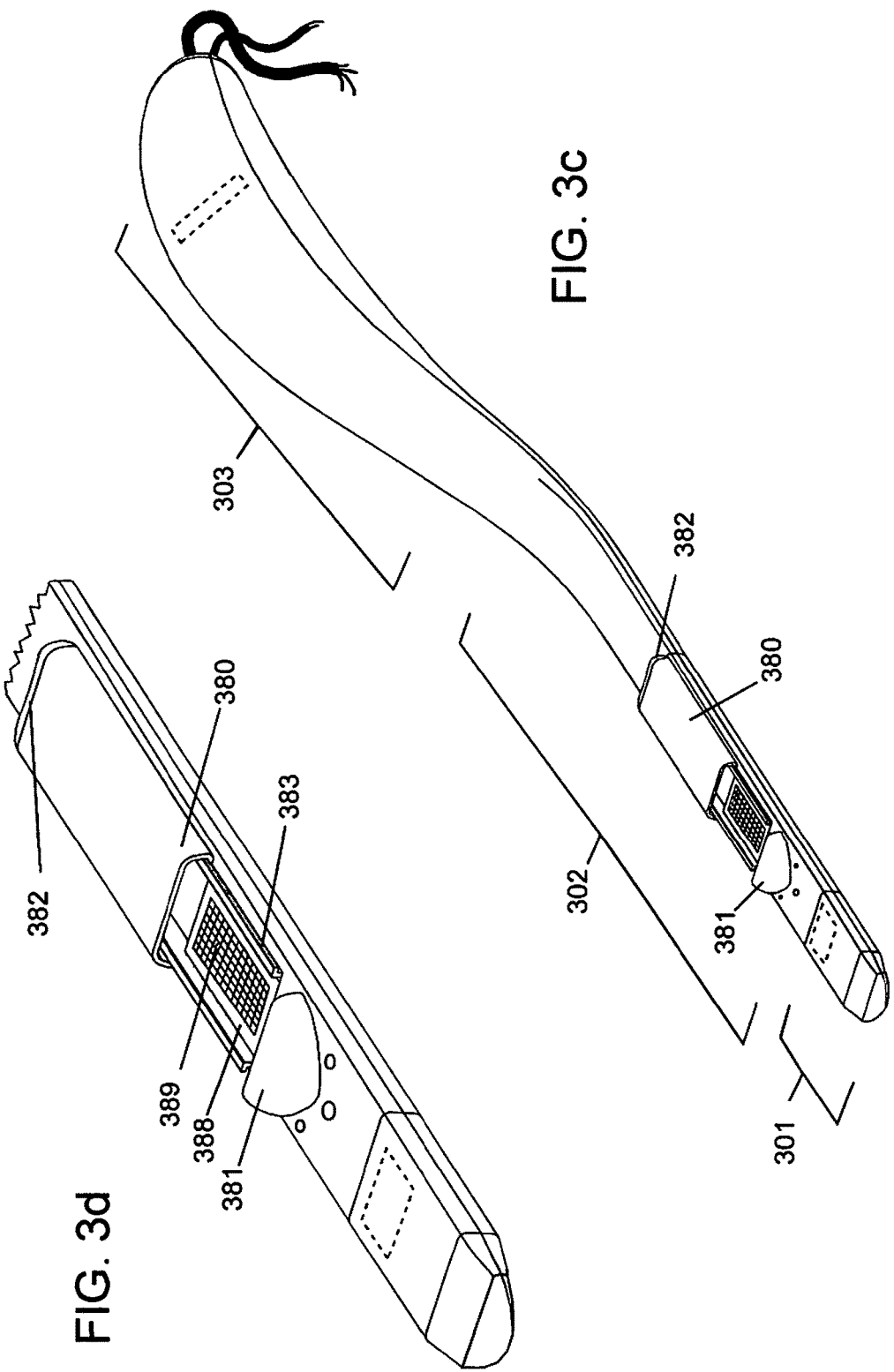

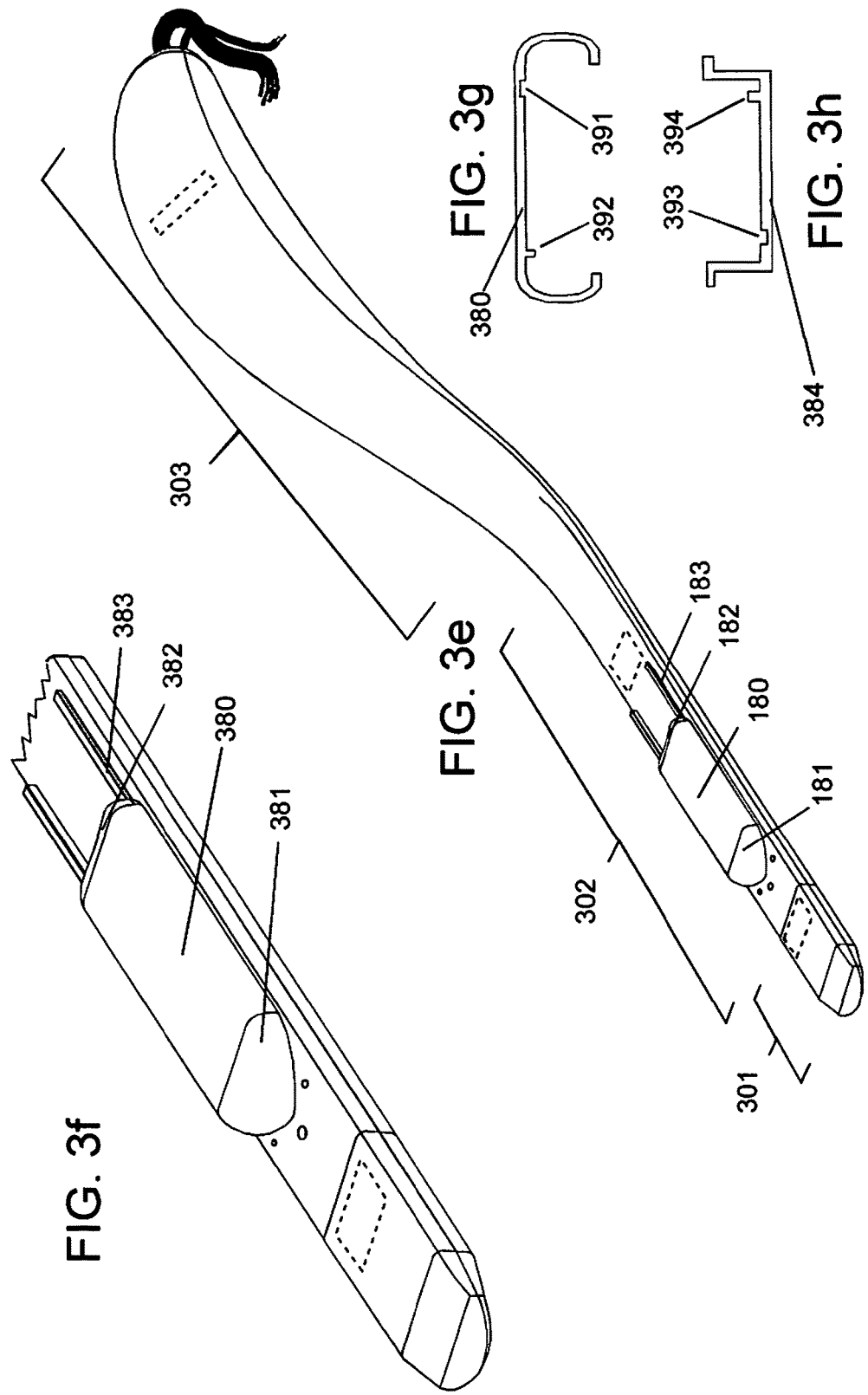

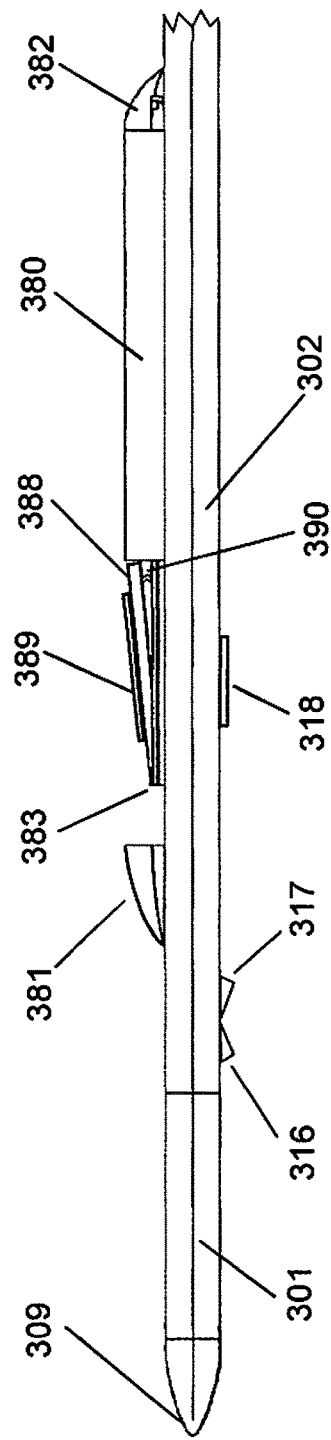
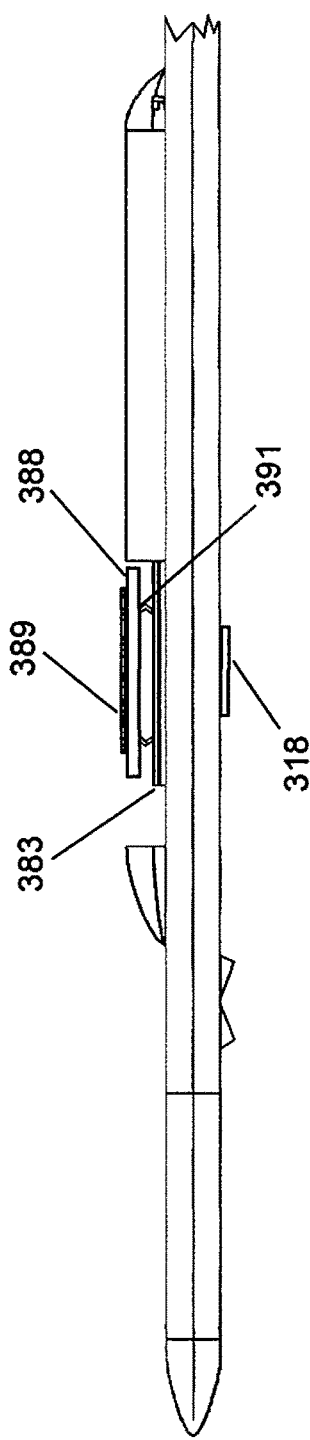
FIG. 3i
FIG. 3j

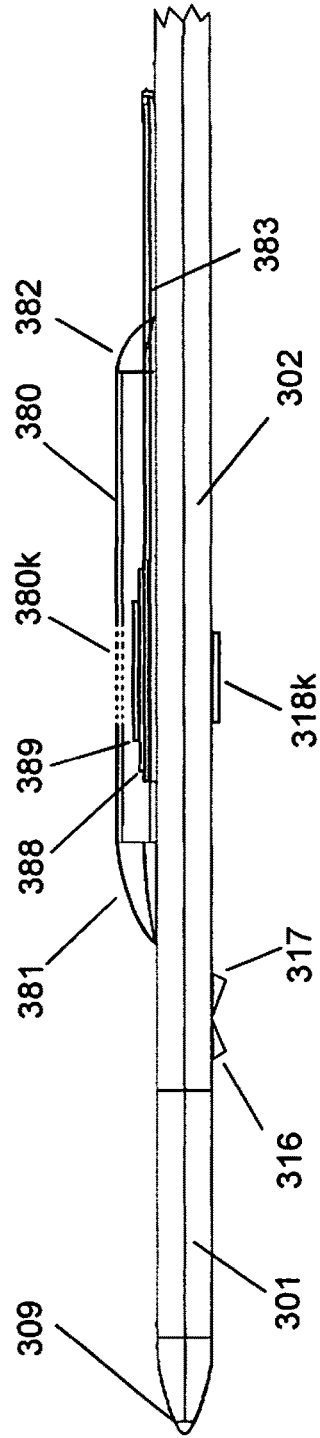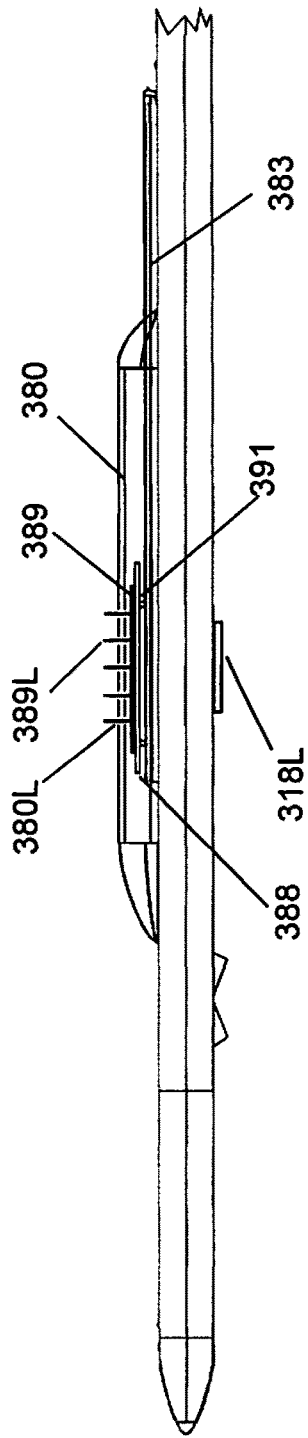

SYSTEMS, APPARATUS AND METHODS FOR TISSUE DISSECTION

BRIEF DESCRIPTION OF THE DRAWINGS

The written disclosure herein describes illustrative embodiments that are non-limiting and non-exhaustive. Reference is made to certain of such illustrative embodiments that are depicted in the figures, in which:

FIG. 1a is a perspective view of an embodiment of a tissue dissector (TD) with a sensor dock on the upper side of the device with the cover removed showing a dock with sensor.

FIG. 1b is a perspective view of a break-away portion of the embodiment previously depicted in FIG. 1a.

FIG. 1c is a perspective view of the embodiment previously depicted in FIG. 1a with the cover retracted revealing a dock and sensor.

FIG. 1d is a perspective view of a break-away portion of the embodiment previously depicted in FIG. 1c dissector wherein the cover is retracted.

FIG. 1e is a perspective view of the embodiment previously depicted in FIG. 1a with the cover closed thereby covering and sealing the dock.

FIG. 1f is a perspective view of a break-away portion of the embodiment previously depicted in FIG. 1e wherein the cover is closed over the dock.

FIG. 1g is a cross sectional view of an embodiment of a cover comprising a protrusion and a groove.

FIG. 1h is a cross sectional view of an embodiment of a dock comprising a protrusion and a groove.

FIG. 1i is a side view of the embodiment previously depicted in FIG. 1a of a TD illustrating an example of positioning a sensor at an angle different from the shaft axis.

FIG. 1j is a side view of the embodiment previously depicted in FIG. 1a of a TD illustrating an example of positioning a sensor at an angle substantially parallel to the shaft axis.

FIG. 1k is a side view of an alternative embodiment of a TD, in which the cover comprises openings.

FIG. 1L is a side view of an alternative embodiment of a TD, in which the cover comprises openings and a portion of the sensor protrudes through the openings.

FIG. 2a is a perspective view of an embodiment of a tissue dissector (TD) with a sensor dock on the upper side of the device with the cover removed showing a dock with a sensor.

FIG. 2b is a perspective view of a break-away portion of the embodiment previously depicted in FIG. 2a.

FIG. 2bb is a perspective view of a break-away portion of an alternative embodiment of a TD, in which the shaft separates revealing a dock.

FIG. 2c is a perspective view of the embodiment previously depicted in FIG. 1a with the cover retracted revealing a dock and sensor.

FIG. 2d is a perspective view of a break-away portion of the embodiment previously depicted in FIG. 2c dissector wherein the cover is retracted.

FIG. 2e is a perspective view of the embodiment previously depicted in FIG. 2a with the cover closed thereby covering and sealing the dock.

FIG. 2f is a perspective view of a break-away portion of the embodiment previously depicted in FIG. 2e wherein the cover is closed over the dock.

FIG. 2g is a cross sectional view of an embodiment of a cover comprising a protrusion and a groove.

FIG. 2h is a cross sectional view of an embodiment of a dock comprising a protrusion and a groove.

FIG. 2i is a side view of the embodiment previously depicted in FIG. 2a of a TD illustrating an example of positioning a sensor at an angle different from the shaft axis.

FIG. 2j is a side view of the embodiment previously depicted in FIG. 2a of a TD illustrating an example of positioning a sensor at an angle substantially parallel to the shaft axis.

FIG. 3a is a perspective view of an embodiment of a tissue dissector (TD) with a sensor dock on the upper side of the device with the cover removed; this embodiment lacks tip protrusions or lysing segments.

FIG. 3b is a perspective view of a break-away portion of the embodiment previously depicted in FIG. 3a.

FIG. 3bb is a perspective view of a break-away portion of the embodiment previously depicted in FIG. 3a wherein the dock may be positioned within the shaft or tip and may be exposed when adjacent portions of the shaft or tip may be separated telescopically.

FIG. 3c is a perspective view of the embodiment previously depicted in FIG. 3a with the cover retracted revealing a dock and sensor.

FIG. 3d is a perspective view of a break-away portion of the embodiment previously depicted in FIG. 3c dissector wherein the cover is retracted.

FIG. 3e is a perspective view of the embodiment previously depicted in FIG. 3a with the cover closed thereby covering and sealing the dock.

FIG. 3f is a perspective view of a break-away portion of the embodiment previously depicted in FIG. 3e wherein the cover is closed over the dock.

FIG. 3g is a cross sectional view of an embodiment of a cover comprising a protrusion and a groove.

FIG. 3h is a cross sectional view of an embodiment of a dock comprising a protrusion and a groove.

FIG. 3i is a side view of the embodiment previously depicted in FIG. 3a of a TD illustrating an example of positioning a sensor at an angle different from the shaft axis.

FIG. 3j is a side view of the embodiment previously depicted in FIG. 3a of a TD illustrating an example of positioning a sensor at an angle substantially parallel to the shaft axis.

FIG. 3k is a side view of an alternative embodiment of a TD, in which the cover comprises openings.

FIG. 3L is a side view of an alternative embodiment of a TD, in which the cover comprises openings and a portion of the sensor protrudes through the openings.

FIG. 4a is a side view of a robotic surgery system comprising a TD

FIG. 4b depicts an alternative robotic arm that may be used with the system of FIG. 4a.

DETAILED DESCRIPTION

Figure 2K:
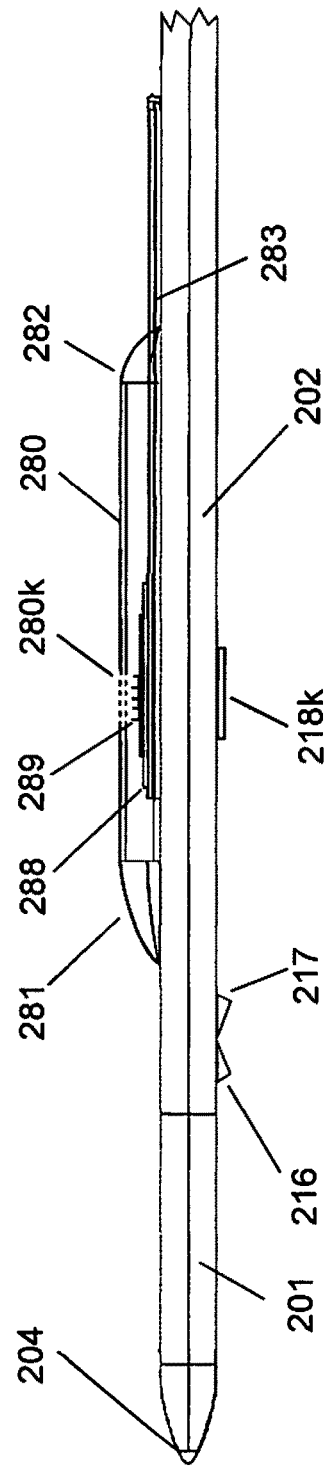
FIG. 2k is a side view of an alternative embodiment of a TD, in which the cover comprises openings.

During some surgeries, surgeons, patients, and operating staff spend time waiting for a laboratory specimen, obtained during invasive surgery, to be transported to the lab, prepared and processed in the lab, and reported back, while the patient may be under anesthesia. The advent of 'Lab on a Chip' technology may offer the possibility of some relief. Some 'Labs on Chips' may include nanosensors and optic sensors; however, their placement and/or use inside a living creature may present a different environment than that of a laboratory benchtop. Perhaps mimicking and/or modulating a small-scale environment external to a 'Lab on a Chip' by housing and/or docking chip(s) in various manners, in/on probes, chip function and/or use may be facilitated.

The term dissection may indicate the separation of tissues or of one tissue plane from another (ref: Free Online Medical Dictionary). Some also consider dissection to comprise separation of a single tissue into portions. Much of the bodies of animals and humans are formed from embryonic fusion planes. Many of the organs of the human body are categorized from the embryonic fusion planes from whence they came. The interfaces between organs may often be referred to as 'tissue planes.' Such planes may be considered substantially planar depending upon the size of a comparative planar living or inanimate object (such as a surgical instrument). As an example, a lobe of a human liver has a radius of curvature of about 5 cm; however, compared to a surgical instrument of about 1 cm in width capable of separating tissue in a plane, the curvilinear plane comprising the liver lobe may be 'substantially' planar and thus amenable to a tool capable of separating tissues in a 'substantially planar' fashion.

The term 'minimally invasive surgery' has been used to describe a procedure (surgical or otherwise) that is less invasive than open surgery used for the same purpose. Some minimally invasive procedures typically involve use of laparoscopic devices and remote-control manipulation of instruments with indirect observation of the surgical field through an endoscope or similar device, and are carried out through the skin or through a body cavity or anatomical opening. This may result in shorter hospital stays, or allow outpatient treatment (reference: Wikipedia).

Various implementations of methods are disclosed herein for dissecting and modifying various living tissues. Such methods may be performed using a Tissue Dissecting and Modifying Wand ("TDM"). Examples of various embodiments of such wands may be found in U.S. Pat. No. 6,203,540 titled "Ultrasound and Laser Face-Lift and Bulbous Lysing Device," U.S. Pat. No. 6,391,023 titled "Thermal Radiation Facelift Device," U.S. Pat. No. 6,432,101 titled "Surgical Device for Performing Face-Lifting Using Electromagnetic Radiation," U.S. Pat. No. 6,440,121 titled "Surgical Device For Performing Face-Lifting Surgery Using Radiofrequency Energy," U.S. Pat. No. 6,974,450 titled "Face-Lifting Device," and U.S. Pat. No. 7,494,488 titled "Facial Tissue Strengthening and Tightening Device and Methods." The "Detailed Description of the Invention" section of each of these patents is hereby incorporated herein by specific reference. With respect to U.S. Pat. No. 6,203,540 titled "Ultrasound and Laser Face-Lift and Bulbous Lysing Device," the section titled "Description of the Preferred Embodiments" is hereby incorporated herein by specific reference.

Various methods may therefore be implemented in which the amount of energy and/or the delivery time may be adjusted so as to heat the tissue to within a desired temperature range. Temperature sensors may therefore be incorporated on or near the energy windows to allow a surgeon to heat the tissue to a desired temperature or within a desired temperature range. In some embodiments, the sensor may be configured to provide an average temperature over a particular period of time and or over a particular range of distances within the tissue. Systems consistent with the disclosure provided herein may be configured to prevent or to shut down or otherwise limit energy transfer if a particular tissue temperature were beyond a threshold or alternatively if an average temperature threshold is reached.

Some embodiments disclosed herein may comprise one or more biosensors for detecting and/or analyzing a biological analyte. Such biosensors may comprise, for example, one or more sensitive biological elements, such as tissue, microorganisms, enzymes, antibodies, nucleic acids, etc. Such biosensors may also comprise a transducer. Systems comprising surgical tools comprising such biosensors may also comprise an electronic system comprising, for example, a signal amplifier, processor, and display to compile and/or display information from the biosensor. Examples of biosensors that may be useful in connection with one or more embodiments disclosed herein include nanobiosensors, optical biosensors, electrochemical biosensors, piezoelectric biosensors, electronic biosensors, gravimetric biosensors, and pyroelectric biosensors.

In other embodiments, one or more radiation detecting sensors may be provided. In some such embodiments, such radiation detectors may be configured to detect all species of radiation, including beta particles, gamma rays, x-rays, alpha particles, and neutrons. In some embodiments comprising one or more radiation sensors, the radiation sensor(s) may be positioned within a dock on a surgical tool. Such dock, as described elsewhere herein, may be configured to be sealed with a cover. As such, a gas, such as an electrically biased gas, may be introduced into the dock with the cover in a closed position. Such gas or gasses may be introduced by a fluid port also positioned within the dock. Radiation within a patient's body may then be detected by way of interaction with tailored nanoparticles, which may release secondary charged particles that ionize the gas within the dock.

The ionized gas may then be withdrawn from the dock by way of, for example, a fluid extraction port, as discussed elsewhere herein, for analysis. Such analysis may comprise collection of ionized particles on biased electrodes, which may result in a characteristic electrical signal that may be detected to indicate the detection of one or more forms of radiation.

In other embodiments, the electrodes used for this analysis may also be provided within the dock and the resulting signal may be transmitted electronically (wired or wirelessly) outside of the patient's body for processing. Alternatively, the signal may also be processed on the device and the resulting data stored on a local storage medium. Examples of radiation detection systems and techniques that may be useful for one or more embodiments disclosed herein may be found in "A Nanoparticle Doped Micro-Geiger Counter for Multispecies Radiation Detection," Journal of Microelectromechanical Systems, Volume 18, Issue 5, pp. 998-1003 (October 2009), which article is hereby incorporated by reference in its entirety.

Examples of other sensors that may be provided with one or more embodiments disclosed herein include electromagnetic sensors, electrical sensors, and temperature sensors. Examples of electromagnetic sensors may include colorimeter, electro-optical sensor, infrared sensor, photodetector, fiberoptic sensor, and/or LEDs as sensors, etc.; also LEDs can be multiplexed in such a circuit, such that it can be used for both light emission and sensing at different times. Examples of electrical sensors may include oxygen sensor, $CO_2$ sensor, pH glass electrode, and/or a current sensor, etc. Examples, of thermal sensors may include Infrared thermometer, resistance temperature detector, resistance temperature detector, resistance thermometer, thermistor, thermocouple, thermometer, etc.

Temperature sensors that may be useful in connection with embodiments disclosed herein include, but are not limited to, resistance temperature sensors, such as carbon resistors, film thermometers, wire-wound thermometers, or coil elements. Some embodiments may comprise thermocouples, pyrometers, or non-contact temperature sensors, such as total radiation or photoelectric sensors. In some embodiments, one or more temperature sensors may be coupled with a processor and/or a monitor to allow a surgeon to better visualize or otherwise control the delivery of energy to selected areas of target tissue. For example, some embodiments may be configured such that a surgeon can visualize the temperature of tissue positioned adjacent to one or more locations along the TD to ensure that such temperatures are within a desired temperature range. Some embodiments may alternatively, or additionally, be configured such that one or more temperature sensors are coupled with a processor in a feedback loop such that energy delivery may be automatically adjusted by the system in response to temperature data. For example, when temperatures exceed a particular threshold, such as somewhere between about 65° C. and about 90° C., the system may be configured to shut down or otherwise limit further energy delivery. In some such embodiments, the threshold may be between about 68° C. and about 75° C.

Some embodiments may comprise a feedback means, such as a visual, audible, or tactile feedback means, to provide information to a user to avoid excess energy delivery to tissues. In some embodiments, the feedback means may be configured to notify the surgeon when the temperature has reached a particular threshold. In some embodiments, the feedback means may be configured to notify the surgeon when the TD has been positioned in a particular location within the target region for a particular time period. Examples of visual feedback means include LED lights, LASERS, visual light source, display screen, etc. Examples of audible feedback means include speakers, alarms, audible vibration, etc., Examples of tactile feedback means include vibration, minimal electrical shock, heat, etc., The feedback means may be configured with multiple thresholds with different feedback at each threshold. For example, at a first threshold, the TD may be configured to deliver a first noise and at a second threshold the TD may be configured to deliver a second noise. The second noise may be louder than the first noise to indicate a greater urgency for changing the energy delivery and/or moving the TD from its current location within a patient's body. In some embodiments, an antenna(s) may be present on the shaft or tip of the TD. In some embodiments, a camera or fiberoptic may gather optical data to allow the surgeon knowledge of the placement of the TD.

The term Tissue Dissector (TD) is intended to encompass any of the devices for dissecting tissue disclosed herein including Tissue Dissecting and Modifying Wands (TDM) comprising lysing segments and tissue dissecting wands lacking lysing segments.

The term 'modifying' in this context may refer to or may encompass application of energy to tissue using one or more lysing segments as discussed herein. The term 'modifying' in this context may also refer to application of energy to tissue by way of an energy window as also described herein.

Further details regarding various embodiments will now be provided with reference to the drawings.

FIG. 1a-j depict various views of a particular embodiment of a tissue dissector (TD) with a sensor dock on the upper side of the device with a movable cover.

FIG. 1a is a perspective view of an embodiment of a TD comprising a tip 101, a shaft 102 and a handle 103. Located on the shaft is dock 184 that may accommodate seat 188 which may releasably hold sensor 189. In some embodiments sensor 189 may comprise a nanosensor. In some embodiments, dock 184 may be recessed into shaft 102 and/or tip 101. In some embodiments dock 184 may protrude from shaft 102 and/or tip 101. In some embodiments dock 184 may be flush with shaft 102 and/or tip 101. In some embodiments, sensor 189 may comprise a silicon nanowire sensor. In some embodiments the sensor 189 may comprise a biological nanosensor. In some embodiments, nanosensor 189 may comprise a conducting polymer and/or glass and/or polymer and/or plastic and/or graphene and/or carbon, etc. In some embodiments, seat 188 may be fixed in position. In some embodiments, seat 188 may be moveable. In some embodiments sensor 184 may be fixed in seat 188. In some embodiments, the sensor 189 may be detachable seat 188. It is contemplated that in alternative embodiments, seat 188 may be omitted. In some embodiments the dock may comprise cover moving means and/or a cover tip. Cover tip 181 and means for selectively moving a cover 183 may be positioned adjacent dock 184. Examples of such cover moving means may include rails, grooves, tracks, ratchets, cables, arms, lines, etc. In the depicted embodiment the cover moving means comprises a rail. In some embodiments a portion of the shaft may comprise cover moving means 183. It is contemplated that in alternative embodiments, cover moving means 183 may be omitted. Dock 184 may comprise one or more dock wall(s) 185. Dock wall 185 may comprise fluid delivery port 186 for fluid delivery conduit. Dock wall 185 may comprise fluid extraction port 187 for fluid extraction conduit. Fluid delivery port 186 may, in some embodiments, be configured to deliver a gas, such as a low-humidity gas, a noble gas, and/or other gases that may be useful for drying out dock 184, such as may be useful following cleaning of dock 184. In such embodiments, fluid extraction port 187 may be used to remove gases from dock 184 so as to allow for desired circulation of such gases within dock 184. In some embodiments, dock wall 185 may comprise one or more ports 186 and/or 187. In FIG. 1c, cover 180 is moveable along cover moving means 183 and may be opened or closed via internal control wires. In some embodiments the cover may be moved by motors. Rear end of cover 182 may be fixed to cover 180. In some embodiments, rear end of cover 182 is not fixed to cover and is itself attached to another portion of the TD. In some embodiments, dock 184 and/or dock wall 185 may accommodate a temperature modification means 195 for modifying a temperature within the dock 184 and cover 180. Temperature modification means 195 may comprise, for example a heater, a Peltier cooler, a heat pump, etc. Temperature modification means 195 may be used to heat fluids introduced by way of port 186. Temperature modification means 195 may alternatively be used to heat tissues and/or other fluids such as body tissues and/or fluids captured during a procedure using the TD. In some embodiments temperature modification means 195 may facilitate and/or inhibit certain chemical reactions and/or bond alterations that may be needed in order to sense certain biomaterials using sensor 189. In some embodiments, dock 184 and/or dock wall 185 may accommodate mixing element 196. In some embodiments temperature modification means 195 may comprise an electrical resistance heater. In contemplated embodiments, heater 195 may comprise a thin film resistor and/or piezoelectric heating device and/or other device capable of heating fluids. In some embodiments, mixing element 196 may comprise a propeller driven by an electric motor. In some embodiments, mixing element 196 may comprise one or more flaps of relatively inert flexible polymeric plastic on a post spun by an electric motor. Examples of other materials for such a flap may include polymers, metals, ceramics, etc. In another embodiment, mixing element 196 may comprise an unattached stirring rod spun by oscillating magnet. In a contemplated embodiment, a separate set of ports may originate and terminate in dock 184, and may be connected by conduit which is fluidly coupled with a piezoelectric pump and/or another fluidic motor and/or another fluidic driving device. In embodiments including one or more such additional ports, such port(s) may be positioned at an opposite end of dock 184 such that delivery of fluid(s) and/or application of a vacuum may be applied more evenly throughout dock 184. It is contemplated that in alternative embodiments, temperature modification means 195 and/or mixing element 196 may be omitted. One or more sensors 178 and/or 179 may be located on dock 184. In some embodiments, one or more sensors 178 and/or 179 may be located on dock wall 185 and/or cover 180. Sensors 178 and/or 179 may comprise any of the specific examples of sensors discussed in connection with sensors 110 and/or 114. Sensor(s) 178 and/or 179 may report conditions and/or changing conditions in dock area 184 in and/or around nanosensor 189.

Nanosensors may be obtained/manufactured by methods available to those of ordinary skill in the art, including but not limited to: U.S. Pat. No. 8,022,444 B2 titled "Biosensor and Method of Manufacturing the Same," and/or U.S. Pat. No. 8,314,357 B2 titled "Joule Heated Nanowire Biosensors," and/or U.S. Pat. No. 8,236,595 B2 titled "Nanowire Sensor, Nanowire Sensor Array and Method of Fabricating the Same," and/or Label Free DNA Sensor Using a Silicon Nanowire Array (Kulkarni, Xu, Ahn, Amin, et. al.; J Biotechnol, 2012, Aug. 31; 160(3-4):91-6.) and/or Conducting Polymers: An Emerging Field of Biosensors (Borole, D D et al.; Des Monomers Polymers, 2006 9(1): p. 1-11.) and/or Conducting Polymers for DNA Sensors and DNA Chips: from Fabrication to Molecular Detection (Mailley, Livache; Electrochemistry of Nucleic Acids and Proteins—Towards Electrochemical Sensors for Genomics and Proteomics, 2005: p. 297-330.) and/or Conducting Polymers for Electrochemical DNA Sensing (Peng, H., et al., Biomaterials, 2009, 30(11): p. 2132-2148.) and/or Conductive Electroactive Polymers: Intelligent Materials Systems (Wallace, Spinks, Teasdale. Vol. 317. 1998.287-290.) Conducting Polymer Nanowire-based Biosensors (Wanekaya, et al.; Handbook of Biosensors and Biochips, 2007 (2) p. 831-842.) and/or Conductive Electroactive Polymers: Intelligent Materials Systems, Second Edition, 2002 (Wallace, Spinks, Kane-Maguire p224.) and/or Novel Conducting Polymers for DNA Sensing (Peng et al.; Macromolecules, 2007, 40(4): p. 909-914.) and/or Direct Ultrasensitive Electrical Detection of DNA and DNA Sequence Variations Using Nanowire Nanosensors (Nano Letters, 2003. 4(1): p. 51-54.) and/or Sequence-Specific Label-Free DNA Sensors Based on Silicon Nanowires (Li, et al; Nano Letters, 2004. 4(2): P. 245-247.) and/or Sensing by Silicon Nanowire: Charge Layer Distance Dependence (Zhang, et al.; Nano Letters, 2008. 8(4): p. 1066-1070.) and/or Nanowire Nanosensors for Highly Sensitive and Selective Detection of Biological and Chemical Species (Yi Cui, et al.; Science vol 293 (2001) p. 1289.) and/or U.S. Pat. No. 17,993,538 B2, titled "Patterning by Energetically-Stimulated Local Removal of Solid-Condensed-Gas Layers and Solid State Chemical Reactions Produced with Such Layers" and/or U.S. Pat. No. 7,674,389 B2 titled "Precision Shape Modification of Nanodevices with a Low-Energy Electron Beam," and/or U.S. Pat. No. 5,645,740 titled "System and Assemblage for Producing Microtexturized Substrates and Implants," and/or U.S. Pat. No. 5,607,607 titled "System and Assemblage for Producing Microtexturized Substrates and Implants," and/or U.S. Pat. No. 7,416,911 B2 titled "Electrochemical Method for Attaching Molecular and Biomolecular Structures to Semiconductor Microstructures and Nanostructures," and/or U.S. Pat. No. 7,294,526 B2 titled "Nano Optical Sensors via Molecular Self-Assembly," and/or U.S. Pat. No. 6,870,235 B2 titled "Silicon-on-Insulator Biosensor Device," and/or U.S. patent application Ser. No. 12/065,857, Publication No: US2009/0140167 A1, titled "Nanotube Fabric-Based Sensor Systems and Methods of Making Same," and/or U.S. Pat. No. 6,716,620, filed Mar. 26, 2001, titled "Biosensor and Related Method," and/or U.S. Pat. No. 7,129,554 B2, titled "Nanosensors," and/or U.S. patent application Ser. No. 13/209,442, publication number US2012/0304776 A1, titled "Chemical and Biomedical Nanosensors" which are hereby incorporated by reference in its entirety.

For example, some of the reagents and/or chemicals and/or biochemicals that may be present in and/or delivered to and/or removed from the dock area to facilitate sensor use and/or cleaning, etc., may include but not be limited to ethanolic solutions, thiols, SDS (sodium dodecyl sulfate), water, argon gas, sodium chloride, sodium bicarbonate buffer, EGTA (ethylene glycol tetraacetic acid), EDTA (ethylenediaminetetraacetic acid), sulfo-NHS diazirine (sulfo-SDA), PBS (phosphate buffered saline), and/or Tween®-20 (PBST), etc. Such reagents and/or chemicals and/or biochemical and their acquisition and use are available to those of ordinary skill in the art, including but not limited to: U.S. Pat. No. 6,593,093 B1 titled "Detection of Group A Streptococcus"; U.S. Patent Application Publication No. 2012/0228155A1 titled "Electromagnetic Detection of Analytes"; U.S. Patent Application Publication No. 2009/0186774 A1 titled "Sepsis Detection Microarray"; European Patent 2526427 A2, titled Rapid Pathogen Diagnostic Device and Method"; U.S. Patent Application Publication No. 2006/0223080 A1, titled "Compositions and Methods for Detecting Group A Streptococci"; Scanometric DNA Array Detection with Nanoparticle Probes (TATON, MIRKIN, LESTINGER; Science, 8 Sep. 2000, vol. 289, no 5485, pp 1757-1760.); Detection of Methicillin-Resistant Staphylococcus aureus (MRSA) using the NanoLantern Biosensor (STROHSAHL, MILLER, KRAUSS; Proc. of SPIE, Vol 7167OS pp. 1-12.); Ultrasensitive and Selective Multiplexing Detection of Cancer Markers Using Nanowire Nanosensors (CIU, WANG, HUYNH, LIEBER; Harvard University, pp 1-21.); Field Effect Transistor Nanosensor for Breast Cancer Diagnostics (MOHANTY, CHEN, WANG, HONG, ROSENBERG, WEAVER, ERRAMILLI; Boston University, pp. 1-25.); all of which are hereby incorporated herein by reference in their entirety.

In some embodiments, sensor 178 and or sensor 179 may comprise a camera. In some embodiments, sensor 178 and or sensor 179 may comprise a fiberoptic and/or fiberoptic camera and/or CCD camera and/or other camera.

In some embodiments, one or more electromagnetic delivery elements 177 may be positioned on dock 184 tip and/or cover 180 and/or tip of cover 181. Other embodiments may comprise one or more electromagnetic delivery elements on any other suitable location on the TD, including but not limited to on the sensor 189 or otherwise on seat 188. Electromagnetic delivery elements that may be useful include but are not limited to: LEDs, LASERs, fiberoptics, filaments, photoelectric materials, infrared emitters, etc. In some implementations, emission of such electromagnetic energy may be absorbed by a chemical and/or biomolecule on the sensor and/or dock area and/or reflectance and/or emission spectra of the chemical and/or biomolecule and/or a further product may be detected via sensors 178 and/or 179. In some embodiments, seat 188 may be configured to seal, or at least substantially seal, one or more portions of one or more sensors positioned on seat 188. For example, in some embodiments, seat 188 may comprise a periphery having a skirt configured to encapsulate at least a portion of a perimeter of the sensor contained therein. In some such embodiments, the skirt may comprise a flexible material, such as a plastic or rubber material, to allow the sensor to be positioned therein and seal the perimeter in order to, for example, prevent fluids from reaching certain portions of the sensor, such as a lower surface of the sensor. In other embodiments, the seat may be configured with an opening through which the sensor may extend. In other words, in such embodiments, a portion of the sensor may be positioned below the opening and a portion of the sensor, such as a portion configured to interact with biological tissues and/or fluids, may extend above the seat. The sensor may be configured in such embodiments to be secured underneath the seat opening by, for example, snap-fit engagement, friction fit, threaded coupling, bayonet clamp, etc. In embodiments comprising a seat opening, such opening may be configured to automatically seal around the portion of the sensor adjacent to the opening such as, for example, by use of suitable materials, such as self-sealing polymers and the like.

In an embodiment, cover 180 and/or dock 184 may be configured to reflect electromagnetic radiation. Reflecting electromagnetic radiation and/or having mirror-like properties may allow for detection of electromagnetic radiation by sensors 178 and/or 179. In some embodiments, cover 180 and/or dock 184 comprise a thin film coating over a substrate. In some embodiments, the substrate may be plastics and/or molded polymer and/or crystal and/or glass and/or metal, etc. In some embodiments, cover 180 and/or dock 184 comprise a coating of aluminum. In some embodiments the aluminum coating comprises a protected aluminum and/or enhanced aluminum and/or UV-enhanced aluminum (a maker may be Edmund Optics, Barrington, N.J., USA).

In the depicted embodiment cover 180 may comprise plastic. In other embodiments cover 180 may comprise materials including but not limited to: polymers, quartz, glass, carbon based materials, silicates and/or metals.

The conduit may also contain electrical control wires to aid in device operation. Partially hidden from direct view in FIGS. 1a & 1b, and located in the grooves defined by protrusions 104 are electrically conductive tissue lysing elements 105, which, when powered by an electrosurgical generator, effects lysing of tissue planes on forward motion of the device. The lysing segments may be located at the termini of conductive elements. In some embodiments, one or more sensors such as for example sensors 110 and 114 may be positioned on the device. The sensors 110 and 114 may comprise any of the sensors described in the specification herein. In some embodiments, sensor 110 and or sensor 114 may comprise a camera. In some embodiments, sensor 110 and or sensor 114 may comprise a fiberoptic and/or fiberoptic camera and/or CCD camera and/or other camera. Other embodiments may comprise one or more sensors on any other suitable location on the TD, including but not limited to on the protrusions or otherwise on the tip, and on the shaft. Sensors that may be useful include thermal sensors, photoelectric or photo optic sensors, cameras, etc. In some embodiments, one or more sensors may be used to monitor the local post passage electrical impedance or thermal conditions that may exist near the distal tip of the shaft or on the tip. Some embodiments may also comprise one or more sensors incorporating MEMS (Micro Electro-Mechanical Systems) technology, such as MEMS gyroscopes, accelerometers, and the like. Such sensors may be positioned at any number of locations on the TD, including within the handle in some embodiments. In some embodiments, sensor 114 may comprise fiberoptic elements. In an embodiment, the sensor can be configured to sense a temperature of tissue adjacent to the apparatus. The temperature sensor may alternatively be configured or sense a temperature of one or more fluids adjacent to the apparatus such as for example tissue fluids and/or fluids introduced by the surgeon.

Temperature and impedance values may be tracked on a display screen or directly linked to a microprocessor capable of signaling control electronics to alter the energy delivered to the tip when preset values are approached or exceeded. Typical instrumentation paths are widely known, such as thermal sensing thermistors, and may feed to analog amplifiers which, in turn, feed analog digital converters leading to a microprocessor. In some embodiments, internal or external ultrasound measurements may also provide information which may be incorporated into a feedback circuit. In an embodiment, an optional mid and low frequency ultrasound transducer may also be activated to transmit energy to the tip and provide additional heating and may additionally improve lysing. In some embodiments, a flashing visible light source, for example, an LED, can be mounted on the tip may show through the tissues and/or organs to identify the location of the device.

In some embodiments, one or more electromagnetic delivery elements 115 may be positioned on tip or shaft. Other embodiments may comprise one or more electromagnetic delivery elements on any other suitable location on the TD, including but not limited to on the protrusions or otherwise on the tip, and on the shaft. Electromagnetic delivery elements that may be useful include: LEDs, LASERs, fiberoptics, filaments, photoelectric materials, infrared emitters, etc.

As shown in FIG. 1a, handle 103 may comprise one or more ports through which various conduits may be passed. In some such embodiments, a plurality of conduits may be bundled together for convenience if desired. For example, in the depicted embodiment, an energy delivery conduit bundle 198 may be provided, which may comprise a lysing segment energy conduit 111 and an energy window conduit 112. In addition, a miscellaneous conduit bundle 199 may be provided. Miscellaneous conduit bundle 199 may comprise, for example, various other conduits, such as conduits for one or more sensors, such as sensors 110 and 114, one or more electromagnetic delivery elements 115, fluid delivery port(s) 116, and/or suction/vacuum ports 117. In addition, miscellaneous conduit bundle 199 may comprise one or more additional conduits, such as one or more additional fluid delivery conduits for delivering a fluid, such as a liquid or gas, to port 186 in dock 184 in the TD. Miscellaneous conduit bundle 199 may further comprise one or more fluid extraction conduits (from port 187 in dock 184) for extracting of fluid to direct the fluid (again, a liquid or gas) to a remote fluid/chemical sensor.

The fluid delivery conduit (leading to port 186) may be configured to deliver, for example, buffers, cleansers, quenching agents, reagents, biological compounds, inert compounds, gases. Fluids delivered (by way of a fluid delivery conduit leading to port 186) may be energized, such as heated, ultrasonically energized, may contain detergents, antibodies, drugs, etc.

Fluid extraction conduits (leading from port 187) may not only be used to withdraw fluids to be discarded from the body, but also may be used in a wash circuit to remove fluids introduced by way of fluid delivery conduit leading to port 186 that are used to, for example, wash and/or disinfect certain tissues and/or components of the TD. Fluid extraction conduit (leading from port 187) may also be used to extract fluids for external analysis. Some embodiments may be configured to provide a bubble between separate sets of fluids to allow a user to distinguish between various fluid streams delivered using fluid extraction conduit leading from port 187.

In some embodiments, a vibration means 170 may be positioned in the handle. Other embodiments may comprise one or more vibration means on any other suitable location on the TD, including but not limited to on the protrusions or otherwise on the tip, and on the shaft. Examples of suitable vibration means may include piezoelectric materials, ultrasonic motors with stators, piezoelectric actuators, vibration motor such as an off-center weight mounted on a gear, etc. Some vibration means may be configured to emit ultrasound in the 20-40 kHz range. Yet other vibration means may include electromagnet drivers with a frequency of operation in the range of 150-400 Hz. In some embodiments, one or more vibration means may be used to provide additional forces which may facilitate passage of the TD. In some embodiments, one or more vibration means may be used to reduce debris on the electrosurgical or other components of the TD. In a further embodiment, a vibration means may be directly or indirectly connected to one or more of the lysing segments. Some vibration means may help to decrease and/or remove debris. In some embodiments use of a vibration means may, also or alternatively, be used to assist in migrating the TD through tissue during the procedure. In some such embodiments, it is thought that use of a vibration means having a lower frequency may be particularly useful for assisting in such migration. In addition, positioning the vibration means closer to a handle of the TD may facilitate such migration as well. By contrast, positioning the vibration means on or near the tip, and/or using a higher frequency vibrations means may be particularly useful for preventing buildup of debris on the tip.

FIG. 1 d, c depict the TD with cover 180 moved proximally to expose dock.

FIG. 1 f, e depict the TD with cover 180 moved distally to close over and/or seal dock.

FIG. 1g is cross sectional view of an embodiment of cover 180 comprising a groove 191 and projection 192 as described herein. Groove 192 may be used to direct fluids within cover 180 to facilitate mixing of fluids and/or directing fluids to locations in need of cleaning and/or directing fluids to sensor locations and/or bringing fluids of with a temperature range to locations within the dock or cover. Similarly as described herein, projection 192 may also be used to direct fluids to one or more desired locations and/or agitate fluids in a desired manner for a particular use.

FIG. 1 h is cross sectional view of an embodiment of dock 184 comprising a groove 193 and a projection 194 as described herein. Groove 193 may be used to direct fluids within dock 184 to facilitate mixing of fluids and/or directing fluids to locations in need of cleaning and/or directing fluids to sensor locations and/or bringing fluids of with a temperature range to locations within the dock or cover. Similarly as described herein, projection 194 may also be used to direct fluids to one or more desired locations and/or agitate fluids in a desired manner for a particular use. In some embodiments, cover 180 and dock 184 may when cover 180 is in a closed position, define a common space. In some embodiments, cover grooves 191 may operate in conjunction with dock grooves 193 or dock protrusions 194 to impact fluid behavior in a desired manner.

In FIGS. 1g and/or 1h, one or more grooves 191 and 193 may be provided for example in dock 184 and/or in an interior surface of cover 180 in order to direct fluids delivered through port 186 are directed to desired to one or more desired locations. In some embodiments grooves may be configured to facilitate mixing of fluids and/or directing fluids to locations in need of cleaning and/or directing fluids to sensor locations. One or more projections 192 and 194 may be provided for example in dock 184 and/or in an interior surface of cover 180 in order to direct fluids delivered through port 186 are directed to desired to one or more desired locations. In some embodiments projections may be configured to facilitate mixing of fluids and/or directing fluids to locations in need of cleaning and/or directing fluids to sensor locations. In some embodiments multiple projections may define a groove, in other embodiments one or more grooves may be formed within a surface of a cover and/or dock.

With the cover 180 closed, as depicted in FIG. 1e, fluids may be circulated within the space enclosed by cover 180 which may facilitate cleaning. Closing cover 180 may also facilitate isolation of biological tissues and/or fluids. For example, closure of cover 180 may allow for analysis of tosses and/or fluids while preventing contamination by other such tissues and fluids after a sample has been taken. Cleaning may be further facilitated by positioning of the seat and/or sensors at an angle and/or various angles. The configuration depicted in FIG. 1i may be primarily for facilitating capture to tissue and/or fluids for analysis, however some embodiments may be configured to tilt seat 188 toward a rear portion of the TD such that it faces (tilts toward) fluid port 186 to facilitate cleaning of sensor 189.

Fluid delivery port 186 for fluid delivery and fluid extraction port 187 for fluid extraction may also serve to deliver and/or remove fluids, for example, including but not limited to reagents and/or analyte(s) and/or eluent(s) and/or eluate(s). In some embodiments, fluid delivery from fluid delivery port 186 and/or fluid extraction from fluid extraction port 187 may be linked in a circuit with a pump and/or additional conduit (that is coupled with one or both of the conduits coupled with fluid delivery port 186 and fluid extraction port 187) to recirculate and/or heat and/or incubate and/or mix and/or add reagents and/or remove reagents and/or other materials from the space within the cover 180 and/or dock 184. In some embodiments, a pump external to the TD, fluidly connected to the circuit between the conduits connecting ports 187 and 186, may be used to move fluids. The available space for fluids between the cover 180 and dock 184 (with space occupying elements) may be derived by measuring an amount of fluid entering and/or exiting from ports 186 and/or 187 via their conduits. Such measurements may be compared with CAD (Computer Aided Design) calculations of the space.

FIG. 1*i* is a side (break away) side view, of the embodiment previously depicted in FIG. 1*a* of a TD, illustrating an example of positioning and/or protruding a seat (containing a nanosensor) that may allow for some exposure to passing tissues or fluids. The TD may comprise an actuator 190. In some embodiments, actuator 190 may comprise a motor. In some embodiments actuator 190, may comprise one or more such motors such as a screw-drive motor, gear motor, hydraulic motors etc. In some embodiments actuator 190 may comprise worm gearheads, motor control circuits, monitors, remote control devices, etc. In some embodiments, actuator 190 may be controlled or moved by wire and/or spring. In some embodiments, actuator may be controlled or moved by wire using manual work. In some embodiments actuator 190 may be omitted. In some embodiments, seat 188 may be configured to be manually actuated or tilted. In some embodiments, seat 188 may be configured to be positioned in affixed number of angles relative to shaft 102 and/or dock. In other embodiments, seat 188 may be configured to be repositioned in an infinite number of angled positions relative to shaft 102 and/or dock.

Means for delivering ultrasonic energy 197 may be located in/on in/on dock wall 185 of dock 184. Ultrasonic means 197 may be configured to for example, heat fluids: aid in the cleaning of one or more portions of the TD including for example dock 184: aid in the mixing of reagents and/or organic chemicals and/or biomolecules; aid in the fixation of biomolecules and/or other substances to receptors and/or sensors; aid in the removal of biomolecules and/or other substances to receptors. In the depicted embodiment the ultrasonic means comprises a piezoelectric ceramic. In some embodiments the piezoelectric ceramic may measure about 2 mm×2 mm×4 mm. It is contemplated that in alternative embodiments, ultrasonic means 197 may be omitted. In some embodiments the piezoelectric ceramic is made from lead zirconate titanate piezoelectric ceramic (which may be sold as PZT8 or PZT4 by Micromechatronics, State College, Pa.) and may be driven by 2-5 Watts at 10-20 Volts and/or may be configured to vibrate at a frequency of 300-500 kiloHertz. In some embodiments the piezoelectric may comprise quartz and/or barium titanate and/or film polymer polyvinylidene fluoride. In some embodiments the ultrasonic means measures between 1 mm and 20 mm in any dimension. Some embodiments may comprise a plurality of ultrasonic means. In some embodiments, ultrasonic means may be configured to be positioned on two or more intersecting surfaces, for example in the embodiment depicted in FIG. 1 *b* a portion of ultrasonic means 197 is positioned on an upper surface of shaft 102 and a second portion of ultrasonic means 197 is positioned along dock wall 185 which intersects the upper surface of shaft 102. in the depicted embodiment wall 185 intersects the top surface of shaft 102 at a substantially perpendicular angle.

In the embodiment depicted in FIG. 1*i*, positioning the seat 188 and/or sensors 189 at one or more angles while the cover is in the open position may allow sensor(s) 189 to increase and/or alter contact and/or friction to facilitate a desired reaction between sensor 189 passing tissues and/or fluids.

In the embodiment depicted in FIG. 1*j*, positioning the seat 188 and/or sensors 189 at least at a substantially parallel angle with shaft 102 may be desirable or at least suitable for some applications.

In some embodiments, one or more suction/vacuum ports 117 may be provided on or about the tip or distal shaft. The port(s) may be fluidly coupled with a vacuum; the vacuum may comprise a pump or a negative pressure chamber or a syringe at the end of a fluid conduit. Other embodiments may comprise one or more suction/vacuum ports on any other suitable location on the TD, including but not limited to on the protrusions or otherwise on the tip, and on the shaft. In some embodiments, a fluid delivery port 116 may be provided. In some embodiments the fluid delivery port may be coupled with a pump or high pressure fluid. In some embodiments the port may be perpetually open such that fluid may be delivered therethrough upon actuation of a pump or fluid pressure system. In other embodiments the port may be closed and selectively opened to deliver fluid therethrough. Other embodiments may comprise one or more fluid ports on any other suitable location on the TD, including but not limited to on the protrusions or otherwise on the tip, and on the shaft. Fluid ports that may be useful may comprise channels within the TD, polymer lines, hoses, etc. Fluids that may emanate from the outlet may comprise ionic fluids such as saline, medicines (including but not limited to antibiotics, anesthetics, antineoplastic agents, bacteriostatic agents, etc.), non-ionic fluids, and or gasses (including but not limited to nitrogen, argon, air, etc.). In some embodiments fluids may be under higher pressures or sprayed. It should be understood that although these elements (116 & 117) are not depicted in every one of the other figures, any of the embodiments described herein may include one or more such elements.

In the depicted embodiment, 118 represents an antenna, such as an RFID TAG or Bluetooth antenna configured to deliver a signal to a receiver unit. In embodiments in which antenna 118 comprises an RFID TAG, the RFID tag may comprise an RFID transponder. In other embodiments the RFID tag may comprise a passive tag. It should be understood that antenna 118 is not depicted in every one of the other figures, any of the embodiments described herein may comprise one or more such elements. Other embodiments may comprise one or more antenna(s) on any other suitable location on the TD, including but not limited to on the protrusions or otherwise on the tip, and on the shaft. In embodiments wherein antenna(s) 118 comprises an RFID transponder such transponder may comprise a microchip, such as a microchip having a rewritable memory. In some embodiments, the tag may measure less than a few millimeters. In some embodiments a reader may generate an alternating electromagnetic field which activates the antenna, such as an RFID transponder, and data may be sent via frequency modulation. In embodiments comprising one or more RFID tags (or other antenna) the position(s) of the RFID tag(s) or other antenna may be determined by an alternating electromagnetic field in the ultra-high frequency range. The position may be related to a 3 dimensional mapping of the subject. In an embodiment the reader may generate an alternating electromagnetic field. In some such embodiments, the alternating electromagnetic field may be in the shortwave (13.56 MHz) or UHF (865-869 MHz) frequency. Examples of potentially useful systems and methods for mapping/tracking a surgical instrument in relation to a patient's body may be found in U.S. Patent Application Publication No. 2007/0225550 titled "System and Method for 3-D Tracking of Surgical Instrument in Relation to Patient Body, which is hereby incorporated by reference in its entirety.

In some embodiments, a transmission unit may be provided that may generate a high-frequency electromagnetic field configured to be received by an antenna of the RFID tag or another antenna. The antenna may be configured to create an inductive current from the electromagnetic field. This current may activate a circuit of the tag, which may result in transmission of electromagnetic radiation from the tag. In some embodiments, this may be accomplished by modulation of the field created by the transmission unit. The frequency of the electromagnetic radiation emitted by the tag may be distinct from the radiation emitted from the transmission unit. In this manner, it may be possible to identify and distinguish the two signals. In some embodiments, the frequency of the signal from the tag may lie within a side range of the frequency of the radiation emitted from the transmission unit. Additional details regarding RFID technology that may be useful in connection with one or more embodiments discussed herein may be found in, for example, U.S. Patent Application Publication No. 2009/0281419 titled "System for Determining the Position of a Medical Instrument," the entire contents of which are incorporated herein by specific reference.

In other embodiments, antenna 118 may comprise a Bluetooth antenna. In such embodiments, multiple corresponding Bluetooth receivers at known locations may be configured to sense signal strengths from the Bluetooth antenna 118 and triangulate such data in order to localize the signal from the Bluetooth antenna 118 and thereby locate the TD within a patient's body. Other embodiments may be configured to use angle-based, electronic localization techniques and equipment in order to locate the antenna 118. Some such embodiments may comprise use of directional antennas, which may be useful to increase the accuracy of the localization. Still other embodiments may comprise use of other types of hardware and/or signals that may be useful for localization, such as WIFI and cellular signals, for example.

One or more receiver units may be set up to receive the signal from the tag. By evaluating, for example, the strength of the signal at various receiver units, the distances from the various receiver units may be determined. By so determining such distances, a precise location of the TD relative to a patient and/or a particular organ or other surgical site on the patient may be determined. In some embodiments, a display screen with appropriate software may be coupled with the RFID or other localization technology to allow a surgeon to visualize at least an approximate location of the tag, and therefore TD, relative to the patient's body.

Some embodiments may be further configured such that data from the antenna(s) may be used in connection with sensor data from the TD. For example, some embodiments of TDs comprising one or more sensors may be further configured with one or more RFID tags or other antenna(s). As such, data from the one or more sensors may be paired or otherwise used in connection with data from the one or more antenna(s). For example, some embodiments may be configured to provide information to a surgeon regarding one or more locations on the body from which one or more sensor readings were obtained. To further illustrate using another example, information regarding tissue concentration of a particular protein and/or nucleic acid may be combined with a location from which such tissue concentration(s) were taken. In this manner, a surgeon may be provided with specific information regarding which locations within a patient's body have been adequately sampled or otherwise found to contain the concentrations referenced aboveTD.

In some such embodiments, a visual display may be provided comprising an image of the patient's body and/or one or more selected regions of a patient's body. Such a system may be configured so as to provide a visual indication for one or more regions within the image corresponding to regions of the patient's tissue that have been sufficiently analyzed. For example, a display of a patient's liver may change colors at locations on the display that correspond with regions of the liver that have been detected to contain a specified range of hepatitis virus. Such regions may, in some embodiments, be configured such that pixels corresponding to particular regions only light up after the corresponding tissue in that region reaches a particular threshold concentration.

In some embodiments tip 101 may be attached to a robotic arm. In some embodiments, tip 101 and portion of shaft 102 may be attached to a robotic arm. In some embodiments tip 101 and/or a portion of shaft 102 and/or a portion shaft and/or portion of handle 103 may be attached to a robotic arm. In some embodiments, the robotic arm may comprise one or more motors such as a screw-drive motor, gear motor, hydraulic motors, etc. In some embodiments the robotic arm system may comprise worm gearheads, video cameras, motor control circuits, monitors, remote control devices, illumination sources, tactile interface, etc.

FIGS. 1k and 1L depict alternative embodiments of a TD in which cover 180 comprises one or more openings 180k in FIGS. 1K and 180L in FIG. 1L. The remaining elements shown FIGS. 1k and 1l may be similar or identical to embodiments depicted in FIGS. 1a-1j.

As shown in FIG. 1k, at least one opening 180k is/are present in cover 180. In some embodiments, cover 180 may be configured to at least substantially seal (other than opening(s) 180k) an interior space such that a vacuum applied via port 187 may result in suction through opening 180k. In the depicted embodiment, the opening(s) 180k may have a round shape. In the depicted embodiment, openings 180k may measure about 1.5 mm in diameter. In other embodiments, openings 180k may range in diameter from about 100 microns to about 100 mm. In other contemplated embodiments, openings 180k may have a variety of geometric shapes including but not limited to square, rectangular, and/or polygonal. In the depicted embodiment, sensor 189k may comprise a nanosensor. In some embodiments, cover 180 may be configured to at least substantially seal an interior space such that a vacuum applied via port 187 may result in suction through opening(s) 180k. In the depicted embodiment, seat 188 may elevate or decline to allow sensor 189k to approach and/or move away from opening 180k in order to increase and/or decrease contact with tissues and/or fluids that may be suctioned into the space inside of cover 180 and dock 184 when suction is applied via suction port 187. Actuators, not seen in this view but discussed elsewhere in this disclosure may be configured to move seat 188 and/or sensor 189*k*. When suction is applied via suction port 187, fluids and/or tissues external to cover 180 may be forced/pulled into contact with the edges of openings 180*k* and these may be further pulled through openings 180*k* with or without gross movement of the TD. Fluids and/or tissues that were previously external to the TD may be brought into contact with sensor 189*k* for analysis. Elements within the dock and cover space, not seen in this view but discussed elsewhere in this disclosure may be configured to move, stir, and/or alter the temperature of fluids within the dock and cover space to aid in incubation and/or analysis and/or reanalysis and/or cleaning and/or maintenance. Fluid entry into cover 180 may be facilitated or prevented by several factors including but not limited to size of openings, outside environment, tissue environment, and/or positive pressure of fluids/gasses from fluid delivery port 186 and/or vacuum from fluid extraction port 187.

The shaft of FIG. 1*k* further comprises antenna 118*k*. In the depicted embodiment, 118*k* represents an antenna configured to deliver a signal to a receiver unit. In some embodiments, antenna 118*k* may comprise any of the antennas described elsewhere herein including for example any of the antennas discussed in connection with antenna 118*k*. In embodiments in which antenna 118*k* comprises an RFID tag, the RFID tag may comprise an RFID transponder.

As shown in FIG. 1L, at least one opening 180L is/are present in cover 180. In the depicted embodiment the opening(s) 180L may have a round shape. In the depicted embodiment, openings 180L may measure about 1.5 mm in diameter. In the embodiment depicted in FIG. 1L, at least a portion of sensor 189L is allowed to protrude through a portion of the TD into the space external to the TD for body tissue and/or fluid sensing and/or sampling and/or testing. In other embodiments, openings 180L may range in diameter from about 100 microns to about 100 mm. In other contemplated embodiments openings 180L may have a variety of geometric shapes including but not limited to square, rectangular, and/or polygonal. For example, a rectangular shaped opening may allow for sensors deployed on a strip to pass through the opening. Sensors 189L deployed on a strip may pass through opening(s) 180L, as shown in FIG. 1L. A strip seen from the side view may look like a line. In some embodiments, the sensors and/or the material, that said sensors are deployed upon, are flexible. Flexibility may be helpful to maintain integrity of a sensor passing through an opening (in the cover and/or TD) into the external environment with or without agitation of the TD. In the depicted embodiment, sensor 189L is a nanosensor. In some embodiments, cover 180 may be configured to at least substantially seal an interior space such that a vacuum applied via port 187 may result in suction through opening(s) 180L. In FIG. 1L at least a portion of a sensor may protrude through an opening 180L in the TD to make contact with tissues and/or fluids outside of the TD. In the depicted embodiment, seat 188 may elevate or decline to allow sensor 189L to pass through opening 180L in order to contact tissues and/or fluids outside the cover and/or dock and/or TD and/or return back into the area under the cover adjacent to the dock. Actuators, not seen in this view but discussed elsewhere in this disclosure may be configured move seat 188 and/or sensor 189L. Fluid entry into cover 180 may be facilitated or prevented by several factors including but not limited to size of openings, outside environment, tissue environment, and/or positive pressure of fluids/gasses from fluid delivery port 186 and/or vacuum from fluid extraction port 187. Sensor 189L may receive and/or send one or more signals from and/or back to a processing unit to be analyzed while deployed outside of the cover and/or once retracted back under the cover. After sensor 189L is retracted back through the cover, it may be cleaned as discussed elsewhere in this disclosure.

Sensor 189L may be coupled with an antenna, which may send and/or receive one or more signals to/from a processing unit while sensor 189L is deployed outside of cover 180. Alternatively, or additionally, data from sensor 189L resulting from tissue and/or fluid analysis using sensor 189L may be stored locally and transmitted later. For example, a signal including such analysis data may be transmitted after sensor 189L has been retracted back under cover 180. As yet another alternative, such a signal may be transmitted following surgery. In such implementations, the signals need not necessarily be transmitted wirelessly. In fact, some embodiments may be configured to store data locally, after which a data module, such as a memory stick, may be removed from the TD/TDM and uploaded to a separate computer for analysis.

After sensor 189L is retracted back into cover 180, it may be cleaned, as discussed elsewhere in this disclosure. In other embodiments, at least a portion of sensor 189L may be positioned on a flexible roll and/or may be disposable. For example, some embodiments may comprise one or more flexible nanosensors 189L positioned on a flexible roll or stack such that portions of the roll/stack may protrude from a portion of cover 180, such as through opening(s) 180L, for analysis. Once a particular tissue/fluid analysis has been performed, some embodiments may be configured to wind the roll, flip the stack, and/or discard of the used portion of sensor 189L and/or to expose a new portion of sensor 189L for further analysis. Alternatively, used portion(s) of sensor 189L may be stored with the TD/TDM and discarded elsewhere following the procedure. In other embodiments, at least a portion of a flexible nanosensor 189L, such as a nanosensor on a flexible roll, may protrude from a portion of a TD/TDM without being manually extended/retracted through openings 180L. Flexible nanosensors may be obtained/manufactured by methods available to those of ordinary skill in the art, including but not limited to: Fabrication of Nanowire Electronics on Nonconventional Substrates By Water-Assisted Transfer Printing Method (Lee, Kim, Zheng; Nano Lett, 2011, 11(8):3435-9) and Vertical Transfer of Uniform Silicon Nanowire Arrays Via Crack Formation (Weisse, Kim, Lee, Zheng; Nano Lett 2011, 11(3): 1300-1305), which is hereby incorporated by reference in its entirety.

The shaft of FIG. 1L further comprises antenna 118L. In the depicted embodiment, 118L represents an antenna configured to deliver a signal to a receiver unit. In some embodiments, antenna 118L may comprise any of the antennas described elsewhere herein including for example any of the antennas discussed in connection with antenna 118L. In embodiments in which antenna 118L comprises an RFID tag, the RFID tag may comprise an RFID transponder.

Figures 5A, 5B:
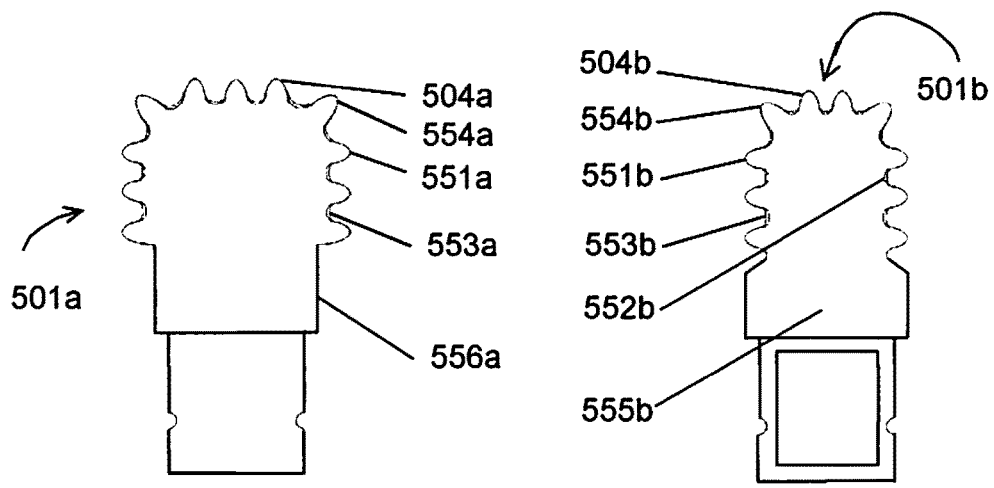
FIG. 5a is an upper plan view illustrating the protrusions and lysing segments of an embodiment of a tissue dissector, wherein some of the protrusions and lysing segments are oriented in a non-axial direction.
FIG. 5b is an upper plan view illustrating the protrusions and lysing segments of an alternative embodiment of a tissue dissector, wherein some of the protrusions and lysing segments are oriented in a non-axial direction.

With reference again to FIG. 1 *b* which is a perspective view of a break-away portion of the embodiment previously depicted in FIG. 1*a*. In the depicted embodiment, tip 101 may be made of materials that are both electrically nonconductive and of low thermal conductivity such as porcelain, epoxies, ceramics, glass-ceramics, plastics, or varieties of polytetrafluoroethylene. Alternatively, the tip may be made from metals or electroconductive materials that are completely or partially insulated. Note the relative protrusions and relative recessions are not completely visible from this viewing angle. In some embodiments, the relative recessions of the tip is the electrically conductive tissue lysing element 105 (usually hidden from view at most angles) which may have any geometric shape including a thin cylindrical wire; the electrically conductive lysing element can be in the shape of a plate or plane or wire and made of any metal or alloy that does not melt under operating conditions or give off toxic residua. Optimal materials may include but are not limited to steel, nickel, alloys, palladium, gold, tungsten, silver, copper, and platinum. Metals may become oxidized thus impeding electrical flow and function. In alternative embodiments the geometry of the tip area may comprise protrusions that are not oriented along the axis of the shaft (as seen from a top view); some of these alternative embodiments for tip area geometries are depicted in FIG. 5a, b, c, d. Some embodiments may be configured to be modular and/or comprise disposable tips such that a surgeon can place an appropriate tip for a particular surgery on the shaft. Alternatively or additionally one or more of the tips may be disposable such that a surgeon may dispose of the tip after performing surgery and install a new tip for subsequent surgeries or a continuation of the current surgery with a new tip.

An energy window 107 may be present on the upper side of the device. In some embodiments energy window 107 comprises an electrosurgically energized window. It is contemplated that in alternative embodiments, energy window 107 may be omitted. It should be noted that the term "energy window" is intended to encompass what is referred to as a planar-tissue-altering-window/zone in U.S. Pat. No. 7,494,488 and, as described later, need not be electrosurgically energized in all embodiments. In some embodiments, the "energy window" may comprise a variety of other energy emitting devices, including radiofrequency, intense pulsed light, LASER, thermal, microwave and ultrasonic. It should also be understood that the term "energy window" does not necessarily imply that energy is delivered uniformly throughout the region comprising the energy window. Instead, some energy window implementations may comprise a series of termini or other regions within which energy is delivered with interspersed regions within which no energy, or less energy, is delivered. This configuration may be useful for some implementations to allow for alteration of certain tissue areas with interspersed areas within which tissue is not altered, or at least is less altered. This may have some advantages for certain applications due to the way in which such tissue heals. A second energy window may also be included in some embodiments, and may comprise a radiofrequency electrosurgery or another variety of energy emitting device.

Electro-coagulation and/or electro-cutting energy may arrive in conduits 111 and/or 112. In some embodiments, electrocoagulation energy may travel by wiring through the handle and shaft to termini 107a, which are part of energy window 107. Electro-cutting and electro-coagulation currents may be controlled outside the TD at an electrosurgical generator, such as the Bovie Aaron 1250™ or Bovie Icon GP™. In the depicted embodiment, energy window 107 comprises an electrosurgical energy window. In the depicted embodiment, energy window 107 comprises one or more electrosurgical elements. In the depicted embodiment, energy window 107 comprises one or more hollow protruding ceramic termini 107a atop a nonconductive ceramic plate; one or more conductive metal pins pass may through the hollow termini and may be electrically connected to electrical leads which may pass through said conduits. In the depicted embodiment, the metal pins, of termini 107a, comprise surgical stainless steel pins. In an alternative embodiment, the metal pins comprise an electroconductive coating such as for example, Silverglide® coating (from Stryker, Silverglide® Surgical, Kalamazoo, Mich., USA) and/or gold and/or titanium nitride (Strem Chemicals Inc., Newburyport, Mass., USA). Such electroconductive coats may reduce carbonized debris build up and enhance electrical transmission into target tissues. In the depicted embodiment, nonconductive hollow ceramic termini 107a protrude about 2 mm above the plane of energy window 107, which is flush with the plane of tip 101 and shaft 102. In some embodiments, energy window 107 may protrude above the plane of tip 101 and/or shaft 102. In an embodiment energy window 107 may measure about 10 mm×15 mm. In some embodiments, energy window 107 may lie below the plane of tip 101 and/or shaft 102. In contemplated embodiments, nonconductive hollow ceramic termini 107a may protrude a range of about 0.5 mm-20 mm above the plane of the energy window. In the depicted embodiment, one or more holes in termini 107a measure about 1.5 mm in diameter and/or conductive pins measure 1.2 mm in diameter. In the depicted embodiments, electrocoagulation current reaches metallic pins in termini 107a of window 107 from a standard hospital electrosurgical generator. Such standard electrosurgical generators, which may be used to power an electrosurgical energy window, may include those manufactured by Bovie Medical, i.e. Model Aaron1250 and IconGP (Clearwater, Fla., USA) and/or Valleylab/Covidian Model Surgistat 2 (Boulder, Colo.) and/or Erbe Electrosurgical (Tubingen, Germany) etc. Such electrosurgical generators may have a maximal output power that may range from about 80 W to 120 W. In some implementations for electrosurgical energy window settings, said electrosurgical generators are operated on a 'Coag/Coagulation' power setting of 20-80% of maximal output while the TDM is motionless and/or moved by the surgeon. In some implementations, the TDM is moved at about 1 cm per second by the surgeon. In some implementations the electrocoagulation energy reaching electrosurgical energy window is pulsed at a rate ranging from about 20 cycle per second to 50 cycles per second. In some implementations the electrocoagulation energy reaching electrosurgical energy window is pulsed at rates ranging from about 1 cycle per second to 200 cycles per second. In some embodiments, the electrosurgically energized window current can be further pulsed at varying rates, by interpolating gating circuitry at some point external to the electrosurgical generator by standard mechanisms known in the art. In some embodiments, the electrosurgically energized window current can be further pulsed at varying rates by gating circuitry within the electrosurgical generator by standard mechanisms known in the art.

In some embodiments, the electrosurgical energy window 107 may be located on shaft 102. In alternative contemplated embodiments, the electrosurgical energy window 107 comprises an electroconductive plate with termini, encased by an electrical insulator coat except at one or more points on termini. In some embodiments termini are pressed into the electroconductive plate. In some embodiments the electroconductive plate comprises a metal plate and/or a cermet. In an embodiment, the metal plate comprises surgical stainless steel. In some embodiments, the electroconductive plate and/or termini may be directly coated with an electroconductive coating such as for example, Silverglide® coating (from Stryker, Silverglide® Surgical, Kalamazoo, Mich., USA) and/or gold and/or titanium nitride (Strem Chemicals Inc., Newburyport, Mass., USA). In some embodiments the electroconductive plate may be coated with an electrically insulating coat. In some embodiments, an electroconductive coat is placed upon the electroconductive plate before an insulating coat. In some embodiments, the electrical insulator comprises a nonconductive anti-stick polymer such as polytetrafluroethylene. In some embodiments a nonconductive coating may cover an electroconductive place ranging from about 90% coverage to 98% coverage. In other embodiments coverage may range from about 5% to about 90%. In another embodiment, the insulated electroconductive plate may be substantially planar and may comprise one or more defects in the insulating surface coating which may allow one or more exit points for electrons (electrosurgical energy). In some embodiments, the geometry of one or more of such defects is circular and/or square and/or triangular and/or geometric in shape. In some embodiments, the diameter of the geometric defect in the insulating layer covering may range from about 1 mm to about 20 mm In some embodiments, the defects may form a pattern.

In an embodiment, the tip may measure about 1 cm in width and about 1-2 mm in thickness. Sizes of about one-fifth to about five times these dimensions may also have possible uses. In some veterinary embodiments, tip sizes of about one-tenth to 20 times the aforementioned dimensions may also have possible uses. In some embodiments, the tip can be a separate piece that is secured to shaft by a variety of methods such as a snap mechanism, mating grooves, plastic sonic welding, etc. Alternatively, in some other embodiments, the tip can be integral or a continuation of shaft made of similar metal or materials. In some embodiments, the tip may also be constructed of materials that are both electrically non-conductive and of low thermal conductivity; such materials might comprise, for example, porcelain, ceramics, glass-ceramics, plastics, varieties of polytetrafluoroethylene, carbon, graphite, and graphite-fiberglass composites.

In some embodiments, the tip may be constructed of a support matrix of an insulating material (e.g., ceramic or glass material such as alumina, zirconia). Lysing segment energy conduit 111 connects to electrically conductive elements to bring RF electrosurgical energy from an electrosurgical generator down the shaft 102 to electrically conductive lysing elements 105 mounted in the recessions in between the protrusions 104. In some embodiments, the protrusions may comprise bulbous protrusions. The tip shown in this embodiment has four relative protrusions and three relative recessions and provides for a monopolar tip conductive element. All of the axes of the relative protrusions of the tip depicted in this embodiment extend at least substantially parallel to the axis of the shaft of the TD (as viewed from Top). In embodiments of tips of such axial placement of protrusions and or relative recessions, surgeons may use methods of defining and or dissecting a target area by entering through an incision and then moving the TD tip in a primarily axial direction forward and backward and reorienting the TD after the backstroke in a spokewheel pattern the TD to access tissues adjacent to earlier strokes. In some embodiments some of the protrusions and lysing segments may be oriented in a non-axial direction.

In the depicted embodiment, the tip 101 may alternatively be made partially or completely of concentrically laminated or annealed-in wafer layers of materials that may include plastics, silicon, glass, glass/ceramics, cermets or ceramics. Lysing elements 105 may also be made partially or completely of a cermet material. Alternatively, in a further embodiment the tip may be constructed of insulation covered metals or electroconductive materials. In some embodiments, the shaft may be flat, rectangular or geometric in cross-section or substantially flattened. In some embodiments, smoothing of the edges of the shaft may reduce friction on the skin surrounding the entrance wound. In some further embodiments, the shaft may be made of metal or plastic or other material with a completely occupied or hollow interior that can contain insulated wires, electrical conductors, fluid/gas pumping or suctioning conduits, fiber-optics, or insulation.

In some embodiments the shaft may have a length of about 10-20 cm. In some embodiments the handle may have a length of about 8-18 cm.

In some embodiments, shaft plastics, such as polytetrafluoroethylene may act as insulation about wire or electrically conductive elements. In some embodiments, the shaft may alternatively be made partially or completely of concentrically laminated or annealed-in wafer layers of materials that may include plastics, silicon, glass, glass/ceramics, ceramics carbon, graphite, graphite-fiberglass composites. The energy window 107 may only be substantially planar, or may take on other cross-sectional shapes that may correspond with a portion of the shape of the shaft, such as arced, stair-step, or other geometric shapes/curvatures. In the embodiments depicted in FIGS. 1a & 1b, energy window 107 is adjacent to protrusions 104, however other embodiments are contemplated in which an energy window may be positioned elsewhere on the shaft 102 or tip 101 of the wand, and still be considered adjacent to protrusions 104. However, if an energy window was placed on handle 103, such an energy window would not be considered adjacent to the protrusions 104.

Conduits may also contain electrical control wires to aid in device operation. Partially hidden from direct view in FIGS. 1a & 1b, and located in the grooves defined by protrusions 104 are electrically conductive tissue lysing elements 105, which, when powered by an electrosurgical generator, effects lysing of tissue planes on forward motion of the device. The lysing segments may be located at the termini of conductive elements. In some embodiments, one or more sensors such as for example sensors 110 and 114 may be positioned on the device. The sensors 110 and 114 may comprise any of the sensors described in the specification herein. Other embodiments may comprise one or more sensors on any other suitable location on the TD, including but not limited to on the protrusions or otherwise on the tip, and on the shaft. Sensors that may be useful include thermal sensors, photoelectric or photo optic sensors, cameras, etc. In some embodiments, one or more sensors may be used to monitor the local post passage electrical impedance or thermal conditions that may exist near the distal tip of the shaft or on the tip. Some embodiments may also comprise one or more sensors incorporating MEMS (Micro Electro-Mechanical Systems) technology, such as MEMS gyroscopes, accelerometers, and the like. Such sensors may be positioned at any number of locations on the TD, including within the handle in some embodiments. In some embodiments, sensor 114 may comprise fiberoptic elements. In an embodiment, the sensor can be configured to sense a temperature of tissue adjacent to the apparatus. The temperature sensor may alternatively be configured or sense a temperature of one or more fluids adjacent to the apparatus such as for example tissue fluids and/or fluids introduced by the surgeon.

Temperature and impedance values may be tracked on a display screen or directly linked to a microprocessor capable of signaling control electronics to alter the energy delivered to the tip when preset values are approached or exceeded. Typical instrumentation paths are widely known, such as thermal sensing thermistors, and may feed to analog amplifiers which, in turn, feed analog digital converters leading to a microprocessor. In some embodiments, internal or external ultrasound measurements may also provide information which may be incorporated into a feedback circuit. In an embodiment, an optional mid and low frequency ultrasound transducer may also be activated to transmit energy to the tip and provide additional heating and may additionally improve lysing. In some embodiments, a flashing visible light source, for example, an LED, can be mounted on the tip may show through the tissues and/or organs to identify the location of the device.

In some embodiments, one or more electromagnetic delivery elements 115 may be positioned on tip or shaft. Other embodiments may comprise one or more electromagnetic delivery elements on any other suitable location on the TD, including but not limited to on the protrusions or otherwise on the tip, and on the shaft. Electromagnetic delivery elements that may be useful include: LEDs, LASERs, fiberoptics, filaments, photoelectric materials, infrared emitters, etc.

A second energy window 108 may also be included in some embodiments, and may comprise yet another ultrasonic energy emitter or another variety of energy emitting device. An ultrasonically energized energy window 108 may be present on the upper side of the device. It is contemplated that in alternative embodiments, energy window 108 may be omitted. It should be noted that the term "energy window" is intended to encompass what is referred to as a planar-tissue-altering-window/zone in U.S. Pat. No. 7,494,488 and, as described later, need not be ultrasonically energized in all embodiments. In some embodiments, the "energy window" may comprise a variety of other energy emitting devices, including ultrasonic, intense pulsed light, LASER, thermal, microwave and electrical. It should also be understood that the term "energy window" does not necessarily imply that energy is delivered uniformly throughout the region comprising the energy window. Instead, some energy window implementations may comprise a series of energy delivering elements or other regions within which energy is delivered with interspersed regions within which no energy, or less energy, is delivered. An ultrasonic energy window configuration may be useful for some implementations, depending upon piezoelectric component and/or energy applied to less aggressively disrupt tissues (in order to possibly increase the concentration of target chemicals and/or biological compounds) at the cellular level to increase the availability of biological and/or chemical components to be sensed/analyzed and/or (may be at higher energy levels) to allow for alteration and/or damage to targeted tissues and/or heating for treatment. Energy window 108 may only be at least substantially planar, or may take on other cross-sectional shapes that may correspond with a portion of the shape of the shaft, such as arced, stair-step, or other geometric shapes/curvatures.

Some embodiments may comprise a low cost, disposable, and one-time-use device. However, in some embodiments intended for multiple uses, the tip's electrically conductive tissue lysing elements be protected or coated with materials that include, but are not limited to, Silverglide™ non-stick surgical coating, platinum, palladium, gold and rhodium. Varying the amount of protective coating allows for embodiments of varying potential for obsolescence capable of either prolonging or shortening instrument life.

In some embodiments, the electrically conductive lysing element portion of the tip may arise from a plane or plate of varying shapes derived from the aforementioned materials by methods known in the manufacturing art, including but not limited to additive manufacturing, cutting, stamping, pouring, molding, filing and sanding. In some embodiments, the electrically conductive lysing element 105 may comprise an insert attached to a conductive element in the shaft or continuous with a formed conductive element coursing all or part of the shaft. In some embodiments, a lysing segment energy conduit 111 brings RF electrosurgical energy down the shaft to electrically conductive lysing elements 105 associated in part with the recessions. In an embodiment, the electrosurgical energy via conduit 111 is predominately electro-cutting.

In some embodiments, the electrically conductive element or wiring may be bifurcated to employ hand switching if an optional finger switch is located on handle. The electrically conductive element or wiring leading from the shaft into the handle may be bundled with other leads or energy delivering cables, wiring and the like and may exit the proximal handle as insulated general wiring to various generators (including electrosurgical), central processing units, lasers and other sources as have been described herein. In some embodiments, the plate making up lysing segments 105 may be sharpened or scalloped or made to slightly extend outwardly from the tip recessions into which the plate will fit.

Alternatively, in some embodiments, since cutting or electrical current may cause an effect at a distance without direct contact, the lysing element may be recessed into the relative recessions or grooves defined by the protrusions 104 or, alternatively, may be flush with protrusions 104. In some further adjustable embodiments, locations of the electrically conductive lysing elements with respect to the protrusions may be adjusted by diminutive screws or ratchets. In some further adjustable embodiments, locations of the electrically conductive lysing elements with respect to the protrusions may be adjusted by MEMS or microelectronics. The plate, which in some embodiments is between 0.01 mm and 1 mm thick, can be sharpened to varying degrees on its forward facing surface. It is possible that plate sharpness may increase the efficiency with which electricity will pass from the edge cutting the target tissue. Sometimes, however, proper function even when variably dull or unsharpened may be unhampered since electrosurgical cutting current may cut beyond the electroconductive edge by a distance of over 1 mm. In some embodiments, the plate thickness may vary from 0.001 mm to 3 mm thick.

In some embodiments, the electrically conductive lysing element may also exist in the shape of a simple wire of 0.1 mm and 1 mm 0.01 mm to 3 mm. In some embodiments, the wire may measure between 0.01 mm to 3 mm. Such a wire may be singly or doubly insulated as was described for the plate and may have the same electrical continuities as was discussed for the planar (plate) version. In some embodiments, an electrosurgical current for the electrically conductive lysing element is of the monopolar "cutting" variety and setting and may be delivered to the tip lysing conductor in a continuous fashion or, alternatively, a pulsed fashion. The surgeon can control the presence of current by a foot pedal control of the electrosurgical generator or by button control on the shaft (forward facing button). The amount of cutting current may be modified by standard interfaces or dials on the electrosurgical generator. In some embodiments, the electrosurgically energized window current can be further pulsed at varying rates, by interpolating gating circuitry at some point external to the electrosurgical generator by standard mechanisms known in the art. In some embodiments, the electrosurgically energized window current can be further pulsed at varying rates by gating circuitry within the electrosurgical generator by standard mechanisms known in the art. For some embodiments, the electrically conductive lysing element is a monopolar tip in contact with conductive elements in the shaft leading to external surgical cable leading to an electrosurgical generator from which emanates a grounding or dispersive plate which may be placed elsewhere in contact with the patient's body, such as the thigh. Such circuitry may be controlled and gated/wired from the cutting current delivery system of the electro surgical generator. In an embodiment, the tip may also be manufactured from multilayer wafer substrates comprised of bonded conductive strips and ceramics. Suitable conductive materials include but are not limited to those already described for tip manufacture.

In alternative embodiments, the electrically conductive lysing elements may be bifurcated or divided into even numbers at the relative recessions, insulated and energized by wiring to an even number of leads in a bipolar fashion and connected to the bipolar outlets of the aforementioned electrosurgical generators. Rings partly or completely encircling the shaft of the hand unit can be linked to a partner bipolar electrode at the tip or on the energy window. Such bipolar versions may decrease the available power necessary to electrically modify certain tissues, especially thicker tissues. In alternative embodiments, the lysing elements may be divided into odd numbers yet still allow for bipolar flow between two or more elements as those of ordinary skill in the art would appreciate.

FIGS. 2a-j depict various views of a particular embodiment of a tissue dissector (TD) with a sensor dock on the upper side of the device with a movable cover.

FIG. 2a is a perspective view of an embodiment of a TD comprising a tip 201, a shaft 202 and a handle 203. Located on the shaft is dock 284 that may accommodate seat 286 which may releasably hold sensor 289. In some embodiments sensor 289 may comprise an optical sensor. In some embodiments sensor 289 may comprise an optical biosensor. In some embodiments sensor 289 may comprise a fiberoptic.

In the depicted embodiment, sensor 289 comprises a fiberoptic element(s) positioned in an optics-seat. However, in other embodiments, sensor 289 may be positioned in seat 288 without an optics-seat. In the depicted embodiment sensor 289 comprise a fiberoptic biosensor. In the depicted embodiment, the fiberoptics may protrude from a fiberoptic-seat. In other contemplated embodiments fiberoptics may be flush with or recessed from an adjacent and/or surface in which they are bound. Optical sensors may be obtained/manufactured by methods available to those of ordinary skill in the art, including but not limited to: Toward a Highly Specific DNA Biosensor: PNA-modified Suspended-core Photonic Crystal Fibers (Coscelli, Sozzi, et. al. IEEE J. Sel Top. Quantum Electron 2010, 16, 967-972.) and/or Suspended Nanowires: Fabrication, Design, and Characterization of Fibers with Nanoscale Cores (Ebendorff, Warren, Manro; Opt Express 2009, 17, 2646-2657.) and/or Fiber Optic Sensors, Fundamentals and Applications (Krohn; 2000 ISA, Research Triangle Park, N.C.) and/or Handbook of Optical Fibre Sensing Technology (Lopez-Higuera; 2001; John Wiley & Sons, Chichester, UK 2001). and/or Recent Advances in Fiber-Optic DNA Biosensors (Wang, Pang, Zhang; J. Biomedical Science and Engineering, 2009, 2, 312-317.) and/or Studies on the Fluorescence Fiber-Optic DNA Biosensor Using p-Hdroxyphenylimidazol1,10-phenanthroline Ferrum(III) as Indicator (Niu, Wang, et al; J Fluoresc, 18, 227-235.) and/or Thiazole Orange-Conjugated Peptide Nucleic Acid For Detection of Target Nucleic Acid In Homogenous Solution (Svanik, Westman, et al.; Anal. Biochem 2000; 281(1), 26-35.) and/or (Lin, Tsai, et. al; Applied Optics 2007; 46(5), 800-806.) and/or Molecular Beacons Immobilized Within Suspended Core Optical fiber for Specific DNA Detection (Nguyen, Warren-Smith, et. al.; Optics Express, 31 Dec. 2012, Vol. 20, No. 28.) and/or Microgap Structure Optical Sensors for Fast Label-Free DNA Detection (Wang, Cooper, Wang; J. Lightwave Technol 2008; 26(17), 3181-3185.) and/or Fiber Optic Microarrays (Walt; Chem. Soc. Rev. 2009; 39(1) 38-50.) and/or Sensing with Suspended-Core Optical fibers (Monro, Warren-Smith, et. al.; Opt Fiber Technol 2010 16(6), 343-356.) and/or Antibody Immobilization Within Glass Microstructured Fibers: A Route to Sensitive and Selective Biosensors (Ruan, Foo, et. al.; Opt. Express 2008; 16(22) 18514-18523.) and/or Optical Fibre-Based Detection of DNA Hybridization (Hine, Chen, et. al.; Biochem. Soc. Trans (2009)37, 445-449.) and/or Nanostructure Waveguide Based Surface Plasmon Resonance Sensor (Yu, Zhang, Wang, Shum; SimTech 2010; STR_V11-N1_09_PMG, 42-45.) and/or Studies on the Flourescence Fiber-Optic DNA Biosensor Using p-Hydroxyphenylimidazo[f]1,10-phenanthroline Ferrum(III) as Indicator (Shu-yan Niu et. al.; J Flouresc (2008) 18:227-235.) and/or Optical DNA-Sensor Chip for Real-Time Detection of Hybridization Events (Peter, et al.; Fresenius' Journal of Analytical Chemistry, 2001. 371(2): p. 120-127.) and/or Applicability of a Noncooled Video-Rated CCD camera for Detection of Flourescence In Situ Hybridization Signals (Vrolijk, et al.; Cytometry, 1994. 15(1): p. 2-11.)

For example, some of the reagents and/or chemicals and/or biochemicals that may be present in and/or delivered to and/or removed from the dock area to facilitate sensor use and/or cleaning, etc., may include but not be limited to ethanolic solutions, thiols, SDS (sodium dodecyl sulfate), water, argon gas, sodium chloride, sodium bicarbonate buffer, EGTA (ethylene glycol tetraacetic acid), EDTA (ethylenediaminetetraacetic acid), sulfo-NHS diazirine (sulfo-SDA), PBS (phosphate buffered saline), and/or Tween®-20 (PBST), etc. Such reagents and/or chemicals and/or biochemical and their acquisition and use are available to those of ordinary skill in the art, including but not limited to: Detection of Methicillin-Resistant Staphylococcus aureus (MRSA) using the NanoLantern Biosensor (STROHSAHL, MILLER, KRAUSS; Proc. of SPIE, Vol 7167OS pp. 1-12.); U.S. Pat. No. 6,593,093 B1 titled "Detection of Group A Streptococcus"; U.S. Patent Application Publication No. 2009/0186774 A1 titled "Sepsis Detection Microarray"; European Patent 2526427 A2, titled "Rapid Pathogen Diagnostic Device and Method"; all of which are hereby incorporated herein by reference in their entirety.

Returning to FIG. 2a (a perspective view of an embodiment of a TD comprising a tip 201, a shaft 202 and a handle 203. Located on the shaft is dock 284 that may accommodate seat 288 which may releasably hold sensor 289. In some embodiments sensor 289 may comprise a optical sensor. In some embodiments, dock 284 may be recessed into shaft 202 and/or tip 201. In some embodiments dock 284 may protrude from shaft 202 and/or tip 201. In some embodiments dock 284 may be flush with shaft 202 and/or tip 201. In some embodiments, sensor 289 may comprise a fiberoptic sensor. In some embodiments the sensor 189 may comprise a biological optical sensor. In some embodiments, seat 288 may be fixed in position. In some embodiments, seat 288 may be moveable. In some embodiments sensor 284 may be fixed in seat 288. In some embodiments, the sensor 289 may be detachable seat 288. It is contemplated that in alternative embodiments, seat 288 may be omitted. In some embodiments the dock may comprise cover moving means and/or a cover tip. Cover tip 281 and means for selectively moving a cover 283 may be positioned adjacent dock 284. Examples of such cover moving means may include rails, grooves, tracks, ratchets, cables, arms, lines, etc. In the depicted embodiment the cover moving means comprises a rail. In some embodiments a portion of the shaft may comprise cover moving means 283. It is contemplated that in alternative embodiments, cover moving means 283 may be omitted. Dock 284 may comprise one or more dock wall(s) 285. Dock wall 285 may comprise fluid delivery port 286 for fluid delivery conduit. Dock wall 285 may comprise fluid extraction port 287 for fluid extraction conduit. In some embodiments, dock wall 285 may comprise one or more ports 286 and/or 287. In FIG. 1c, cover 280 is moveable along cover moving means 283 and may be opened or closed via internal control wires. In some embodiments the cover may be moved by motors. Rear end of cover 282 may be fixed to cover 280. In some embodiments, rear end of cover 282 is not fixed to cover and is itself attached to another portion of the TD. In some embodiments, dock 284 and/or dock wall 285 may accommodate a temperature modification means 295 for modifying a temperature within the dock 284 and cover 280. Temperature modification means 295 may comprise, for example a heater, a Peltier cooler, a heat pump, etc. Temperature modification means 295 may be used to heat fluids introduced by way of port 286. Temperature modification means 295 may alternatively be used to heat tissues and/or other fluids such as body tissues and/or fluids captured during a procedure using the TD. In some embodiments temperature modification means 295 may facilitate and/or inhibit certain chemical reactions and/or bond alterations that may be needed in order to sense certain biomaterials using sensor 289. In some embodiments, dock 284 and/or dock wall 285 may accommodate mixing element 296. In some embodiments temperature modification means 295 may comprise an electrical resistance heater. In contemplated embodiments, heater 295 may comprise a thin film resistor and/or piezoelectric heating device and/or other device capable of heating fluids. In some embodiments, mixing element 296 may comprise a propeller driven by an electric motor. In some embodiments, mixing element 296 may comprise one or more flaps of relatively inert flexible polymeric plastic on a post spun by an electric motor. Examples of other materials for such a flap may include polymers, metals, ceramics, etc. In another embodiment, mixing element 296 may comprise an unattached stirring rod spun by oscillating magnet. In a contemplated embodiment, a separate set of ports may originate and terminate in dock 284, and may be connected by conduit which is fluidly coupled with a piezoelectric pump and/or another fluidic motor and/or another fluidic driving device. In embodiments including one or more such additional ports, such port(s) may be positioned at an opposite end of dock 284 such that delivery of fluid(s) and/or application of a vacuum may be applied more evenly throughout dock 284. It is contemplated that in alternative embodiments, temperature modification means 295 and/or mixing element 296 may be omitted. One or more sensors 278 and/or 279 may be located on dock 284. In some embodiments, one or more sensors 278 and/or 279 may be located on dock wall 285 and/or cover 280. Sensors 278 and/or 279 may comprise any of the specific examples of sensors discussed in connection with sensors 210 and/or 214. Sensor(s) 278 and/or 279 may report conditions and/or changing conditions in dock area 184 in and/or around optical sensor 289.

In some embodiments, sensor 278 and or sensor 279 may comprise a camera. In some embodiments, sensor 278 and or sensor 279 may comprise a fiberoptic and/or fiberoptic camera and/or CCD camera and/or other camera.

In some embodiments, one or more electromagnetic delivery elements 277 may be positioned on dock 284 tip and/or cover 280 and/or tip of cover 281. Other embodiments may comprise one or more electromagnetic delivery elements on any other suitable location on the TD, including but not limited to on the sensor 289 or otherwise on seat 288. Electromagnetic delivery elements that may be useful include but are not limited to: LEDs, LASERs, fiberoptics, filaments, photoelectric materials, infrared emitters, etc. In some implementations, emission of such electromagnetic energy may be absorbed by a chemical and/or biomolecule on the sensor and/or dock area and/or reflectance and/or emission spectra of the chemical and/or biomolecule and/or a further product may be detected via sensors 278 and/or 279. In an embodiment, cover 280 and/or dock 284 may be configured to reflect electromagnetic radiation. Reflecting electromagnetic radiation and/or having mirror-like properties may allow for detection of electromagnetic radiation by sensors 278 and/or 279. In some embodiments, cover 280 and/or dock 284 comprise a thin film coating over a substrate. In some embodiments, the substrate may be plastics and/or molded polymer and/or crystal and/or glass and/or metal, etc. In some embodiments, cover 280 and/or dock 284 comprise a coating of aluminum. In some embodiments the aluminum coating comprises a protected aluminum and/or enhanced aluminum and/or UV-enhanced aluminum (a maker may be Edmund Optics, Barrington, N.J., USA).

In the depicted embodiment cover 280 may comprise plastic. In other embodiments cover 280 may comprise materials including but not limited to: polymers, quartz, glass, carbon based materials, silicates and/or metals.

The conduit may also contain electrical control wires to aid in device operation. Partially hidden from direct view in FIGS. 2a & 2b, and located in the grooves defined by protrusions 204 are electrically conductive tissue lysing elements 205, which, when powered by an electrosurgical generator, effects lysing of tissue planes on forward motion of the device. The lysing segments may be located at the termini of conductive elements. In some embodiments, one or more sensors such as for example sensors 210 and 214 may be positioned on the device. The sensors 210 and 214 may comprise any of the sensors described in the specification herein. In some embodiments, sensor 210 and or sensor 214 may comprise a camera. In some embodiments, sensor 210 and or sensor 214 may comprise a fiberoptic and/or fiberoptic camera and/or CCD camera and/or other camera. Other embodiments may comprise one or more sensors on any other suitable location on the TD, including but not limited to on the protrusions or otherwise on the tip, and on the shaft. Sensors that may be useful include thermal sensors, photoelectric or photo optic sensors, cameras, etc. In some embodiments, one or more sensors may be used to monitor the local post passage electrical impedance or thermal conditions that may exist near the distal tip of the shaft or on the tip. Some embodiments may also comprise one or more sensors incorporating MEMS (Micro Electro-Mechanical Systems) technology, such as MEMS gyroscopes, accelerometers, and the like. Such sensors may be positioned at any number of locations on the TD, including within the handle in some embodiments. In some embodiments, sensor 214 may comprise fiberoptic elements. In an embodiment, the sensor can be configured to sense a temperature of tissue adjacent to the apparatus. The temperature sensor may alternatively be configured or sense a temperature of one or more fluids adjacent to the apparatus such as for example tissue fluids and/or fluids introduced by the surgeon.

Temperature and impedance values may be tracked on a display screen or directly linked to a microprocessor capable of signaling control electronics to alter the energy delivered to the tip when preset values are approached or exceeded. Typical instrumentation paths are widely known, such as thermal sensing thermistors, and may feed to analog amplifiers which, in turn, feed analog digital converters leading to a microprocessor. In some embodiments, internal or external ultrasound measurements may also provide information which may be incorporated into a feedback circuit. In an embodiment, an optional mid and low frequency ultrasound transducer may also be activated to transmit energy to the tip and provide additional heating and may additionally improve lysing. In some embodiments, a flashing visible light source, for example, an LED, can be mounted on the tip may show through the tissues and/or organs to identify the location of the device.

In some embodiments, one or more electromagnetic delivery elements 215 may be positioned on tip or shaft. Other embodiments may comprise one or more electromagnetic delivery elements on any other suitable location on the TD, including but not limited to on the protrusions or otherwise on the tip, and on the shaft. Electromagnetic delivery elements that may be useful include: LEDs, LASERs, fiberoptics, filaments, photoelectric materials, infrared emitters, etc.

As shown in FIG. 2a, handle 203 may comprise one or more ports through which various conduits may be passed. In some such embodiments, a plurality of conduits may be bundled together for convenience if desired. For example, in the depicted embodiment, an energy delivery conduit bundle 298 may be provided, which may comprise a lysing segment energy conduit 211 and an energy window conduit 212. In addition, a miscellaneous conduit bundle 299 may be provided. Miscellaneous conduit bundle 299 may comprise, for example, various other conduits, such as conduits for one or more sensors, such as sensors 210 and 214, one or more electromagnetic delivery elements 215, fluid delivery port(s) 216, and/or suction/vacuum ports 217. In addition, miscellaneous conduit bundle 299 may comprise one or more additional conduits, such as one or more additional fluid delivery conduits for delivering a fluid, such as a liquid or gas, to port 286 in dock 284 in the TD. Miscellaneous conduit bundle 299 may further comprise one or more fluid extraction conduits (from port 287 in dock 284) for extracting of fluid to direct the fluid (again, a liquid or gas) to a remote fluid/chemical sensor.

The fluid delivery conduit (leading to port 286) may be configured to deliver, for example, buffers, cleansers, quenching agents, reagents, biological compounds, inert compounds, gases. Fluids delivered (by way of a fluid delivery conduit leading to port 286) may be energized, such as heated, ultrasonically energized, may contain detergents, antibodies, drugs, etc.

Fluid extraction conduits (leading from port 287) may not only be used to withdraw fluids to be discarded from the body, but also may be used in a wash circuit to remove fluids introduced by way of fluid delivery conduit leading to port 286 that are used to, for example, wash and/or disinfect certain tissues and/or components of the TD. Fluid extraction conduit (leading from port 287) may also be used to extract fluids for external analysis. Some embodiments may be configured to provide a bubble between separate sets of fluids to allow a user to distinguish between various fluid streams delivered using fluid extraction conduit leading from port 287.

In some embodiments, a vibration means 270 may be positioned in the handle. Other embodiments may comprise one or more vibration means on any other suitable location on the TD, including but not limited to on the protrusions or otherwise on the tip, and on the shaft. Examples of suitable vibration means may include piezoelectric materials, ultrasonic motors with stators, piezoelectric actuators, vibration motor such as an off-center weight mounted on a gear, etc. Some vibration means may be configured to emit ultrasound in the 20-40 kHz range. Yet other vibration means may include electromagnet drivers with a frequency of operation in the range of 150-400 Hz. In some embodiments, one or more vibration means may be used to provide additional forces which may facilitate passage of the TD. In some embodiments, one or more vibration means may be used to reduce debris on the electrosurgical or other components of the TD. In a further embodiment, a vibration means may be directly or indirectly connected to one or more of the lysing segments. Some vibration means may help to decrease and/or remove debris. In some embodiments use of a vibration means may, also or alternatively, be used to assist in migrating the TD through tissue during the procedure. In some such embodiments, it is thought that use of a vibration means having a lower frequency may be particularly useful for assisting in such migration. In addition, positioning the vibration means closer to a handle of the TD may facilitate such migration as well. By contrast, positioning the vibration means on or near the tip, and/or using a higher frequency vibrations means may be particularly useful for preventing buildup of debris on the tip.

FIG. 2 d, c depict the TD with cover 280 moved proximally to expose dock.

FIG. 2 f, e depict the TD with cover 280 moved distally to close over and/or seal dock.

FIG. 2g is cross sectional view of an embodiment of cover 280 comprising a groove 291 and projection 292 as described herein. Groove 292 may be used to direct fluids within cover 280 to facilitate mixing of fluids and/or directing fluids to locations in need of cleaning and/or directing fluids to sensor locations and/or bringing fluids of with a temperature range to locations within the dock or cover. Similarly as described herein, projection 292 may also be used to direct fluids to one or more desired locations and/or agitate fluids in a desired manner for a particular use.

FIG. 2h is cross sectional view of an embodiment of dock 284 comprising a groove 293 and a projection 294 as described herein. Groove 293 may be used to direct fluids within dock 284 to facilitate mixing of fluids and/or directing fluids to locations in need of cleaning and/or directing fluids to sensor locations and/or bringing fluids of with a temperature range to locations within the dock or cover. Similarly as described herein, projection 294 may also be used to direct fluids to one or more desired locations and/or agitate fluids in a desired manner for a particular use. In some embodiments, cover 280 and dock 284 may when cover 280 is in a closed position, define a common space. In some embodiments, cover grooves 291 may operate in conjunction with dock grooves 293 or dock protrusions 294 to impact fluid behavior in a desired manner.

In FIGS. 2g and/or 2h, one or more grooves 291 and 293 may be provided for example in dock 284 and/or in an interior surface of cover 280 in order to direct fluids delivered through port 286 are directed to desired to one or more desired locations. In some embodiments grooves may be configured to facilitate mixing of fluids and/or directing fluids to locations in need of cleaning and/or directing fluids to sensor locations. One or more projections 292 and 294 may be provided for example in dock 284 and/or in an interior surface of cover 280 in order to direct fluids delivered through port 286 are directed to desired to one or more desired locations. In some embodiments projections may be configured to facilitate mixing of fluids and/or directing fluids to locations in need of cleaning and/or directing fluids to sensor locations. In some embodiments multiple projections may define a groove, in other embodiments one or more grooves may be formed within a surface of a cover and/or dock.

With the cover 280 closed, as depicted in FIG. 2e, fluids may be circulated within the space enclosed by cover 280 which may facilitate cleaning. Closing cover 280 may also facilitate isolation of biological tissues and/or fluids. For example, closure of cover 280 may allow for analysis of tosses and/or fluids while preventing contamination by other such tissues and fluids after a sample has been taken. Cleaning may be further facilitated by positioning of the seat and/or sensors at an angle and/or various angles. The configuration depicted in FIG. 1i may be primarily for facilitating capture to tissue and/or fluids for analysis, however some embodiments may be configured to tilt seat 288 toward a rear portion of the TD such that it faces (tilts toward) fluid port 286 to facilitate cleaning of sensor 289.

Fluid delivery port 286 for fluid delivery and fluid extraction port 287 for fluid extraction may also serve to deliver and/or remove fluids, for example, including but not limited to reagents and/or analyte(s) and/or eluent(s) and/or eluate(s). In some embodiments, fluid delivery from fluid delivery port 286 and/or fluid extraction from fluid extraction port 287 may be linked in a circuit with a pump and/or additional conduit (that is coupled with one or both of the conduits coupled with fluid delivery port 286 and fluid extraction port 287) to recirculate and/or heat and/or incubate and/or mix and/or add reagents and/or remove reagents and/or other materials from the space within the cover 280 and/or dock 284. In some embodiments, a pump external to the TD, fluidly connected to the circuit between the conduits connecting ports 287 and 286, may be used to move fluids. The available space for fluids between the cover 280 and dock 284 (with space occupying elements) may be derived by measuring an amount of fluid entering and/or exiting from ports 286 and/or 287 via their conduits. Such measurements may be compared with CAD (Computer Aided Design) calculations of the space.

FIG. 2i is a side (break away) side view, of the embodiment previously depicted in FIG. 2a of a TD, illustrating an example of positioning and/or protruding a seat (containing an optical sensor) that may allow for some exposure to passing tissues or fluids. The TD may comprise an actuator 290. In some embodiments, actuator 290 may comprise a motor. In some embodiments actuator 290, may comprise one or more such motors such as a screw-drive motor, gear motor, hydraulic motors etc. In some embodiments actuator 290 may comprise worm gearheads, motor control circuits, monitors, remote control devices, etc. In some embodiments, actuator 290 may be controlled or moved by wire and/or spring. In some embodiments, actuator may be controlled or moved by wire using manual work. In some embodiments actuator 290 may be omitted. In some embodiments, seat 288 may be configured to be manually actuated or tilted. In some embodiments, seat 288 may be configured to be positioned in affixed number of angles relative to shaft 202 and/or dock. In other embodiments, seat 288 may be configured to be repositioned in an infinite number of angled positions relative to shaft 202 and/or dock.

Means for delivering ultrasonic energy 297 may be located in/on in/on dock wall 285 of dock 284. Ultrasonic means 297 may be configured to for example, heat fluids: aid in the cleaning of one or more portions of the TD including for example dock 284: aid in the mixing of reagents and/or organic chemicals and/or biomolecules; aid in the fixation of biomolecules and/or other substances to receptors and/or sensors; aid in the removal of biomolecules and/or other substances to receptors. In the depicted embodiment the ultrasonic means comprises a piezoelectric ceramic. In some embodiments the piezoelectric ceramic may measure about 2 mm×2 mm×4 mm. It is contemplated that in alternative embodiments, ultrasonic means 297 may be omitted. In some embodiments the piezoelectric ceramic is made from lead zirconate titanate piezoelectric ceramic (which may be sold as PZT8 or PZT4 by Micromechatronics, State College, Pa.) and may be driven by 2-5 Watts at 10-20 Volts and/or may be configured to vibrate at a frequency of 300-500 kiloHertz. In some embodiments the piezoelectric may comprise quartz and/or barium titanate and/or film polymer polyvinylidene fluoride. In some embodiments the ultrasonic means measures between 1 mm and 20 mm in any dimension. Some embodiments may comprise a plurality of ultrasonic means. In some embodiments, ultrasonic means may be configured to be positioned on two or more intersecting surfaces, for example in the embodiment depicted in FIG. 2b a portion of ultrasonic means 297 is positioned on an upper surface of shaft 202 and a second portion of ultrasonic means 297 is positioned along dock wall 285 which intersects the upper surface of shaft 202. in the depicted embodiment wall 285 intersects the top surface of shaft 202 at a substantially perpendicular angle.

In the embodiment depicted in FIG. 2i, positioning the seat 288 and/or sensors 289 at one or more angles while the cover is in the open position may allow sensor(s) 289 to increase and/or alter contact and/or friction to facilitate a desired reaction between sensor 289 passing tissues and/or fluids.

In the embodiment depicted in FIG. 2j, positioning the seat 288 and/or sensors 289 at least at a substantially parallel angle with shaft 202 may be desirable or at least suitable for some applications.

In some embodiments, one or more suction/vacuum ports 217 may be provided on or about the tip or distal shaft. The port(s) may be fluidly coupled with a vacuum; the vacuum may comprise a pump or a negative pressure chamber or a syringe at the end of a fluid conduit. Other embodiments may comprise one or more suction/vacuum ports on any other suitable location on the TD, including but not limited to on the protrusions or otherwise on the tip, and on the shaft. In some embodiments, a fluid delivery port 216 may be provided. In some embodiments the fluid delivery port may be coupled with a pump or high pressure fluid. In some embodiments the port may be perpetually open such that fluid may be delivered therethrough upon actuation of a pump or fluid pressure system. In other embodiments the port may be closed and selectively opened to deliver fluid therethrough. Other embodiments may comprise one or more fluid ports on any other suitable location on the TD, including but not limited to on the protrusions or otherwise on the tip, and on the shaft. Fluid ports that may be useful may comprise channels within the TD, polymer lines, hoses, etc. Fluids that may emanate from the outlet may comprise ionic fluids such as saline, medicines (including but not limited to antibiotics, anesthetics, antineoplastic agents, bacteriostatic agents, etc.), non-ionic fluids, and or gasses (including but not limited to nitrogen, argon, air, etc.). In some embodiments fluids may be under higher pressures or sprayed. It should be understood that although these elements (216 & 217) are not depicted in every one of the other figures, any of the embodiments described herein may include one or more such elements.

In the depicted embodiment, 218 represents an antenna, such as an RFID TAG or Bluetooth antenna configured to deliver a signal to a receiver unit. In embodiments in which antenna 218 comprises an RFID TAG, the RFID tag may comprise an RFID transponder. In other embodiments the RFID tag may comprise a passive tag. It should be understood that antenna 218 is not depicted in every one of the other figures, any of the embodiments described herein may comprise one or more such elements. Other embodiments may comprise one or more antenna(s) on any other suitable location on the TD, including but not limited to on the protrusions or otherwise on the tip, and on the shaft. In embodiments wherein antenna(s) 218 comprises an RFID transponder such transponder may comprise a microchip, such as a microchip having a rewritable memory. In some embodiments, the tag may measure less than a few millimeters. In some embodiments a reader may generate an alternating electromagnetic field which activates the antenna, such as an RFID transponder, and data may be sent via frequency modulation. In embodiments comprising one or more RFID tags (or other antenna) the position(s) of the RFID tag(s) or other antenna may be determined by an alternating electromagnetic field in the ultra-high frequency range. The position may be related to a 3 dimensional mapping of the subject. In an embodiment the reader may generate an alternating electromagnetic field. In some such embodiments, the alternating electromagnetic field may be in the shortwave (13.56 MHz) or UHF (865-869 MHz) frequency. Examples of potentially useful systems and methods for mapping/tracking a surgical instrument in relation to a patient's body may be found in U.S. Patent Application Publication No. 2007/0225550 titled "System and Method for 3-D Tracking of Surgical Instrument in Relation to Patient Body, which is hereby incorporated by reference in its entirety.

In some embodiments, a transmission unit may be provided that may generate a high-frequency electromagnetic field configured to be received by an antenna of the RFID tag or another antenna. The antenna may be configured to create an inductive current from the electromagnetic field. This current may activate a circuit of the tag, which may result in transmission of electromagnetic radiation from the tag. In some embodiments, this may be accomplished by modulation of the field created by the transmission unit. The frequency of the electromagnetic radiation emitted by the tag may be distinct from the radiation emitted from the transmission unit. In this manner, it may be possible to identify and distinguish the two signals. In some embodiments, the frequency of the signal from the tag may lie within a side range of the frequency of the radiation emitted from the transmission unit. Additional details regarding RFID technology that may be useful in connection with one or more embodiments discussed herein may be found in, for example, U.S. Patent Application Publication No. 2009/0281419 titled "System for Determining the Position of a Medical Instrument," the entire contents of which are incorporated herein by specific reference.

In other embodiments, antenna 218 may comprise a Bluetooth antenna. In such embodiments, multiple corresponding Bluetooth receivers at known locations may be configured to sense signal strengths from the Bluetooth antenna 218 and triangulate such data in order to localize the signal from the Bluetooth antenna 218 and thereby locate the TD within a patient's body. Other embodiments may be configured to use angle-based, electronic localization techniques and equipment in order to locate the antenna 218. Some such embodiments may comprise use of directional antennas, which may be useful to increase the accuracy of the localization. Still other embodiments may comprise use of other types of hardware and/or signals that may be useful for localization, such as WIFI and cellular signals, for example.

One or more receiver units may be set up to receive the signal from the tag. By evaluating, for example, the strength of the signal at various receiver units, the distances from the various receiver units may be determined. By so determining such distances, a precise location of the TD relative to a patient and/or a particular organ or other surgical site on the patient may be determined. In some embodiments, a display screen with appropriate software may be coupled with the RFID or other localization technology to allow a surgeon to visualize at least an approximate location of the tag, and therefore TD, relative to the patient's body.

Some embodiments may be further configured such that data from the antenna(s) may be used in connection with sensor data from the TD. For example, some embodiments of TDs comprising one or more sensors may be further configured with one or more RFID tags or other antenna(s). As such, data from the one or more sensors may be paired or otherwise used in connection with data from the one or more antenna(s). For example, some embodiments may be configured to provide information to a surgeon regarding one or more locations on the body from which one or more sensor readings were obtained. To further illustrate using another example, information regarding tissue concentration of a particular protein and/or nucleic acid may be combined with a location from which such tissue concentration(s) were taken. In this manner, a surgeon may be provided with specific information regarding which locations within a patient's body have been adequately sampled or otherwise found to contain the concentrations referenced aboveTD.

In some such embodiments, a visual display may be provided comprising an image of the patient's body and/or one or more selected regions of a patient's body. Such a system may be configured so as to provide a visual indication for one or more regions within the image corresponding to regions of the patient's tissue that have been sufficiently analyzed. For example, a display of a patient's liver may change colors at locations on the display that correspond with regions of the liver that have been detected to contain a specified range of hepatitis virus. Such regions may, in some embodiments, be configured such that pixels corresponding to particular regions only light up after the corresponding tissue in that region reaches a particular threshold concentration.

In some embodiments tip 201 may be attached to a robotic arm. In some embodiments, tip 201 and portion of shaft 202 may be attached to a robotic arm. In some embodiments tip 201 and/or a portion of shaft 202 and/or a portion shaft and/or portion of handle 203 may be attached to a robotic arm. In some embodiments, the robotic arm may comprise one or more motors such as a screw-drive motor, gear motor, hydraulic motors, etc. In some embodiments the robotic arm system may comprise worm gearheads, video cameras, motor control circuits, monitors, remote control devices, illumination sources, tactile interface, etc.

Figure 2L:
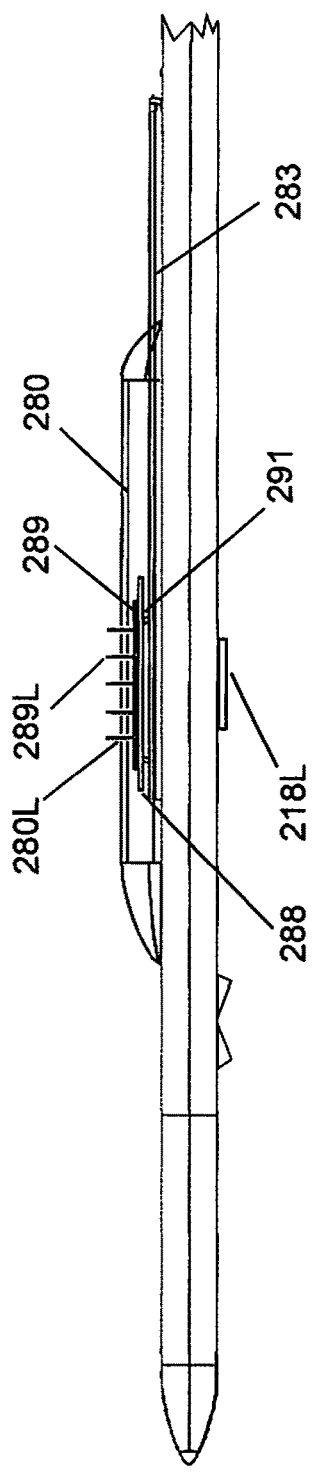
FIG. 2L is a side view of an alternative embodiment of a TD, in which the cover comprises openings and a portion of the sensor protrudes through the openings.

FIGS. 2k and 2L depict alternative embodiments of a TD in which cover 280 comprises one or more openings 280k in FIGS. 2K and 280L in FIG. 2L. The remaining elements shown FIGS. 2k and 2l may be similar or identical to embodiments depicted in FIGS. 1a-1j.

As shown in FIG. 2k, at least one opening 280k is/are present in cover 280. In some embodiments, cover 280 may be configured to at least substantially seal (other than opening(s) 280k) an interior space such that a vacuum applied via port 287 may result in suction through opening 280k. In the depicted embodiment, the opening(s) 280k may have a round shape. In the depicted embodiment, openings 280k may measure about 1.5 mm in diameter. In other embodiments, openings 280k may range in diameter from about 100 microns to about 100 mm. In other contemplated embodiments, openings 280k may have a variety of geometric shapes including but not limited to square, rectangular, and/or polygonal. In the depicted embodiment, sensor 289k may comprise a optical sensor. In some embodiments, cover 280 may be configured to at least substantially seal an interior space such that a vacuum applied via port 287 may result in suction through opening(s) 280k. In the depicted embodiment, seat 288 may elevate or decline to allow sensor 289k to approach and/or move away from opening 280k in order to increase and/or decrease contact with tissues and/or fluids that may be suctioned into the space inside of cover 280 and dock 284 when suction is applied via suction port 287. Actuators, not seen in this view but discussed elsewhere in this disclosure may be configured to move seat 288 and/or sensor 289k. When suction is applied via suction port 287, fluids and/or tissues external to cover 280 may be forced/pulled into contact with the edges of openings 280k and these may be further pulled through openings 280k with or without gross movement of the TD. Fluids and/or tissues that were previously external to the TD may be brought into contact with sensor 289k for analysis. Elements within the dock and cover space, not seen in this view but discussed elsewhere in this disclosure may be configured to move, stir, and/or alter the temperature of fluids within the dock and cover space to aid in incubation and/or analysis and/or reanalysis and/or cleaning and/or maintenance. Fluid entry into cover 280 may be facilitated or prevented by several factors including but not limited to size of openings, outside environment, tissue environment, and/or positive pressure of fluids/gasses from fluid delivery port 286 and/or vacuum from fluid extraction port 287.

The shaft of FIG. 2k further comprises antenna 218k. In the depicted embodiment, 218k represents an antenna configured to deliver a signal to a receiver unit. In some embodiments, antenna 218k may comprise any of the antennas described elsewhere herein including for example any of the antennas discussed in connection with antenna 218k. In embodiments in which antenna 218k comprises an RFID tag, the RFID tag may comprise an RFID transponder.

As shown in FIG. 2L, at least one opening 280L is/are present in cover 280. In the depicted embodiment the opening(s) 280L may have a round shape. In the depicted embodiment, openings 280L may measure about 1.5 mm in diameter. In the embodiment depicted in FIG. 2L, at least a portion of sensor 289L is allowed to protrude through a portion of the TD into the space external to the TD for body tissue and/or fluid sensing and/or sampling and/or testing. In other embodiments, openings 280L may range in diameter from about 100 microns to about 100 mm. In other contemplated embodiments openings 280L may have a variety of geometric shapes including but not limited to square, rectangular, and/or polygonal. For example, a rectangular shaped opening may allow for sensors deployed on a strip to pass through the opening. Sensors 289L deployed on a strip may pass through opening(s) 280L, as shown in FIG. 2L. A strip seen from the side view may look like a line. In some embodiments, the sensors and/or the material, that said sensors are deployed upon, are flexible. Flexibility may be helpful to maintain integrity of a sensor passing through an opening (in the cover and/or TD) into the external environment with or without agitation of the TD. In the depicted embodiment, sensor 289L is an optical sensor. In some embodiments, cover 280 may be configured to at least substantially seal an interior space such that a vacuum applied via port 287 may result in suction through opening(s) 280L. In FIG. 2L at least a portion of a sensor may protrude through an opening 280L in the TD to make contact with tissues and/or fluids outside of the TD. In the depicted embodiment, seat 288 may elevate or decline to allow sensor 289L to pass through opening 280L in order to contact tissues and/or fluids outside the cover and/or dock and/or TD and/or return back into the area under the cover adjacent to the dock. Actuators, not seen in this view but discussed elsewhere in this disclosure may be configured move seat 288 and/or sensor 289L. Fluid entry into cover 280 may be facilitated or prevented by several factors including but not limited to size of openings, outside environment, tissue environment, and/or positive pressure of fluids/gasses from fluid delivery port 286 and/or vacuum from fluid extraction port 287. Sensor 289L may receive and/or send one or more signals from and/or back to a processing unit to be analyzed while deployed outside of the cover and/or once retracted back under the cover. After sensor 289L is retracted back through the cover, it may be cleaned as discussed elsewhere in this disclosure.

Sensor 289L may be coupled with an antenna, which may send and/or receive one or more signals to/from a processing unit while sensor 289L is deployed outside of cover 280. Alternatively, or additionally, data from sensor 289L resulting from tissue and/or fluid analysis using sensor 289L may be stored locally and transmitted later. For example, a signal including such analysis data may be transmitted after sensor 289L has been retracted back under cover 280. As yet another alternative, such a signal may be transmitted following surgery. In such implementations, the signals need not necessarily be transmitted wirelessly. In fact, some embodiments may be configured to store data locally, after which a data module, such as a memory stick, may be removed from the TD/TDM and uploaded to a separate computer for analysis.

The shaft of FIG. 2L further comprises antenna 218L. In the depicted embodiment, 218L represents an antenna configured to deliver a signal to a receiver unit. In some embodiments, antenna 218L may comprise any of the antennas described elsewhere herein including for example any of the antennas discussed in connection with antenna 218L. In embodiments in which antenna 218L comprises an RFID tag, the RFID tag may comprise an RFID transponder.

With reference again to FIG. 2b which is a perspective view of a break-away portion of the embodiment previously depicted in FIG. 2a. In the depicted embodiment, tip 201 may be made of materials that are both electrically non-conductive and of low thermal conductivity such as porcelain, epoxies, ceramics, glass-ceramics, plastics, or varieties of polytetrafluoroethylene. Alternatively, the tip may be made from metals or electroconductive materials that are completely or partially insulated. Note the relative protrusions and relative recessions are not completely visible from this viewing angle. In some embodiments, the relative recessions of the tip is the electrically conductive tissue lysing element 205 (usually hidden from view at most angles) which may have any geometric shape including a thin cylindrical wire; the electrically conductive lysing element can be in the shape of a plate or plane or wire and made of any metal or alloy that does not melt under operating conditions or give off toxic residua. Optimal materials may include but are not limited to steel, nickel, alloys, palladium, gold, tungsten, silver, copper, and platinum. Metals may become oxidized thus impeding electrical flow and function. In alternative embodiments the geometry of the tip area may comprise protrusions that are not oriented along the axis of the shaft (as seen from a top view); some of these alternative embodiments for tip area geometries are depicted in FIG. 5a, b, c, d. Some embodiments may be configured to be modular and/or comprise disposable tips such that a surgeon can place an appropriate tip for a particular surgery on the shaft. Alternatively or additionally one or more of the tips may be disposable such that a surgeon may dispose of the tip after performing surgery and install a new tip for subsequent surgeries or a continuation of the current surgery with a new tip.

An energy window 207 may be present on the upper side of the device. It is contemplated that in alternative embodiments, energy window 207 may be omitted. It should be noted that the term "energy window" is intended to encompass what is referred to as a planar-tissue-altering-window/zone in U.S. Pat. No. 7,494,488 and, as described later, need not be electrosurgically energized in all embodiments. In some embodiments, the "energy window" may comprise a variety of other energy emitting devices, including radiofrequency, intense pulsed light, LASER, thermal, microwave and ultrasonic. It should also be understood that the term "energy window" does not necessarily imply that energy is delivered uniformly throughout the region comprising the energy window. Instead, some energy window implementations may comprise a series of termini or other regions within which energy is delivered with interspersed regions within which no energy, or less energy, is delivered. This configuration may be useful for some implementations to allow for alteration of certain tissue areas with interspersed areas within which tissue is not altered, or at least is less altered. This may have some advantages for certain applications due to the way in which such tissue heals. A second energy window may also be included in some embodiments, and may comprise an ultrasound emitter or another variety of energy emitting device.

Electro-cutting energy may arrive in conduits 211 and/or 212.

In an embodiment, the tip may measure about 1 cm in width and about 1-2 mm in thickness. Sizes of about one-fifth to about five times these dimensions may also have possible uses. In some veterinary embodiments, tip sizes of about one-tenth to 20 times the aforementioned dimensions may also have possible uses. In some embodiments, the tip can be a separate piece that is secured to shaft by a variety of methods such as a snap mechanism, mating grooves, plastic sonic welding, etc. Alternatively, in some other embodiments, the tip can be integral or a continuation of shaft made of similar metal or materials. In some embodiments, the tip may also be constructed of materials that are both electrically non-conductive and of low thermal conductivity; such materials might comprise, for example, porcelain, ceramics, glass-ceramics, plastics, varieties of polytetrafluoroethylene, carbon, graphite, and graphite-fiberglass composites.

In some embodiments, the tip may be constructed of a support matrix of an insulating material (e.g., ceramic or glass material such as alumina, zirconia). Lysing segment energy conduit 211 connects to electrically conductive elements to bring RF electrosurgical energy from an electrosurgical generator down the shaft 202 to electrically conductive lysing elements 205 mounted in the recessions in between the protrusions 204. In some embodiments, the protrusions may comprise bulbous protrusions. The tip shown in this embodiment has four relative protrusions and three relative recessions and provides for a monopolar tip conductive element. All of the axes of the relative protrusions of the tip depicted in this embodiment extend at least substantially parallel to the axis of the shaft of the TD (as viewed from Top). In embodiments of tips of such axial placement of protrusions and or relative recessions, surgeons may use methods of defining and or dissecting a target area by entering through an incision and then moving the TD tip in a primarily axial direction forward and backward and reorienting the TD after the backstroke in a spokewheel pattern the TD to access tissues adjacent to earlier strokes. In some embodiments some of the protrusions and lysing segments may be oriented in a non-axial direction.

In the depicted embodiment, the tip 201 may alternatively be made partially or completely of concentrically laminated or annealed-in wafer layers of materials that may include plastics, silicon, glass, glass/ceramics, cermets or ceramics. Lysing elements 205 may also be made partially or completely of a cermet material. Alternatively, in a further embodiment the tip may be constructed of insulation covered metals or electroconductive materials. In some embodiments, the shaft may be flat, rectangular or geometric in cross-section or substantially flattened. In some embodiments, smoothing of the edges of the shaft may reduce friction on the skin surrounding the entrance wound. In some further embodiments, the shaft may be made of metal or plastic or other material with a completely occupied or hollow interior that can contain insulated wires, electrical conductors, fluid/gas pumping or suctioning conduits, fiberoptics, or insulation.

In some embodiments the shaft may have a length of about 10-20 cm. In some embodiments the handle may have a length of about 8-18 cm.

In some embodiments, shaft plastics, such as polytetrafluoroethylene may act as insulation about wire or electrically conductive elements. In some embodiments, the shaft may alternatively be made partially or completely of concentrically laminated or annealed-in wafer layers of materials that may include plastics, silicon, glass, glass/ceramics, ceramics carbon, graphite, graphite-fiberglass composites. The energy window 207 may only be substantially planar, or may take on other cross-sectional shapes that may correspond with a portion of the shape of the shaft, such as arced, stair-step, or other geometric shapes/curvatures. In the embodiments depicted in FIGS. 2a & 2b, energy window 207 is adjacent to protrusions 204, however other embodiments are contemplated in which an energy window may be positioned elsewhere on the shaft 202 or tip 201 of the wand, and still be considered adjacent to protrusions 204. However, if an energy window was placed on handle 203, such an energy window would not be considered adjacent to the protrusions 204.

Conduits may also contain electrical control wires to aid in device operation. Partially hidden from direct view in FIGS. 2a & 2b, and located in the grooves defined by protrusions 204 are electrically conductive tissue lysing elements 205, which, when powered by an electrosurgical generator, effects lysing of tissue planes on forward motion of the device. The lysing segments may be located at the termini of conductive elements. In some embodiments, one or more sensors such as for example sensors 210 and 214 may be positioned on the device. The sensors 210 and 214 may comprise any of the sensors described in the specification herein. Other embodiments may comprise one or more sensors on any other suitable location on the TD, including but not limited to on the protrusions or otherwise on the tip, and on the shaft. Sensors that may be useful include thermal sensors, photoelectric or photo optic sensors, cameras, etc. In some embodiments, one or more sensors may be used to monitor the local post passage electrical impedance or thermal conditions that may exist near the distal tip of the shaft or on the tip. Some embodiments may also comprise one or more sensors incorporating MEMS (Micro Electro-Mechanical Systems) technology, such as MEMS gyroscopes, accelerometers, and the like. Such sensors may be positioned at any number of locations on the TD, including within the handle in some embodiments. In some embodiments, sensor 214 may comprise fiberoptic elements. In an embodiment, the sensor can be configured to sense a temperature of tissue adjacent to the apparatus. The temperature sensor may alternatively be configured or sense a temperature of one or more fluids adjacent to the apparatus such as for example tissue fluids and/or fluids introduced by the surgeon.

Temperature and impedance values may be tracked on a display screen or directly linked to a microprocessor capable of signaling control electronics to alter the energy delivered to the tip when preset values are approached or exceeded. Typical instrumentation paths are widely known, such as thermal sensing thermistors, and may feed to analog amplifiers which, in turn, feed analog digital converters leading to a microprocessor. In some embodiments, internal or external ultrasound measurements may also provide information which may be incorporated into a feedback circuit. In an embodiment, an optional mid and low frequency ultrasound transducer may also be activated to transmit energy to the tip and provide additional heating and may additionally improve lysing. In some embodiments, a flashing visible light source, for example, an LED, can be mounted on the tip may show through the tissues and/or organs to identify the location of the device.

In some embodiments, one or more electromagnetic delivery elements 215 may be positioned on tip or shaft. Other embodiments may comprise one or more electromagnetic delivery elements on any other suitable location on the TD, including but not limited to on the protrusions or otherwise on the tip, and on the shaft. Electromagnetic delivery elements that may be useful include: LEDs, LASERs, fiberoptics, filaments, photoelectric materials, infrared emitters, etc.

A second energy window 208 may also be included in some embodiments, and may comprise yet another ultrasonic energy emitter or another variety of energy emitting device. An ultrasonically energized energy window 208 may be present on the upper side of the device. It is contemplated that in alternative embodiments, energy window 208 may be omitted. It should be noted that the term "energy window" is intended to encompass what is referred to as a planar-tissue-altering-window/zone in U.S. Pat. No. 7,494,488 and, as described later, need not be ultrasonically energized in all embodiments. In some embodiments, the "energy window" may comprise a variety of other energy emitting devices, including ultrasonic, intense pulsed light, LASER, thermal, microwave and electrical. It should also be understood that the term "energy window" does not necessarily imply that energy is delivered uniformly throughout the region comprising the energy window. Instead, some energy window implementations may comprise a series of energy delivering elements or other regions within which energy is delivered with interspersed regions within which no energy, or less energy, is delivered. An ultrasonic energy window configuration may be useful for some implementations, depending upon piezoelectric component and/or energy applied to less aggressively disrupt tissues (in order to possibly increase the concentration of target chemicals and/or biological compounds) at the cellular level to increase the availability of biological and/or chemical components to be sensed/analyzed and/or (may be at higher energy levels) to allow for alteration and/or damage to targeted tissues and/or heating for treatment. Energy window 208 may only be at least substantially planar, or may take on other cross-sectional shapes that may correspond with a portion of the shape of the shaft, such as arced, stair-step, or other geometric shapes/curvatures.

Some embodiments may comprise a low cost, disposable, and one-time-use device. However, in some embodiments intended for multiple uses, the tip's electrically conductive tissue lysing elements be protected or coated with materials that include, but are not limited to, Silverglide™ non-stick surgical coating, platinum, palladium, gold and rhodium. Varying the amount of protective coating allows for embodiments of varying potential for obsolescence capable of either prolonging or shortening instrument life.

In some embodiments, the electrically conductive lysing element portion of the tip may arise from a plane or plate of varying shapes derived from the aforementioned materials by methods known in the manufacturing art, including but not limited to additive manufacturing, cutting, stamping, pouring, molding, filing and sanding. In some embodiments, the electrically conductive lysing element 205 may comprise an insert attached to a conductive element in the shaft or continuous with a formed conductive element coursing all or part of the shaft. In some embodiments, a lysing segment energy conduit 211 brings RF electrosurgical energy down the shaft to electrically conductive lysing elements 205 associated in part with the recessions. In an embodiment, the electrosurgical energy via conduit 211 is predominately electro-cutting.

In some embodiments, the electrically conductive element or wiring may be bifurcated to employ hand switching if an optional finger switch is located on handle. The electrically conductive element or wiring leading from the shaft into the handle may be bundled with other leads or energy delivering cables, wiring and the like and may exit the proximal handle as insulated general wiring to various generators (including electrosurgical), central processing units, lasers and other sources as have been described herein. In some embodiments, the plate making up lysing segments 205 may be sharpened or scalloped or made to slightly extend outwardly from the tip recessions into which the plate will fit.

Alternatively, in some embodiments, since cutting or electrical current may cause an effect at a distance without direct contact, the lysing element may be recessed into the relative recessions or grooves defined by the protrusions 204 or, alternatively, may be flush with protrusions 204. In some further adjustable embodiments, locations of the electrically conductive lysing elements with respect to the protrusions may be adjusted by diminutive screws or ratchets. In some further adjustable embodiments, locations of the electrically conductive lysing elements with respect to the protrusions may be adjusted by MEMS or microelectronics. The plate, which in some embodiments is between 0.01 mm and 1 mm thick, can be sharpened to varying degrees on its forward facing surface. It is possible that plate sharpness may increase the efficiency with which electricity will pass from the edge cutting the target tissue. Sometimes, however, proper function even when variably dull or unsharpened may be unhampered since electrosurgical cutting current may cut beyond the electroconductive edge by a distance of over 1 mm. In some embodiments, the plate thickness may vary from 0.001 mm to 3 mm thick.

In some embodiments, the electrically conductive lysing element may also exist in the shape of a simple wire of 0.1 mm and 1 mm 0.01 mm to 3 mm. In some embodiments, the wire may measure between 0.01 mm to 3 mm. Such a wire may be singly or doubly insulated as was described for the plate and may have the same electrical continuities as was discussed for the planar (plate) version. In some embodiments, an electrosurgical current for the electrically conductive lysing element is of the monopolar "cutting" variety and setting and may be delivered to the tip lysing conductor in a continuous fashion or, alternatively, a pulsed fashion. The surgeon can control the presence of current by a foot pedal control of the electrosurgical generator or by button control on the shaft (forward facing button). The amount of cutting current may be modified by standard interfaces or dials on the electrosurgical generator. For some embodiments, the electrically conductive lysing element is a monopolar tip in contact with conductive elements in the shaft leading to external surgical cable leading to an electrosurgical generator from which emanates a grounding or dispersive plate which may be placed elsewhere in contact with the patient's body, such as the thigh. Such circuitry may be controlled and gated/wired from the cutting current delivery system of the electro surgical generator. In an embodiment, the tip may also be manufactured from multilayer wafer substrates comprised of bonded conductive strips and ceramics. Suitable conductive materials include but are not limited to those already described for tip manufacture.

In alternative embodiments, the electrically conductive lysing elements may be bifurcated or divided into even numbers at the relative recessions, insulated and energized by wiring to an even number of leads in a bipolar fashion and connected to the bipolar outlets of the aforementioned electrosurgical generators. Rings partly or completely encircling the shaft of the hand unit can be linked to a partner bipolar electrode at the tip or on the energy window. Such bipolar versions may decrease the available power necessary to electrically modify certain tissues, especially thicker tissues. In alternative embodiments, the lysing elements may be divided into odd numbers yet still allow for bipolar flow between two or more elements as those of ordinary skill in the art would appreciate.

FIGS. 3a-j depict various views of a particular embodiment of a tissue dissector (TD) with a sensor dock on the upper side of the device with a movable cover.

FIG. 3a is a perspective view of an embodiment of a TD comprising a tip 301 lacking protrusion and lysing segments, a shaft 302, a handle 303. In the depicted embodiment, tip 301 is radiused and blunt. The depicted embodiment also lacks cutting current availability on the tip. An ultrasonically energized energy window 307 may be present on the upper side of the device. It is contemplated that in alternative embodiments, energy window 307 may be omitted. It should be noted that the term "energy window" is intended to encompass what is referred to as a planar-tissue-altering-window/zone in U.S. Pat. No. 7,494,488 and, as described later, need not be ultrasonically energized in all embodiments. In some embodiments, the "energy window" may comprise a variety of other energy emitting devices, including radiofrequency, intense pulsed light, LASER, thermal, microwave and electrical. It should also be understood that the term "energy window" does not necessarily imply that energy is delivered uniformly throughout the region comprising the energy window. Instead, some energy window implementations may comprise a series of energy delivering elements or other regions within which energy is delivered with interspersed regions within which no energy, or less energy, is delivered. An ultrasonic energy window configuration may be useful for some implementations, depending upon piezoelectric component and/or energy applied to less aggressively disrupt tissues (in order to possibly increase the concentration of target chemicals and/or biological compounds) at the cellular level to increase the availability of biological and/or chemical components to be sensed/analyzed and/or (may be at higher energy levels) to allow for alteration and/or damage to targeted tissues and/or heating for treatment. A second energy window may also be included in some embodiments, and may comprise a microwave emission device or another variety of energy emitting device. In some contemplated embodiments, one or more energy windows may be present on the tip and/or shaft as discussed elsewhere in this disclosure. Energy window 307 may only be at least substantially planar, or may take on other cross-sectional shapes that may correspond with a portion of the shape of the shaft, such as arced, stair-step, or other geometric shapes/curvatures.

Ultrasonic Energy Window 307 may be configured to for example, disrupt cells to release chemicals and/or biomarkers and/or heat target tissues and/or fluids. In the depicted embodiment, Ultrasonic Energy Window 307 comprises a piezoelectric ceramic. In an embodiment the piezoelectric ceramic may measure about 20 mm×8 mm×3 mm. In some embodiments, the piezoelectric ceramic may measure up to about 50 mm in diameter. It is contemplated that in alternative embodiments, Ultrasonic Energy Window 307 may be omitted. In some embodiments the piezoelectric ceramic is made from lead zirconate titanate piezoelectric ceramic (which may be sold as PZT8 or PZT4 by Micromechatronics, State College, Pa.). In some embodiments the piezoelectric may comprise quartz and/or barium titanate and/or film polymer polyvinylidene fluoride. In some embodiments the ultrasonic energy window measures between 1 mm and 50 mm in any dimension. Some embodiments may comprise a plurality of ultrasonic energy windows. Depending upon the composition of a piezoelectric and/or the surrounding environment and/or the structure(s) in which the piezo is mounted, a given mounted piezoelectric ceramic may have one or more harmonic frequencies. It may be beneficial once a surgeon has reached a target site to restrict the gross movement of the TD around from the target site, yet still have the surgeon be able to agitate target tissues and/or cells for analysis. However, such ultrasonic disruption of cells and/or tissues without causing significant damage to surrounding and/or deeper tissues may be dependent upon the dampening effects of fluids in the target areas as well as the water composition of the targeted tissues and/or other characteristics of the tissues. In some embodiments, frequency ranges and energy ranges that may be beneficial in disrupting target cells to a limited degree may be within a frequency range of about 25 to 40 kiloHertz with energy level ranges of about 3-10 Watts and/or 10-30 Volts. In some embodiments, depending upon the tissues and/or environment, application time ranges of about 5-60 seconds may be possible to lyse some target cells. Increasing the contact of the Ultrasonic Energy Window 307 to the tissues, possibly by pressing on the TD, may reduce intervening tissue fluids and/or water between the Ultrasonic Energy Window and the target tissues and thus increase coupling between the energy window and the target tissue which may increase the efficiency of ultrasonic energy delivery. In some implementations, after or instead of agitating tissue using ultrasonic energy window at relatively low energy as discussed above Ultrasonic Energy, window 307 may be used to heat and/or treat and/or damage target tissues by applying a higher frequency range such as a frequency range in excess of 40 kiloHertz. In some implementations, window 307 may be used to heat and/or treat and/or damage target tissues by applying a higher energy level with energy parameters that may range to about 10-20 Watts and/or 30-50 Volts. Examples of ultrasound technology that may be useful for some of the embodiments disclosed herein such as for ultrasonic energy windows 307 and/or 308 may be found in Miniaturized Ultrasound Arrays for Interstitial Ablation and Imaging (Makin, Mast, Faidi, et al.; Ultrasound Med Biol 2005; 31(11):1539-50.) and/or Design and Preliminary Results of an Ultrasound Applicator for Interstitial Thermal Coagulation (Lafon, Chapelon, Prat, et al.; Ultrasound Med Biol 1998; 24(1):113-22.) and/or Optimizing the Shape of Ultrasound Transducers for Interstitial Thermal Ablation (Lafon, Theillere, et al.; Med Phys 2002; 29(3):290-7.) and/or Rapid Skin Permeablization by the Simultaneous Application of Dual Frequency, High-Intensity Ultrasound (Schoelhammer, Polat, Mendenhall, Langer, et al; Journal of Controlled Release, 2012, 163(2)154-160.) and/or Interstitial Devices for Minimally Invasive Thermal Ablation by High Intensity Ultrasound (Lafon, Melodelima, Salomir, Chaelon; Int J. Hyperther 2007; 23(2):153-63.) and/or Theoretical Comparison of Two Interstitial Ultrasound Applicators Designed to Induce Cylindrical Zones of Tissue Ablation (Lafon, Chavrier, Prat, et al.; Med Biol Eng Comput 1999; 37(3):298-303.) and/or Feasibility of Linear Arrays for Interstitial Ultrasound Thermal Therapy (Chopra, Bronskill, Foster; Med Phys 2000; 27(6):1281-6.) and/or Development of an Interstitial Ultrasound Applicator for Endoscopic Procedures: Animal Experimentation (Lafon, Theillere, Prat, et al.; Ultrasound Med Biol 2000; 26(4):669-75.) and/or Multisectored Interstitial Ultrasound Applicators for Dynamic Angular Control of Thermal Therapy (Kinsey, Diederich, Tyreus, et al.; Med Phys 2006; 33(5):1352-63.) and/or Evaluation of Multielement catheter-cooled interstitial ultrasound applicators for high-temperature thermal therapy (Nau, Diederich, Burdette; Med Phys 2001; 28(7): 1525-34.) and/or Feasibility of Ultrasound Hyperthermia with Waveguide Interstitial Applicator (Jarosz; IEEE Trans Biomed Eng 1996; 43(11):1106-15.) and/or Transurethral Ultrasound Array for Prostate Thermal Therapy: Initial Studies (Diederich, Burdette; IEEE Trans Ultrason Ferroelectr Freq Control 1996; 43(6):1011-22.) which are hereby incorporated by reference in its entirety.

In some embodiments, an ultrasonic energy window may be provided that is configured to allow for selective adjustment of one or more such parameters, including power, voltage, and/or frequency, as described above. This may be useful to, for example, allow a surgeon to use higher energy/power to access a desired tissue/organ, such as to get through investing fibrous tissues adjacent an organ by rubbing the surface of the TDM containing the ultrasonic energy window tangentially with a surface of the organ and/or its surrounding fibrous tissue. A surgeon may then turn down the power/energy in order to disrupt cells within the organ to a more limited degree in order to facilitate sampling/analysis of tissues and/or fluids within the organ. Alternatively, some embodiments may be configured with two separate ultrasonic energy windows. One such window may be configured to deliver relatively high power/energy, as described above, and the other such window may be configured to deliver relatively low power/energy.

In some embodiments, an ultrasonic energy window may be used in a procedure to agitate and/or disrupt a biofilm. Since microorganisms making up a biofilm typically have significantly different properties from free-floating bacteria or other microorganisms, such disruption may be useful to allow for sampling and/or analysis of microorganisms making up the biofilm that may have been difficult or impossible without such agitation/disruption.

Examples of ultrasound technology that may be useful for some of the embodiments disclosed herein such as for ultrasonic energy windows 307 and 308 may be found in Rapid Skin Permeablization by the Simultaneous Application of Dual Frequency, High-Intensity Ultrasound (Schoelhammer, Polat, Mendenhall, Langer, et al; Journal of Controlled Release, 2012, 163(2)154-160.) and Ultrasonic Mediated Glucose Measurements In Vivo Using the Cymbal Array (Lee, Nayak, Dodds et al; Ultrasound Med Biol. 2005. 31: 971-977) and Effects of Low-Frequency Ultrasound on the Transdermal Permeation of Mannitol: Comparative Studies with in Vivo and in Vitro Skin. (Tang, Bankschtein, Langer: J Pharm Sci. 2002. 91:1776-1794) and Transdermal Delivery System of Tiamcinolone Acetonide From Gel Using Phonophoresis (Yang, Kim, Yun; Arch Pharm Res. 2006. 29:412-417) which are hereby incorporated by reference in its entirety.

Returning to FIG. 3a (a perspective view of an embodiment of a TD comprising a tip 301, a shaft 302 and a handle 303); located on the shaft 302 is dock 384 that may accommodate seat 388 which may releasably hold sensor 389. In some embodiments sensor 389 may comprise a nanosensor. In some embodiments, dock 384 may be recessed into shaft 302 and/or tip 301. In some embodiments dock 384 may protrude from shaft 302 and/or tip 301. In some embodiments dock 384 may be flush with shaft 302 and/or tip 301. In some embodiments, sensor 389 may comprise a silicon nanowire sensor. In some embodiments the sensor 389 may comprise a biological nanosensor. In some embodiments, nanosensor 189 may comprise a conducting polymer and/or glass and/or polymer and/or plastic and/or graphene and/or carbon, etc. In some embodiments, seat 388 may be fixed in position. In some embodiments, seat 388 may be moveable. In some embodiments sensor 384 may be fixed in seat 188. In some embodiments, the sensor 389 may be detachable seat 388. It is contemplated that in alternative embodiments, seat 388 may be omitted. In some embodiments the dock may comprise cover moving means and/or a cover tip. Cover tip 381 and means for selectively moving a cover 383 may be positioned adjacent dock 184. Examples of such cover moving means may include rails, grooves, tracks, ratchets, cables, arms, lines, etc. In the depicted embodiment the cover moving means comprises a rail. In some embodiments a portion of the shaft may comprise cover moving means 383. It is contemplated that in alternative embodiments, cover moving means 383 may be omitted. Dock 384 may comprise one or more dock wall(s) 385. Dock wall 385 may comprise fluid delivery port 386 for fluid delivery conduit. Dock wall 385 may comprise fluid extraction port 387 for fluid extraction conduit. In some embodiments, dock wall 385 may comprise one or more ports 386 and/or 387. In FIG. 3c, cover 380 is moveable along cover moving means 383 and may be opened or closed via internal control wires. In some embodiments the cover may be moved by motors. Rear end of cover 382 may be fixed to cover 380. In some embodiments, rear end of cover 382 is not fixed to cover and is itself attached to another portion of the TD. In some embodiments, dock 384 and/or dock wall 385 may accommodate a temperature modification means 395 for modifying a temperature within the dock 384 and cover 380. Temperature modification means 395 may comprise, for example a heater, a Peltier cooler, a heat pump, etc. Temperature modification means 395 may be used to heat fluids introduced by way of port 386. Temperature modification means 395 may alternatively be used to heat tissues and/or other fluids such as body tissues and/or fluids captured during a procedure using the TD. In some embodiments temperature modification means 395 may facilitate and/or inhibit certain chemical reactions and/or bond alterations that may be needed in order to sense certain biomaterials using sensor 389. In some embodiments, dock 384 and/or dock wall 385 may accommodate mixing element 396. In some embodiments temperature modification means 395 may comprise an electrical resistance heater. In contemplated embodiments, heater 395 may comprise a thin film resistor and/or piezoelectric heating device and/or other device capable of heating fluids. In some embodiments, mixing element 396 may comprise a propeller driven by an electric motor. In some embodiments, mixing element 396 may comprise one or more flaps of relatively inert flexible polymeric plastic on a post spun by an electric motor. Examples of other materials for such a flap may include polymers, metals, ceramics, etc. In another embodiment, mixing element 396 may comprise an unattached stirring rod spun by oscillating magnet. In a contemplated embodiment, a separate set of ports may originate and terminate in dock 384, and may be connected by conduit which is fluidly coupled with a piezoelectric pump and/or another fluidic motor and/or another fluidic driving device. In embodiments including one or more such additional ports, such port(s) may be positioned at an opposite end of dock 384 such that delivery of fluid(s) and/or application of a vacuum may be applied more evenly throughout dock 384. It is contemplated that in alternative embodiments, temperature modification means 395 and/or mixing element 396 may be omitted. One or more sensors 378 and/or 379 may be located on dock 384. In some embodiments, one or more sensors 378 and/or 379 may be located on dock wall 385 and/or cover 380. Sensors 378 and/or 379 may comprise any of the specific examples of sensors discussed in connection with sensors 310 and/or 314. Sensor(s) 378 and/or 379 may report conditions and/or changing conditions in dock area 384 in and/or around nanosensor 389.

Nanosensors may be obtained/manufactured by methods available to those of ordinary skill in the art, including but not limited to: U.S. Pat. No. 8,022,444 B2 titled "Biosensor and Method of Manufacturing the Same," and/or U.S. Pat. No. 8,314,357 B2 titled "Joule Heated Nanowire Biosensors," and/or U.S. Pat. No. 8,236,595 B2 titled "Nanowire Sensor, Nanowire Sensor Array and Method of Fabricating the Same," and/or Label Free DNA Sensor Using a Silicon Nanowire Array (Kulkarni, Xu, Ahn, Amin, et. al.; J Biotechnol, 2012, Aug. 31; 160(3-4):91-6.) and/or Conducting Polymers: An Emerging Field of Biosensors (Borole, D D et al.; Des Monomers Polymers, 2006 9(1): p. 1-11.) and/or Conducting Polymers for DNA Sensors and DNA Chips: from Fabrication to Molecular Detection (Mailley, Livache; Electrochemistry of Nucleic Acids and Proteins—Towards Electrochemical Sensors for Genomics and Proteomics, 2005: p. 297-330.) and/or Conducting Polymers for Electrochemical DNA Sensing (Peng, H., et al., Biomaterials, 2009, 30(11): p. 2132-2148.) and/or Conductive Electroactive Polymers: Intelligent Materials Systems (Wallace, Spinks, Teasdale. Vol. 317. 1998.287-290.) Conducting Polymer Nanowire-based Biosensors (Wanekaya, et al.; Handbook of Biosensors and Biochips, 2007 (2) p. 831-842.) and/or Conductive Electroactive Polymers: Intelligent Materials Systems, Second Edition, 2002 (Wallace, Spinks, Kane-Maguire p224.) and/or Novel Conducting Polymers for DNA Sensing (Peng et al.; Macromolecules, 2007, 40(4): p. 909-914.) and/or Direct Ultrasensitive Electrical Detection of DNA and DNA Sequence Variations Using Nanowire Nanosensors (Nano Letters, 2003. 4(1): p. 51-54.) and/or Sequence-Specific Label-Free DNA Sensors Based on Silicon Nanowires (Li, et al; Nano Letters, 2004. 4(2): P. 245-247.) and/or Sensing by Silicon Nanowire: Charge Layer Distance Dependence (Zhang, et al.; Nano Letters, 2008. 8(4): p. 1066-1070.) and/or Nanowire Nanosensors for Highly Sensitive and Selective Detection of Biological and Chemical Species (Yi Cui, et al.; Science vol 293 (2001) p. 1289.) and/or U.S. Pat. No. 17,993,538 B2, titled "Patterning by Energetically-Stimulated Local Removal of Solid-Condensed-Gas Layers and Solid State Chemical Reactions Produced with Such Layers" and/or U.S. Pat. No. 7,674,389 B2 titled "Precision Shape Modification of Nanodevices with a Low-Energy Electron Beam," and/or U.S. Pat. No. 5,645,740 titled "System and Assemblage for Producing Microtexturized Substrates and Implants," and/or U.S. Pat. No. 5,607,607 titled "System and Assemblage for Producing Microtexturized Substrates and Implants," and/or U.S. Pat. No. 7,416,911 B2 titled "Electrochemical Method for Attaching Molecular and Biomolecular Structures to Semiconductor Microstructures and Nanostructures," and/or U.S. Pat. No. 7,294,526 B2 titled "Nano Optical Sensors via Molecular Self-Assembly," and/or U.S. Pat. No. 6,870,235 B2 titled "Silicon-on-Insulator Biosensor Device," and/or U.S. patent application Ser. No. 12/065,857, Publication No: US2009/0140167 A1, titled "Nanotube Fabric-Based Sensor Systems and Methods of Making Same," and/or U.S. Pat. No. 6,716,620, filed Mar. 26, 2001, titled "Biosensor and Related Method," and/or U.S. Pat. No. 7,129,554 B2, titled "Nanosensors," and/or U.S. patent application Ser. No. 13/209,442, publication number US2012/0304776 A1, titled "Chemical and Biomedical Nanosensors" which are hereby incorporated by reference in its entirety.

For example, some of the reagents and/or chemicals and/or biochemicals that may be present in and/or delivered to and/or removed from the dock area to facilitate sensor use and/or cleaning, etc., may include but not be limited to ethanolic solutions, thiols, SDS (sodium dodecyl sulfate), water, argon gas, sodium chloride, sodium bicarbonate buffer, EGTA (ethylene glycol tetraacetic acid), EDTA (ethylenediaminetetraacetic acid), sulfo-NHS diazirine (sulfo-SDA), PBS (phosphate buffered saline), and/or Tween®-20 (PBST), etc. Such reagents and/or chemicals and/or biochemical and their acquisition and use are available to those of ordinary skill in the art, including but not limited to: U.S. Pat. No. 6,593,093 B1 titled "Detection of Group A Streptococcus"; U.S. Patent Application Publication No. 2012/0228155A1 titled "Electromagnetic Detection of Analytes"; U.S. Patent Application Publication No. 2009/0186774 A1 titled "Sepsis Detection Microarray"; European Patent 2526427 A2, titled Rapid Pathogen Diagnostic Device and Method"; U.S. Patent Application Publication No. 2006/0223080 A1, titled "Compositions and Methods for Detecting Group A Streptococci"; Scanometric DNA Array Detection with Nanoparticle Probes (TATON, MIRKIN, LESTINGER; Science, 8 Sep. 2000, vol. 289, no 5485, pp 1757-1760.); Detection of Methicillin-Resistant Staphylococcus aureus (MRSA) using the NanoLantern Biosensor (STROHSAHL, MILLER, KRAUSS; Proc. of SPIE, Vol 7167OS pp. 1-12.); Ultrasensitive and Selective Multiplexing Detection of Cancer Markers Using Nanowire Nanosensors (CIU, WANG, HUYNH, LIEBER; Harvard University, pp 1-21.); Field Effect Transistor Nanosensor for Breast Cancer Diagnostics (MOHANTY, CHEN, WANG, HONG, ROSENBERG, WEAVER, ERRAMILLI; Boston University, pp. 1-25.); all of which are hereby incorporated herein by reference in their entirety.

In some embodiments, sensor 378 and or sensor 379 may comprise a camera. In some embodiments, sensor 378 and or sensor 379 may comprise a fiberoptic and/or fiberoptic camera and/or CCD camera and/or other camera.

In some embodiments, one or more electromagnetic delivery elements 377 may be positioned on dock 384 tip and/or cover 380 and/or tip of cover 381. Other embodiments may comprise one or more electromagnetic delivery elements on any other suitable location on the TD, including but not limited to on the sensor 389 or otherwise on seat 388. Electromagnetic delivery elements that may be useful include but are not limited to: LEDs, LASERs, fiberoptics, filaments, photoelectric materials, infrared emitters, etc. In some implementations, emission of such electromagnetic energy may be absorbed by a chemical and/or biomolecule on the sensor and/or dock area and/or reflectance and/or emission spectra of the chemical and/or biomolecule and/or a further product may be detected via sensors 378 and/or 379. In an embodiment, cover 380 and/or dock 384 may be configured to reflect electromagnetic radiation. Reflecting electromagnetic radiation and/or having mirror-like properties may allow for detection of electromagnetic radiation by sensors 378 and/or 379. In some embodiments, cover 380 and/or dock 384 comprise a thin film coating over a substrate. In some embodiments, the substrate may be plastics and/or molded polymer and/or crystal and/or glass and/or metal, etc In some embodiments, cover 380 and/or dock 384 comprise a coating of aluminum. In some embodiments the aluminum coating comprises a protected aluminum and/or enhanced aluminum and/or UV-enhanced aluminum (a maker may be Edmund Optics, Barrington, N.J., USA).

In the depicted embodiment cover 380 may comprise plastic. In other embodiments cover 380 may comprise materials including but not limited to: polymers, quartz, glass, carbon based materials, silicates and/or metals.

In some embodiments, one or more sensors such as for example sensors 310 and 314 may be positioned on the device. The sensors 310 and 314 may comprise any of the sensors described in the specification herein. In some embodiments, sensor 310 and or sensor 314 may comprise a camera. In some embodiments, sensor 310 and or sensor 314 may comprise a fiberoptic and/or fiberoptic camera and/or CCD camera and/or other camera. Other embodiments may comprise one or more sensors on any other suitable location on the TD, including but not limited to on the protrusions or otherwise on the tip, and on the shaft. Sensors that may be useful include thermal sensors, photoelectric or photo optic sensors, cameras, etc. In some embodiments, one or more sensors may be used to monitor the local post passage electrical impedance or thermal conditions that may exist near the distal tip of the shaft or on the tip. Some embodiments may also comprise one or more sensors incorporating MEMS (Micro Electro-Mechanical Systems) technology, such as MEMS gyroscopes, accelerometers, and the like. Such sensors may be positioned at any number of locations on the TD, including within the handle in some embodiments. In some embodiments, sensor 314 may comprise fiberoptic elements. In an embodiment, the sensor can be configured to sense a temperature of tissue adjacent to the apparatus. The temperature sensor may alternatively be configured or sense a temperature of one or more fluids adjacent to the apparatus such as for example tissue fluids and/or fluids introduced by the surgeon.

Temperature and impedance values may be tracked on a display screen or directly linked to a microprocessor capable of signaling control electronics to alter the energy delivered to the tip when preset values are approached or exceeded. Typical instrumentation paths are widely known, such as thermal sensing thermistors, and may feed to analog amplifiers which, in turn, feed analog digital converters leading to a microprocessor. In some embodiments, internal or external ultrasound measurements may also provide information which may be incorporated into a feedback circuit. In an embodiment, an optional mid and low frequency ultrasound transducer may also be activated to transmit energy to the tip and provide additional heating and may additionally improve lysing. In some embodiments, a flashing visible light source, for example, an LED, can be mounted on the tip may show through the tissues and/or organs to identify the location of the device.

In some embodiments, one or more electromagnetic delivery elements 315 may be positioned on tip or shaft. Other embodiments may comprise one or more electromagnetic delivery elements on any other suitable location on the TD, including but not limited to on the protrusions or otherwise on the tip, and on the shaft. Electromagnetic delivery elements that may be useful include: LEDs, LASERs, fiberoptics, filaments, photoelectric materials, infrared emitters, etc.

As shown in FIG. 3a, handle 303 may comprise one or more ports through which various conduits may be passed. In some such embodiments, a plurality of conduits may be bundled together for convenience if desired. In addition, a miscellaneous conduit bundle 399 may be provided. Miscellaneous conduit bundle 399 may comprise, for example, various other conduits, such as conduits for one or more sensors, such as sensors 310 and 314, one or more electromagnetic delivery elements 315, fluid delivery port(s) 316, and/or suction/vacuum ports 317. In addition, miscellaneous conduit bundle 399 may comprise one or more additional conduits, such as one or more additional fluid delivery conduits for delivering a fluid, such as a liquid or gas, to port 386 in dock 384 in the TD. Miscellaneous conduit bundle 399 may further comprise one or more fluid extraction conduits (from port 387 in dock 384) for extracting of fluid to direct the fluid (again, a liquid or gas) to a remote fluid/chemical sensor.

The fluid delivery conduit (leading to port 386) may be configured to deliver, for example, buffers, cleansers, quenching agents, reagents, biological compounds, inert compounds, gases. Fluids delivered (by way of a fluid delivery conduit leading to port 386) may be energized, such as heated, ultrasonically energized, may contain detergents, antibodies, drugs, etc.

Fluid extraction conduits (leading from port 387) may not only be used to withdraw fluids to be discarded from the body, but also may be used in a wash circuit to remove fluids introduced by way of fluid delivery conduit leading to port 386 that are used to, for example, wash and/or disinfect certain tissues and/or components of the TD. Fluid extraction conduit (leading from port 387) may also be used to extract fluids for external analysis. Some embodiments may be configured to provide a bubble between separate sets of fluids to allow a user to distinguish between various fluid streams delivered using fluid extraction conduit leading from port 387.

In some embodiments, a vibration means 370 may be positioned in the handle. Other embodiments may comprise one or more vibration means on any other suitable location on the TD, including but not limited to on the protrusions or otherwise on the tip, and on the shaft. Examples of suitable vibration means may include piezoelectric materials, ultrasonic motors with stators, piezoelectric actuators, vibration motor such as an off-center weight mounted on a gear, etc. Some vibration means may be configured to emit ultrasound in the 20-40 kHz range. Yet other vibration means may include electromagnet drivers with a frequency of operation in the range of 150-400 Hz. In some embodiments, one or more vibration means may be used to provide additional forces which may facilitate passage of the TD. In some embodiments use of a vibration means may, also or alternatively, be used to assist in migrating the TD through tissue during the procedure. In some such embodiments, it is thought that use of a vibration means having a lower frequency may be particularly useful for assisting in such migration. In addition, positioning the vibration means closer to a handle of the TD may facilitate such migration as well. FIG. 3 *d, c* depict the TD with cover 380 moved proximally to expose dock.

FIG. 3 *f, e* depict the TD with cover 380 moved distally to close over and/or seal dock.

FIG. 3*g* is cross sectional view of an embodiment of cover 380 comprising a groove 391 and projection 392 as described herein. Groove 392 may be used to direct fluids within cover 180 to facilitate mixing of fluids and/or directing fluids to locations in need of cleaning and/or directing fluids to sensor locations and/or bringing fluids of with a temperature range to locations within the dock or cover. Similarly as described herein, projection 392 may also be used to direct fluids to one or more desired locations and/or agitate fluids in a desired manner for a particular use.

FIG. 3*h* is cross sectional view of an embodiment of dock 384 comprising a groove 393 and a projection 394 as described herein. Groove 393 may be used to direct fluids within dock 384 to facilitate mixing of fluids and/or directing fluids to locations in need of cleaning and/or directing fluids to sensor locations and/or bringing fluids of with a temperature range to locations within the dock or cover. Similarly as described herein, projection 394 may also be used to direct fluids to one or more desired locations and/or agitate fluids in a desired manner for a particular use. In some embodiments, cover 380 and dock 384 may when cover 380 is in a closed position, define a common space. In some embodiments, cover grooves 391 may operate in conjunction with dock grooves 393 or dock protrusions 394 to impact fluid behavior in a desired manner.

In FIGS. 3*g* and/or 3*h*, one or more grooves 391 and 393 may be provided for example in dock 384 and/or in an interior surface of cover 380 in order to direct fluids delivered through port 386 are directed to desired to one or more desired locations. In some embodiments grooves may be configured to facilitate mixing of fluids and/or directing fluids to locations in need of cleaning and/or directing fluids to sensor locations. One or more projections 392 and 394 may be provided for example in dock 384 and/or in an interior surface of cover 380 in order to direct fluids delivered through port 386 are directed to desired to one or more desired locations. In some embodiments projections may be configured to facilitate mixing of fluids and/or directing fluids to locations in need of cleaning and/or directing fluids to sensor locations. In some embodiments multiple projections may define a groove, in other embodiments one or more grooves may be formed within a surface of a cover and/or dock.

With the cover 380 closed, as depicted in FIG. 1*e*, fluids may be circulated within the space enclosed by cover 380 which may facilitate cleaning. Closing cover 380 may also facilitate isolation of biological tissues and/or fluids. For example, closure of cover 380 may allow for analysis of tosses and/or fluids while preventing contamination by other such tissues and fluids after a sample has been taken. Cleaning may be further facilitated by positioning of the seat and/or sensors at an angle and/or various angles. The configuration depicted in FIG. 1*i* may be primarily for facilitating capture to tissue and/or fluids for analysis, however some embodiments may be configured to tilt seat 388 toward a rear portion of the TD such that it faces (tilts toward) fluid port 386 to facilitate cleaning of sensor 389.

Fluid delivery port 386 for fluid delivery and fluid extraction port 387 for fluid extraction may also serve to deliver and/or remove fluids, for example, including but not limited to reagents and/or analyte(s) and/or eluent(s) and/or eluate(s). In some embodiments, fluid delivery from fluid delivery port 386 and/or fluid extraction from fluid extraction port 387 may be linked in a circuit with a pump and/or additional conduit (that is coupled with one or both of the conduits coupled with fluid delivery port 386 and fluid extraction port 387) to recirculate and/or heat and/or incubate and/or mix and/or add reagents and/or remove reagents and/or other materials from the space within the cover 380 and/or dock 384. In some embodiments, a pump external to the TD, fluidly connected to the circuit between the conduits connecting ports 387 and 386, may be used to move fluids. The available space for fluids between the cover 380 and dock 384 (with space occupying elements) may be derived by measuring an amount of fluid entering and/or exiting from ports 386 and/or 387 via their conduits. Such measurements may be compared with CAD (Computer Aided Design) calculations of the space.

FIG. 3*i* is a side (break away) side view, of the embodiment previously depicted in FIG. 3*a* of a TD, illustrating an example of positioning and/or protruding a seat (containing a nanosensor) that may allow for some exposure to passing tissues or fluids. The TD may comprise an actuator 390. In some embodiments, actuator 390 may comprise a motor. In some embodiments actuator 390, may comprise one or more such motors such as a screw-drive motor, gear motor, hydraulic motors etc. In some embodiments actuator 390 may comprise worm gearheads, motor control circuits, monitors, remote control devices, etc. In some embodiments, actuator 390 may be controlled or moved by wire and/or spring. In some embodiments, actuator may be controlled or moved by wire using manual work. In some embodiments actuator 390 may be omitted. In some embodiments, seat 388 may be configured to be manually actuated or tilted. In some embodiments, seat 388 may be configured to be positioned in affixed number of angles relative to shaft 302 and/or dock. In other embodiments, seat 388 may be configured to be repositioned in an infinite number of angled positions relative to shaft 302 and/or dock.

Means for delivering ultrasonic energy 397 may be located in/on in/on dock wall 385 of dock 384. Ultrasonic means 397 may be configured to for example, heat fluids: aid in the cleaning of one or more portions of the TD including for example dock 384: aid in the mixing of reagents and/or organic chemicals and/or biomolecules; aid in the fixation of biomolecules and/or other substances to receptors and/or sensors; aid in the removal of biomolecules and/or other substances to receptors. In the depicted embodiment the ultrasonic means comprises a piezoelectric ceramic. In some embodiments the piezoelectric ceramic may measure about 2 mm×2 mm×4 mm. It is contemplated that in alternative embodiments, ultrasonic means 397 may be omitted. In some embodiments the piezoelectric ceramic is made from lead zirconate titanate piezoelectric ceramic (which may be sold as PZT8 or PZT4 by Micromechatronics, State College, Pa.) and may be driven by 2-5 Watts at 10-20 Volts and/or may be configured to vibrate at a frequency of 300-500 kiloHertz. In some embodiments the piezoelectric may comprise quartz and/or barium titanate and/or film polymer polyvinylidene fluoride. In some embodiments the ultrasonic means measures between 1 mm and 20 mm in any dimension. Some embodiments may comprise a plurality of ultrasonic means. In some embodiments, ultrasonic means may be configured to be positioned on two or more intersecting surfaces, for example in the embodiment depicted in FIG. 1b a portion of ultrasonic means 397 is positioned on an upper surface of shaft 302 and a second portion of ultrasonic means 397 is positioned along dock wall 385 which intersects the upper surface of shaft 302. in the depicted embodiment wall 385 intersects the top surface of shaft 1302 at a substantially perpendicular angle.

In the embodiment depicted in FIG. 3i, positioning the seat 388 and/or sensors 389 at one or more angles while the cover is in the open position may allow sensor(s) 389 to increase and/or alter contact and/or friction to facilitate a desired reaction between sensor 389 passing tissues and/or fluids.

In the embodiment depicted in FIG. 3j, positioning the seat 388 and/or sensors 389 at least at a substantially parallel angle with shaft 302 may be desirable or at least suitable for some applications.

In some embodiments, one or more suction/vacuum ports 317 may be provided on or about the tip or distal shaft. The port(s) may be fluidly coupled with a vacuum; the vacuum may comprise a pump or a negative pressure chamber or a syringe at the end of a fluid conduit. Other embodiments may comprise one or more suction/vacuum ports on any other suitable location on the TD, including but not limited to otherwise on the tip, and on the shaft. In some embodiments, a fluid delivery port 316 may be provided. In some embodiments the fluid delivery port may be coupled with a pump or high pressure fluid. In some embodiments the port may be perpetually open such that fluid may be delivered therethrough upon actuation of a pump or fluid pressure system. In other embodiments the port may be closed and selectively opened to deliver fluid therethrough. Other embodiments may comprise one or more fluid ports on any other suitable location on the TD, including but not limited to on the protrusions or otherwise on the tip, and on the shaft. Fluid ports that may be useful may comprise channels within the TD, polymer lines, hoses, etc. Fluids that may emanate from the outlet may comprise ionic fluids such as saline, medicines (including but not limited to antibiotics, anesthetics, antineoplastic agents, bacteriostatic agents, etc.), non-ionic fluids, and or gasses (including but not limited to nitrogen, argon, air, etc.). In some embodiments fluids may be under higher pressures or sprayed. It should be understood that although these elements (316 & 317) are not depicted in every one of the other figures, any of the embodiments described herein may include one or more such elements.

In the depicted embodiment, 318 represents an antenna, such as an RFID TAG or Bluetooth antenna configured to deliver a signal to a receiver unit. In embodiments in which antenna 318 comprises an RFID TAG, the RFID tag may comprise an RFID transponder. In other embodiments the RFID tag may comprise a passive tag. It should be understood that antenna 318 is not depicted in every one of the other figures, any of the embodiments described herein may comprise one or more such elements. Other embodiments may comprise one or more antenna(s) on any other suitable location on the TD, including but not limited to on the protrusions or otherwise on the tip, and on the shaft. In embodiments wherein antenna(s) 318 comprises an RFID transponder such transponder may comprise a microchip, such as a microchip having a rewritable memory. In some embodiments, the tag may measure less than a few millimeters. In some embodiments a reader may generate an alternating electromagnetic field which activates the antenna, such as an RFID transponder, and data may be sent via frequency modulation. In embodiments comprising one or more RFID tags (or other antenna) the position(s) of the RFID tag(s) or other antenna may be determined by an alternating electromagnetic field in the ultra-high frequency range. The position may be related to a 3 dimensional mapping of the subject. In an embodiment the reader may generate an alternating electromagnetic field. In some such embodiments, the alternating electromagnetic field may be in the shortwave (13.56 MHz) or UHF (865-869 MHz) frequency. Examples of potentially useful systems and methods for mapping/tracking a surgical instrument in relation to a patient's body may be found in U.S. Patent Application Publication No. 2007/0225550 titled "System and Method for 3-D Tracking of Surgical Instrument in Relation to Patient Body, which is hereby incorporated by reference in its entirety.

In some embodiments, a transmission unit may be provided that may generate a high-frequency electromagnetic field configured to be received by an antenna of the RFID tag or another antenna. The antenna may be configured to create an inductive current from the electromagnetic field. This current may activate a circuit of the tag, which may result in transmission of electromagnetic radiation from the tag. In some embodiments, this may be accomplished by modulation of the field created by the transmission unit. The frequency of the electromagnetic radiation emitted by the tag may be distinct from the radiation emitted from the transmission unit. In this manner, it may be possible to identify and distinguish the two signals. In some embodiments, the frequency of the signal from the tag may lie within a side range of the frequency of the radiation emitted from the transmission unit. Additional details regarding RFID technology that may be useful in connection with one or more embodiments discussed herein may be found in, for example, U.S. Patent Application Publication No. 2009/0281419 titled "System for Determining the Position of a Medical Instrument," the entire contents of which are incorporated herein by specific reference.

In other embodiments, antenna 318 may comprise a Bluetooth antenna. In such embodiments, multiple corresponding Bluetooth receivers at known locations may be configured to sense signal strengths from the Bluetooth antenna 318 and triangulate such data in order to localize the signal from the Bluetooth antenna 318 and thereby locate the TD within a patient's body. Other embodiments may be configured to use angle-based, electronic localization techniques and equipment in order to locate the antenna 318. Some such embodiments may comprise use of directional antennas, which may be useful to increase the accuracy of the localization. Still other embodiments may comprise use of other types of hardware and/or signals that may be useful for localization, such as WIFI and cellular signals, for example.

One or more receiver units may be set up to receive the signal from the tag. By evaluating, for example, the strength of the signal at various receiver units, the distances from the various receiver units may be determined. By so determining such distances, a precise location of the TD relative to a patient and/or a particular organ or other surgical site on the patient may be determined. In some embodiments, a display screen with appropriate software may be coupled with the RFID or other localization technology to allow a surgeon to visualize at least an approximate location of the tag, and therefore TD, relative to the patient's body.

Some embodiments may be further configured such that data from the antenna(s) may be used in connection with sensor data from the TD. For example, some embodiments of TDs comprising one or more sensors may be further configured with one or more RFID tags or other antenna(s). As such, data from the one or more sensors may be paired or otherwise used in connection with data from the one or more antenna(s). For example, some embodiments may be configured to provide information to a surgeon regarding one or more locations on the body from which one or more sensor readings were obtained. To further illustrate using another example, information regarding tissue concentration of a particular protein and/or nucleic acid may be combined with a location from which such tissue concentration(s) were taken. In this manner, a surgeon may be provided with specific information regarding which locations within a patient's body have been adequately sampled or otherwise found to contain the concentrations referenced aboveTD.

In some such embodiments, a visual display may be provided comprising an image of the patient's body and/or one or more selected regions of a patient's body. Such a system may be configured so as to provide a visual indication for one or more regions within the image corresponding to regions of the patient's tissue that have been sufficiently analyzed. For example, a display of a patient's liver may change colors at locations on the display that correspond with regions of the liver that have been detected to contain a specified range of hepatitis virus. Such regions may, in some embodiments, be configured such that pixels corresponding to particular regions only light up after the corresponding tissue in that region reaches a particular threshold concentration.

In some embodiments tip 301 may be attached to a robotic arm. In some embodiments, tip 301 and portion of shaft 302 may be attached to a robotic arm. In some embodiments tip 301 and/or a portion of shaft 302 and/or a portion shaft and/or portion of handle 303 may be attached to a robotic arm. In some embodiments, the robotic arm may comprise one or more motors such as a screw-drive motor, gear motor, hydraulic motors, etc. In some embodiments the robotic arm system may comprise worm gearheads, video cameras, motor control circuits, monitors, remote control devices, illumination sources, tactile interface, etc.

FIGS. 3k and 3L depict alternative embodiments of a TD in which cover 380 comprises one or more openings 380k in FIGS. 3K and 380L in FIG. 3L. The remaining elements shown FIGS. 3k and 3l may be similar or identical to embodiments depicted in FIGS. 3a-3j.

As shown in FIG. 3k, at least one opening 380k is/are present in cover 380. In some embodiments, cover 380 may be configured to at least substantially seal (other than opening(s) 380k) an interior space such that a vacuum applied via port 387 may result in suction through opening 380k. In the depicted embodiment, the opening(s) 380k may have a round shape. In the depicted embodiment, openings 380k may measure about 1.5 mm in diameter. In other embodiments, openings 380k may range in diameter from about 100 microns to about 100 mm. In other contemplated embodiments, openings 380k may have a variety of geometric shapes including but not limited to square, rectangular, and/or polygonal. In the depicted embodiment, sensor 389k may comprise a nanosensor. In some embodiments, cover 380 may be configured to at least substantially seal an interior space such that a vacuum applied via port 387 may result in suction through opening(s) 380k. In the depicted embodiment, seat 388 may elevate or decline to allow sensor 389k to approach and/or move away from opening 380k in order to increase and/or decrease contact with tissues and/or fluids that may be suctioned into the space inside of cover 380 and dock 384 when suction is applied via suction port 387. Actuators, not seen in this view but discussed elsewhere in this disclosure may be configured to move seat 388 and/or sensor 389k. When suction is applied via suction port 387, fluids and/or tissues external to cover 380 may be forced/pulled into contact with the edges of openings 380k and these may be further pulled through openings 380k with or without gross movement of the TD. Fluids and/or tissues that were previously external to the TD may be brought into contact with sensor 389k for analysis. Elements within the dock and cover space, not seen in this view but discussed elsewhere in this disclosure may be configured to move, stir, and/or alter the temperature of fluids within the dock and cover space to aid in incubation and/or analysis and/or reanalysis and/or cleaning and/or maintenance. Fluid entry into cover 380 may be facilitated or prevented by several factors including but not limited to size of openings, outside environment, tissue environment, and/or positive pressure of fluids/gasses from fluid delivery port 386 and/or vacuum from fluid extraction port 387.

The shaft of FIG. 3k further comprises antenna 318k. In the depicted embodiment, 318k represents an antenna configured to deliver a signal to a receiver unit. In some embodiments, antenna 318k may comprise any of the antennas described elsewhere herein including for example any of the antennas discussed in connection with antenna 318k. In embodiments in which antenna 318k comprises an RFID tag, the RFID tag may comprise an RFID transponder.

As shown in FIG. 3L, at least one opening 380L is/are present in cover 380. In the depicted embodiment the opening(s) 380L may have a round shape. In the depicted embodiment, openings 380L may measure about 1.5 mm in diameter. In the embodiment depicted in FIG. 3L, at least a portion of sensor 389L is allowed to protrude through a portion of the TD into the space external to the TD for body tissue and/or fluid sensing and/or sampling and/or testing. In other embodiments, openings 380L may range in diameter from about 100 microns to about 100 mm. In other contemplated embodiments openings 380L may have a variety of geometric shapes including but not limited to square, rectangular, and/or polygonal. For example, a rectangular shaped opening may allow for sensors deployed on a strip to pass through the opening. Sensors 389L deployed on a strip may pass through opening(s) 380L, as shown in FIG. 3L. A strip seen from the side view may look like a line. In some embodiments, the sensors and/or the material, that said sensors are deployed upon, are flexible. Flexibility may be helpful to maintain integrity of a sensor passing through an opening (in the cover and/or TD) into the external environment with or without agitation of the TD. In the depicted embodiment, sensor 389L is a nanosensor. In some embodiments, cover 380 may be configured to at least substantially seal an interior space such that a vacuum applied via port 387 may result in suction through opening(s) 380L. In FIG. 3L at least a portion of a sensor may protrude through an opening 380L in the TD to make contact with tissues and/or fluids outside of the TD. In the depicted embodiment, seat 388 may elevate or decline to allow sensor 389L to pass through opening 380L in order to contact tissues and/or fluids outside the cover and/or dock and/or TD and/or return back into the area under the cover adjacent to the dock. Actuators, not seen in this view but discussed elsewhere in this disclosure may be configured move seat 388 and/or sensor 389L. Fluid entry into cover 380 may be facilitated or prevented by several factors including but not limited to size of openings, outside environment, tissue environment, and/or positive pressure of fluids/gasses from fluid delivery port 386 and/or vacuum from fluid extraction port 387. Sensor 389L may receive and/or send one or more signals from and/or back to a processing unit to be analyzed while deployed outside of the cover and/or once retracted back under the cover. After sensor 389L is retracted back through the cover, it may be cleaned as discussed elsewhere in this disclosure.

Sensor 389L may be coupled with an antenna, which may send and/or receive one or more signals to/from a processing unit while sensor 389L is deployed outside of cover 380. Alternatively, or additionally, data from sensor 389L resulting from tissue and/or fluid analysis using sensor 389L may be stored locally and transmitted later. For example, a signal including such analysis data may be transmitted after sensor 389L has been retracted back under cover 380. As yet another alternative, such a signal may be transmitted following surgery. In such implementations, the signals need not necessarily be transmitted wirelessly. In fact, some embodiments may be configured to store data locally, after which a data module, such as a memory stick, may be removed from the TD/TDM and uploaded to a separate computer for analysis.

After sensor 389L is retracted back into cover 380, it may be cleaned, as discussed elsewhere in this disclosure. In other embodiments, at least a portion of sensor 389L may be positioned on a flexible roll and/or may be disposable. For example, some embodiments may comprise one or more flexible nanosensors 389L positioned on a flexible roll or stack such that portions of the roll/stack may protrude from a portion of cover 380, such as through opening(s) 380L, for analysis. Once a particular tissue/fluid analysis has been performed, some embodiments may be configured to wind the roll, flip the stack, and/or discard of the used portion of sensor 389L and/or to expose a new portion of sensor 389L for further analysis. Alternatively, used portion(s) of sensor 389L may be stored with the TD/TDM and discarded elsewhere following the procedure. In other embodiments, at least a portion of a flexible nanosensor 389L, such as a nanosensor on a flexible roll, may protrude from a portion of a TD/TDM without being manually extended/retracted through openings 380L. Flexible nanosensors may be obtained/manufactured by methods available to those of ordinary skill in the art, including but not limited to: Fabrication of Nanowire Electronics on Nonconventional Substrates By Water-Assisted Transfer Printing Method (Lee, Kim, Zheng; Nano Lett, 2011, 11(8):3435-9) and Vertical Transfer of Uniform Silicon Nanowire Arrays Via Crack Formation (Weisse, Kim, Lee, Zheng; Nano Lett 2011, 11(3): 1300-1305), which is hereby incorporated by reference in its entirety.

The shaft of FIG. 3L further comprises antenna 318L. In the depicted embodiment, 318L represents an antenna configured to deliver a signal to a receiver unit. In some embodiments, antenna 318L may comprise any of the antennas described elsewhere herein including for example any of the antennas discussed in connection with antenna 318L. In embodiments in which antenna 318L comprises an RFID tag, the RFID tag may comprise an RFID transponder.

An energy window 307 may be present on the upper side of the device. It is contemplated that in alternative embodiments, energy window 307 may be omitted. It should be noted that the term "energy window" is intended to encompass what is referred to as a planar-tissue-altering-window/zone in U.S. Pat. No. 7,494,488 and, as described later, need not be electrosurgically energized in all embodiments. In some embodiments, the "energy window" may comprise a variety of other energy emitting devices, including radiofrequency, intense pulsed light, LASER, thermal, microwave and ultrasonic. It should also be understood that the term "energy window" does not necessarily imply that energy is delivered uniformly throughout the region comprising the energy window. Instead, some energy window implementations may comprise a series of termini or other regions within which energy is delivered with interspersed regions within which no energy, or less energy, is delivered. This configuration may be useful for some implementations to allow for alteration of certain tissue areas with interspersed areas within which tissue is not altered, or at least is less altered. This may have some advantages for certain applications due to the way in which such tissue heals. A second energy window may also be included in some embodiments, and may comprise an ultrasonic or another variety of energy emitting device.

In some embodiments, one or more sensors such as for example sensors 310 and 314 may be positioned on the device. The sensors 310 and 314 may comprise any of the sensors described in the specification herein. Other embodiments may comprise one or more sensors on any other suitable location on the TD, including but not limited to on the protrusions or otherwise on the tip, and on the shaft. Sensors that may be useful include thermal sensors, photo-electric or photo optic sensors, cameras, etc. In some embodiments, one or more sensors may be used to monitor the local post passage electrical impedance or thermal conditions that may exist near the distal tip of the shaft or on the tip. Some embodiments may also comprise one or more sensors incorporating MEMS (Micro Electro-Mechanical Systems) technology, such as MEMS gyroscopes, accelerometers, and the like. Such sensors may be positioned at any number of locations on the TD, including within the handle in some embodiments. In some embodiments, sensor 314 may comprise fiberoptic elements. In an embodiment, the sensor can be configured to sense a temperature of tissue adjacent to the apparatus. The temperature sensor may alternatively be configured or sense a temperature of one or more fluids adjacent to the apparatus such as for example tissue fluids and/or fluids introduced by the surgeon.

Temperature and impedance values may be tracked on a display screen or directly linked to a microprocessor capable of signaling control electronics to alter the energy delivered to the tip when preset values are approached or exceeded. Typical instrumentation paths are widely known, such as thermal sensing thermistors, and may feed to analog amplifiers which, in turn, feed analog digital converters leading to a microprocessor. In some embodiments, internal or external ultrasound measurements may also provide information which may be incorporated into a feedback circuit. In an embodiment, an optional mid and low frequency ultrasound transducer may also be activated to transmit energy to the tip and provide additional heating and may additionally improve lysing. In some embodiments, a flashing visible light source, for example, an LED, can be mounted on the tip may show through the tissues and/or organs to identify the location of the device.

In some embodiments, one or more electromagnetic delivery elements 315 may be positioned on tip or shaft. Other embodiments may comprise one or more electromagnetic delivery elements on any other suitable location on the TD, including but not limited to on the protrusions or otherwise on the tip, and on the shaft. Electromagnetic delivery elements that may be useful include: LEDs, LASERs, fiberoptics, filaments, photoelectric materials, infrared emitters, etc.

A second energy window 308 may also be included in some embodiments, and may comprise yet another ultrasonic energy emitter or another variety of energy emitting device. An ultrasonically energized energy window 308 may be present on the upper side of the device. It is contemplated that in alternative embodiments, energy window 308 may be omitted. It should be noted that the term "energy window" is intended to encompass what is referred to as a planar-tissue-altering-window/zone in U.S. Pat. No. 7,494,488 and, as described later, need not be ultrasonically energized in all embodiments. In some embodiments, the "energy window" may comprise a variety of other energy emitting devices, including ultrasonic, intense pulsed light, LASER, thermal, microwave and electrical. It should also be understood that the term "energy window" does not necessarily imply that energy is delivered uniformly throughout the region comprising the energy window. Instead, some energy window implementations may comprise a series of energy delivering elements or other regions within which energy is delivered with interspersed regions within which no energy, or less energy, is delivered. An ultrasonic energy window configuration may be useful for some implementations, depending upon piezoelectric component and/or energy applied to less aggressively disrupt tissues (in order to possibly increase the concentration of target chemicals and/or biological compounds) at the cellular level to increase the availability of biological and/or chemical components to be sensed/analyzed and/or (may be at higher energy levels) to allow for alteration and/or damage to targeted tissues and/or heating for treatment. Energy window 308 may only be at least substantially planar, or may take on other cross-sectional shapes that may correspond with a portion of the shape of the shaft, such as arced, stair-step, or other geometric shapes/curvatures.

A second energy window 308 may also be included in some embodiments, and may comprise yet another ultrasonic energy emitter or another variety of energy emitting device. An ultrasonically energized energy window 307 may be present on the upper side of the device. It is contemplated that in alternative embodiments, energy window 307 may be omitted. It should be noted that the term "energy window" is intended to encompass what is referred to as a planar-tissue-altering-window/zone in U.S. Pat. No. 7,494,488 and, as described later, need not be ultrasonically energized in all embodiments. In some embodiments, the "energy window" may comprise a variety of other energy emitting devices, including radiofrequency, intense pulsed light, LASER, thermal, microwave and electrical. It should also be understood that the term "energy window" does not necessarily imply that energy is delivered uniformly throughout the region comprising the energy window. Instead, some energy window implementations may comprise a series of energy delivering elements or other regions within which energy is delivered with interspersed regions within which no energy, or less energy, is delivered. An ultrasonic energy window configuration may be useful for some implementations, depending upon piezoelectric component and/or energy applied to less aggressively disrupt tissues (in order to possibly increase the concentration of target chemicals and/or biological compounds) at the cellular level to increase the availability of biological and/or chemical components to be sensed/analyzed and/or (may be at higher energy levels) to allow for alteration and/or damage to targeted tissues and/or heating for treatment. Energy window 307 may only be at least substantially planar, or may take on other cross-sectional shapes that may correspond with a portion of the shape of the shaft, such as arced, stair-step, or other geometric shapes/curvatures.

FIG. 3bb, depicts an alternative embodiment of a TD dock 384bb. In the embodiment depicted in FIG. 3bb, the cover may comprise a portion of the shaft and/or tip. More specifically dock 384bb is positioned within a hollow opening formed inside the shaft 302bb and/or tip 301bb. In an embodiment, the dock may be exposed by separating a portion of the shaft from an adjacent portion off the shaft or an adjacent portion of the tip in a telescoping fashion in order to expose the dock.

Figures 4A, 4B:
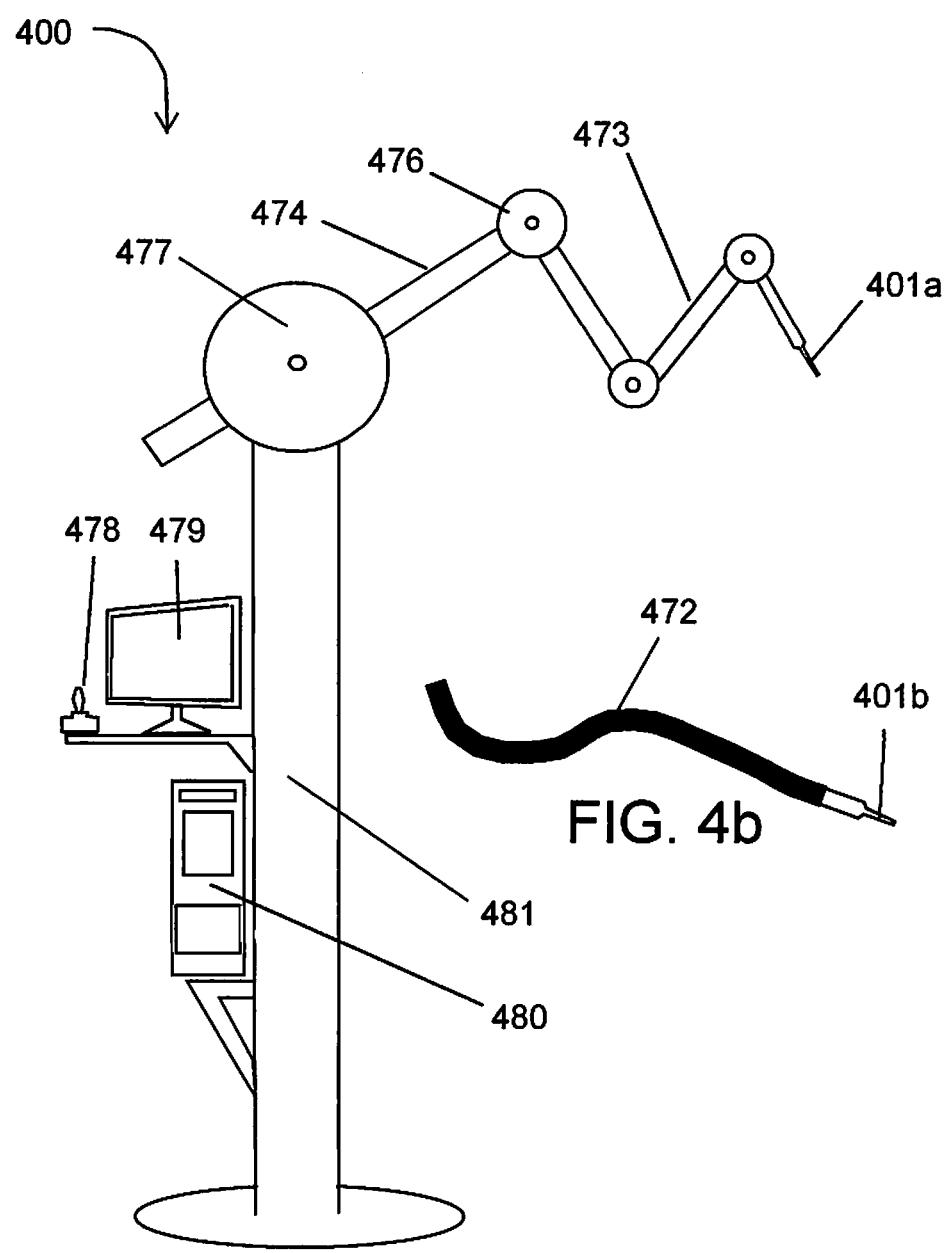

An embodiment of a system 400 for performing robotic surgery using a TD is depicted in FIG. 4a. System 400 may comprise a tissue dissecting wand (TD) 401. TD 401 may comprise a tissue dissecting wand (TD) that may, as described elsewhere herein, comprise a plurality of protrusions with one or more recessions positioned therebetween. TD 401 may be coupled with one or more robotic surgery components, such as a surgical arm. Tip 401a may comprise any of the specific embodiments of TD/TDM and/or the tips on any such TD/TDM's.

In some embodiments, TD 401 may comprise a shaft, a tip, and/or a handle, as described elsewhere in this disclosure. In such embodiments, TD 401 may be selectively coupled to a robotic arm such that the TD 401 can either be used by hand, or coupled with one or more robotic surgery components to allow a surgeon to perform a surgical procedure with the TD 401 remotely and/or indirectly. In other embodiments, the TD may be configured to be integrally coupled with, or otherwise non-selectively coupled with, one or more robotic surgery components. In such embodiments, it may not be necessary to configure the TD 401 with a handle and/or shaft. In other words, in some embodiments, the TD 401 may comprise only a tip.

In some embodiments, the robotic surgery system 400 may comprise one or more motors, such as a screw-drive motor, gear motor, hydraulic motors, etc. In some embodiments, the robotic surgery system 400 may comprise worm gearheads, video cameras, motor control circuits, monitors, remote control devices, illumination sources, tactile interface, etc. In the embodiment depicted in FIG. 4a, TD 400 comprises a TD tip 401a that is positioned at the end of a robotic arm. This robotic arm comprises a plurality of arm segments 473 with corresponding joints 476 positioned therebetween. A primary joint 477 may be positioned to support and articulate together each of the arm segments 473 and smaller joints 476. Primary joint has a primary arm segment 474 that extends therefrom. Finer movements of the robotic arm may then be accomplished using one or more of the smaller joints 476. A stand 481 may also be provided to support the various robotic arms. In some embodiments, stand 481 may also be configured to support a monitor 479 and/or other display, input, or control components, such as a control element 478. In some embodiments, control element 478 may comprise a hand control toggle 478. In other embodiments, control element 478 may comprise a keyboard, mouse, touchscreen display, virtual reality system, control pad, or the like. Monitor 479 and/or control element 478 may be communicatively coupled with a central processing unit 480.

Central processing unit 480 may comprise, for example, one or more microprocessors and/or other electronic components, such as data connectivity elements, memory, non-transitory computer readable media, etc. In some embodiments, central processing unit 480 may comprise a general-purpose computer. Central processing unit 480 may further comprise a machine-readable storage device, such as non-volatile memory, static RAM, dynamic RAM, ROM, CD-ROM, disk, tape, magnetic storage, optical storage, flash memory, or another machine-readable storage medium. In some embodiments information from antennae and/or sensors is accessed and/or processed by the central processing unit to guide the robotic arm and/or TD.

FIG. 4b illustrates an alternative embodiment of a robotic arm 472 that may be used with system 400. Robotic arm 472 comprises an endoscopic snake-like robotic arm 472 and also comprises a TD 401b positioned at its distal end. As with the embodiment of FIG. 4a, TD 401b may be selectively coupled to robotic arm 472 or, alternatively, may be integrally or otherwise non-selectively coupled to robotic arm 472. Further details regarding robotic surgery components that may be useful in connection with the various embodiments disclosed herein may be found in the following U.S. Patent Nos., each of which is hereby incorporated by reference in its entirety: U.S. Pat. No. 4,259,876 titled Mechanical Arm, U.S. Pat. No. 4,221,997 titled Articulated Robot Arm and Method Of Moving Same, U.S. Pat. No. 4,462,748 titled Industrial Robot, U.S. Pat. No. 4,494,417 titled Flexible Arm, Particularly a Robot Arm, U.S. Pat. No. 4,631,689 titled Multi-Joint Arm Robot Apparatus, U.S. Pat. No. 4,806,066 titled Robotic Arm, U.S. Pat. No. 5,791,231 titled Surgical Robotic System and Hydraulic Actuator Therefor, U.S. Pat. No. 7,199,545 titled Robot For Surgical Applications, U.S. Pat. No. 7,316,681 titled Articulated Surgical Instrument For Performing Minimally Invasive Surgery With Enhanced Dexterity and Sensitivity, U.S. Pat. No. 8,182,418 titled Systems and Methods for Articulating An Elongate Body, U.S. Pat. No. 8,224,485 titled Snaking Robotic Arm With Movable Shapers.

In contemplated embodiments, the embodiments mentioned during the discussion of FIGS. 4a and 4b may be used with the tip geometries of embodiments discussed with FIGS. 1 and 3 as well as alternative embodiments, for example, where the geometry of the tip area may comprise protrusions that are not oriented along the axis of the shaft (as seen from a top view); some of these alternative embodiments for tip area geometries are depicted in FIG. 5a, b, c, d.

Any of the embodiments of TD and/or TDM discussed above including, but not limited to, the embodiments discussed with FIG. 1a-L, FIG. 2a-L, FIG. 3a-L, etc. may be used in conjunction with one or more of the robotic surgery elements disclosed in connection with FIG. 4a and/or 4b. Tip(s) 401a and/or 401b may comprise any of the specific embodiments of TD/TDM and/or the tips on any such TD/TDM's In FIG. 5a, b, c, d, the tips depicted are contemplated to be able to be used with any of the embodiments discussed herein. Said tips are not intended to be restricted to symmetry and/or pattern and/or dimension. In other embodiments said tips may be asymmetrical or lacking protrusions and/or lysing segments on one side or another.

FIG. 5a is an upper plan view illustrating the protrusions and lysing segments of an embodiment of a tissue dissector, wherein some of the protrusions and lysing segments are oriented in a non-axial direction. This embodiment comprises a plurality of axial protrusions 504a (axially meaning at least substantially parallel to an axis of a corresponding TD shaft). This embodiment further comprises a plurality of non-axial protrusions 551a along the right side of the tip and a plurality of non-axial protrusions positioned along the left side of the tip. The tip further comprises two non-axial corner protrusions 554a. The tip further comprises a plurality of recessions. One or more of the recessions may further comprise a lysing segment 553a.

In this embodiment, non-axial protrusions 551a extend in a direction that is at least substantially perpendicular to the direction in which axial protrusions 504a extend. More particularly, there are two sets of non-axial protrusions 551a (one depicted on the right side and one on the left side of the embodiment of FIG. 5a). Both sets of non-axial protrusions 551a extend in directions that are at least substantially perpendicular to the direction in which axial protrusions 504a extend (namely, along a longitudinal axis of the TD tip). In addition, it can be seen in FIG. 5a that the two sets of non-axial protrusions 551a extend in directions that are at least substantially opposite from one another.

In some embodiments, axial protrusions 504a may extend at least substantially along a longitudinal axis of the shaft, as described above, and non-axial protrusions 551a may extend at an angle of between zero degrees and 30 degrees of a normal to the direction in which the axial protrusions 504a extend. It is contemplated that it may be desirable for some implementations and embodiments to provide non-axial tips extending in a direction or directions falling within this range in order to, for example, allow a surgeon to effectively perform both a to and fro, and a side-to-side ("windshield wiper") motion using the TD and/or TDM.

In some embodiments, the tip may measure about 1 cm in width and about 1-2 mm in thickness. Sizes of about one-fifth to about five times these dimensions may also have possible uses.

In some embodiments, the tip can be a separate piece that is secured to the shaft by a variety of methods such as a snap mechanism, mating grooves, plastic sonic welding, etc. Alternatively, in some other embodiments, the tip can be integral or a continuation of a shaft made of similar metal or materials. In some embodiments, the tip may also be constructed of materials that are both electrically non-conductive and of low thermal conductivity; such materials might comprise, for example, porcelain, ceramics, glass-ceramics, plastics, varieties of polytetrafluoroethylene, carbon, graphite, and/or graphite-fiberglass composites. In some embodiments, the tip may be constructed of a support matrix of an insulating material (e.g., ceramic or glass material such as alumina, zirconia). External power control bundles as previously described in other embodiments may connect to electrically conductive elements to bring RF electrosurgical energy from an electrosurgical generator down the shaft to electrically conductive lysing elements 553a mounted in the recessions in between the protrusions 551a. In some embodiments, the protrusions may comprise bulbous protrusions. In some embodiments the tip may have between 3 and 100 non-axial protrusions and relative recessions. In the depicted embodiment, the tip 501a may alternatively be made partially or completely of concentrically laminated or annealed-in wafer layers of materials that may include plastics, silicon, glass, glass/ceramics, cermets or ceramics. Lysing elements 553a may also be made partially or completely of a cermet material. Alternatively, in a further embodiment the tip may be constructed of insulation covered metals or electroconductive materials. The lysing segments may be located at the termini of conductive elements.

In the depicted embodiment, tip 501a which terminates in protrusions such as 504a and 551a may be made of materials that are both electrically non-conductive and of low thermal conductivity such as porcelain, epoxies, ceramics, glass-ceramics, plastics, or varieties of polytetrafluoroethylene. Alternatively, the tip may be made from metals or electroconductive materials that are completely or partially insulated. In some embodiments, the electrically conductive tissue lysing element(s) 552a may have any geometric shape including a thin cylindrical wire, and may be positioned within the relative recessions of the tip. The electrically conductive lysing element can be in the shape of a plate or plane or wire and made of any metal or alloy that does not melt under operating conditions or give off toxic residua. Optimal materials may include but are not limited to steel, nickel, alloys, palladium, gold, tungsten, silver, copper, and platinum. Metals may become oxidized thus impeding electrical flow and function.

FIG. 5b is an upper plan view illustrating the protrusions and lysing segments of another embodiment of a tip area of a tissue dissector. This embodiment may comprise a plurality of axial protrusions 504b and a plurality of non-axial protrusions 551b. In addition, this embodiment comprises two transitional or corner protrusions 554b. A plurality of recessions 552b are also depicted, one or more of which may comprise corresponding lysing segments 553b.

Figures 5C, 5D:
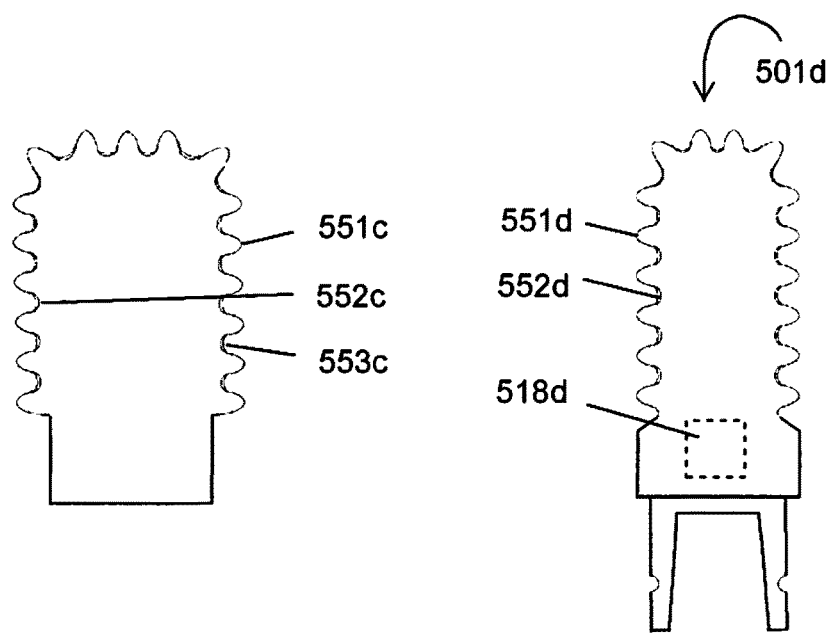
FIG. 5c is an upper plan view of an alternative embodiment of a tissue dissector, wherein some of the protrusions and lysing segments are oriented in a non-axial direction.
FIG. 5d is a lower plan view of an alternative embodiment of a tissue dissector, wherein some of the protrusions and lysing segments are oriented in a non-axial direction and an antenna is present.

FIG. 5c is an upper plan view illustrating the protrusions and lysing segments of an embodiment of a tip area of a tissue dissector. This embodiment comprises a plurality of axial protrusions; this embodiment further comprises a plurality of non-axial protrusions 551c along the right side of the tip and a plurality of non-axial protrusions positioned along the left side of the tip. The tip further comprises two non-axial corner protrusions. The tip further comprises a plurality of recessions 552c. One or more of the recessions may further comprise a lysing segment 553c.

FIG. 5d is a lower plan view illustrating the protrusions and lysing segments of another embodiment of a tip area of a tissue dissector. This embodiment may comprise a plurality of axial protrusions and a plurality of non-axial protrusions 551d. In addition, this embodiment comprises two transitional or corner protrusions. A plurality of recessions 552d are also depicted, one or more of which may comprise corresponding lysing segments. The tip of FIG. 5d further comprises antenna 518d. In the depicted embodiment, 518d represents an antenna configured to deliver a signal to a receiver unit. In some embodiments, antenna 518d may comprise any of the antennas described elsewhere herein including for example any of the antennas discussed in connection with antenna 118. (PASTE into TDM) In embodiments in which antenna 518d comprises an RFID tag, the RFID tag may comprise an RFID transponder.

Some embodiments may be further configured such that data from the antenna(s) used in connection with sensor data from the TD. For example, some embodiments of TDs comprising one or more sensors may be further configured with one or more antenna(s). As such, data from the one or more sensors may be paired or otherwise used in connection with data from the one or more antenna(s). For example, some embodiments may be configured to provide information to a surgeon regarding one or more locations on the body from which one or more sensor readings were obtained. To further illustrate using another example, information regarding tissue concentration of a particular protein and/or DNA may be >>>>>>>>.

Figure 6:
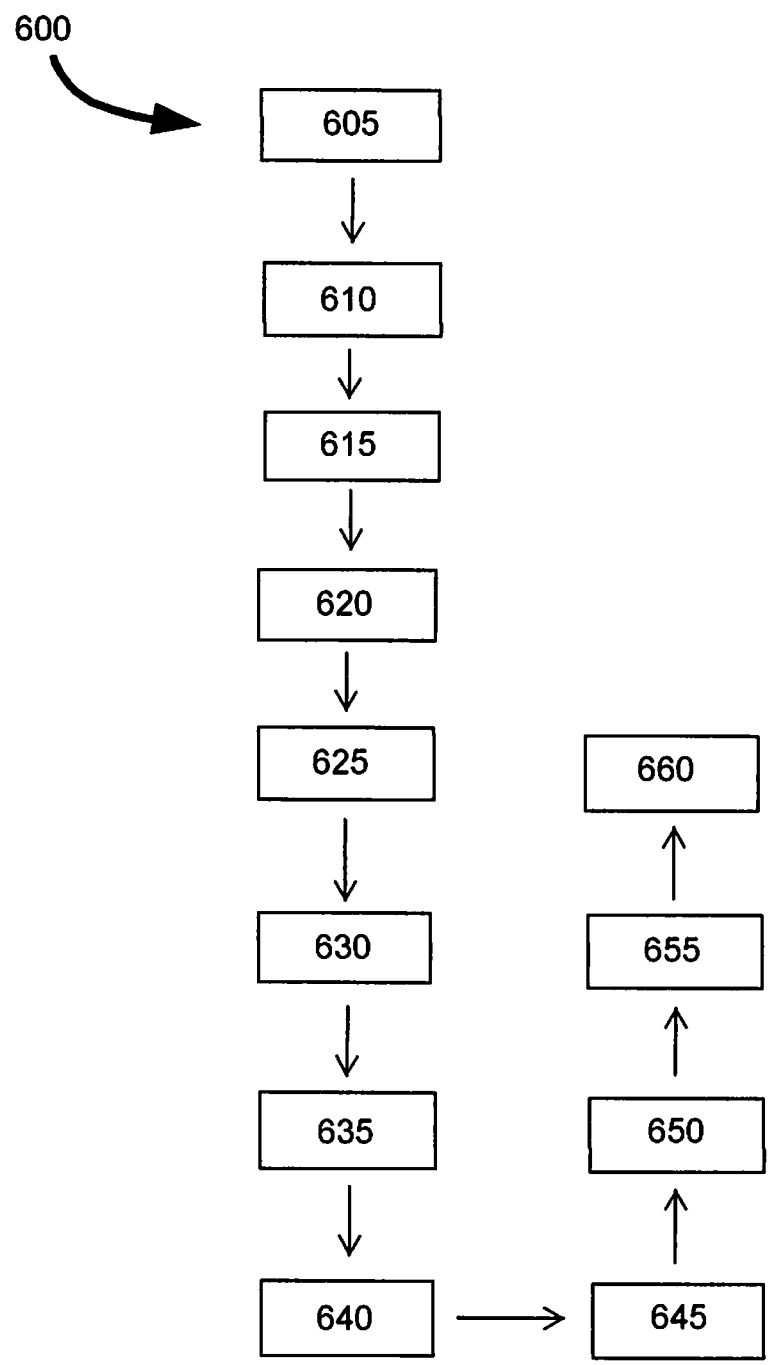
FIG. 6 is a flow chart illustrating one implementation of a method of a method of use for the apparatus depicted in FIG. 1a-j for tissue/fluid sampling and/or analysis.

FIG. 6 is an example of an implementation of a method 600 of use according to this disclosure for the apparatus depicted in FIG. 1 a-j for tissue/fluid sampling and/or analysis using a sensor may be as follows. A nanosensor capable of detecting a given biochemical and/or biomarker may be sterilely placed in the dock of a sterile TD. The patient may be cleansed and anesthetized and an entrance incision may be made. Step 605 may comprise inserting the TD into the patient and directing the TD toward the target tissues to be sampled and/or analyzed. Step 610 may comprise activating the antenna/antennae and an accompanying CPU to track the location of the sensor and TD. Step 615 may comprise in some implementations, activating fiberoptics and/or a camera to provide further data, such as visual data, regarding the location of the sensor and TD. Step 620 may comprise once the TD is in a desired location for tissue sampling/analysis, introducing one or more fluids to facilitate tissue sampling and/or analysis into the space between the cover and dock if desired.

Step 625 may comprise exposing the sensor. In some implementations, the sensor may be exposed by opening and/or retracting the cover. In some implementations, the sensor may be exposed by protruding at least a portion of the sensor through openings in the cover, as discussed elsewhere herein. Step 630 may comprise positioning the sensor at a desired location/angle to improve desired contact with target body fluids and/or tissues. In some implementations, this positioning/angling may increase contact between such target fluids/tissues. In some implementations, the sensor(s) may be positioned at a desired location/angle using actuators. Step 635 may comprise agitating and/or vibrating the TD to further improve desired contact between the sensor(s) and the target fluids/tissues. For example, in embodiments comprising vibration means, such means may be activated to vibrate the sensor and thereby improve contact and/or tissue sampling. As discussed elsewhere herein, such vibration means may be positioned on or adjacent to the handle in order to provide suitable vibration without causing undesirable tissue damage.

Step 640 may comprise allowing the sensor(s) to remain in contact with the specimen in the target zone until an accurate and/or stable reading is obtained. In some implementations, the sensor(s) may be configured to maintain such contact for a predetermined amount of time. In some implementations of method 600 allowing the sensor to remain in contact with the specimen may comprise maintaining such contact for a predetermined amount of time. Step 645 may comprise making the sensor unexposed. In implementations in which the sensor(s) is protruded, step 645 may comprise retracting the sensor back into the cover. In implementations in which the cover was opened, step 645 may comprise closing the cover. Step 650 may comprise processing the collected biomaterial and/or sensor data. If further processing of the collected material and/or sensor data is necessary while the TD is still at the target zone then such processing may take place within the dock after sampling. In some implementations, one or more external fluids and/or reagents may be delivered into the dock to facilitate chemical reactions and/or interactions.

Step 655 may comprise cleaning the sensor, such as cleaning for re-use at the next target site. In some implementations, one or more fluids, such as cleaning agents (or just water) may be introduced in the dock to facilitate such cleaning. Such fluids may also be extracted from the dock using vacuum ports, as described elsewhere herein, if needed.

Step 660 may comprise readying a sensor for another procedure. In some implementations the regeneration may be combined with the cleaning step. In some implementations, step 660 may comprise regenerating the existing sensor. In other implementations step 660 may comprise exposing a new sensor. Once the sensor has been regenerated or a new sensor has been exposed, the TD/TDM may be moved and/or tracked to the next target site by the surgeon and the process repeated for additional sampling/analysis.

Figure 7:
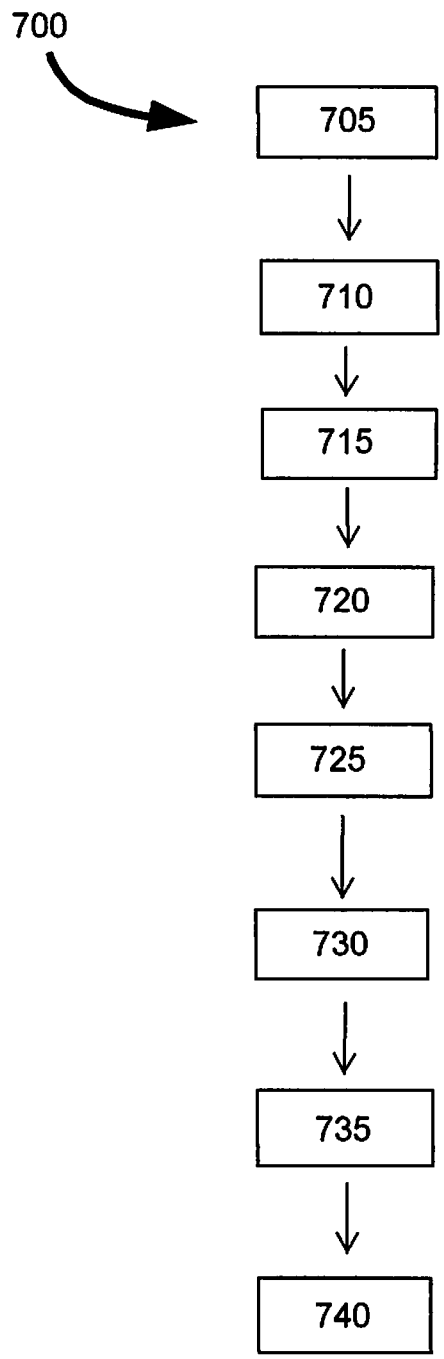
FIG. 7 is a flow chart illustrating one implementation of a method for accessing an organ with the assistance of a TD.

One implementation of a method 700 according to this disclosure for accessing an organ with the assistance of a TD is shown in FIG. 7. In some implementations, surgeon(s) may need to access tissue and/or an organ to repair or treat it. In some implementations, the skin surrounding the anticipated entrance wound for the surgical area may be cleansed by, for example, with isopropyl alcohol (degreaser) followed by germicidal chlorhexidine scrub. Then, a local anesthetic may be applied (such as by injecting) 1% lidocaine+1:10,000 adrenaline to the skin.

Step 705 may comprise, for minimally invasive procedures or minimally invasive entrance wounds, performing a limited incision to allow passage of the maximal width of the tip or shaft of the TD. Step 705 may be performed with, for example, a #15 Bard-Parker™ Scalpel. This incision may be deepened by scalpel, scissors or other surgical instrument to enter the desired body structure or cavity. For larger approaches, such as open abdominal surgery or trauma surgery step 705 may comprise the initial skin opening or body cavity opening steps of such a procedure. In some implementations, step 710 may comprise making the skin incision using the lysing segments of the TD. Step 710 may comprise: applying one or more fluids to the tissues. In some implementations, step 710 may comprise applying fluids to the target tissue(s). In some implementations, step 710 may comprise applying fluids to the tissues to be traversed en route to the target tissue, in addition to, or as an alternative to applying fluids directly to the target tissue(s). In some implementations, the fluid(s) may comprise water. In some implementations, the fluid(s) may comprise an ionic fluid, such as a saline solution. The fluid(s) may be applied to the tissue via, for example, injection, or TD fluid port or via a separate cannula or catheter or via pouring or via spray. In some implementations, the fluid(s) may comprise an ionic fluid and an anesthetic, such as a tumescent anesthesia. Non-ionic fluids may be used in other implementations; such fluids may become more ionic by diffusion of some of the patients' ions present in the surgical field. In some implementations step 710 may comprise applying one or more fluids that serve as an ionic fluid, and/or an anesthetic, and/or adrenaline. In some such implementations, the fluid(s) may comprise a Klein Formula. In some implementations, the Klein formula and amount used may be about 100 cc of Klein Formula with saline, 0.1% lidocaine, epinephrine 1:1,000,000, and NaHCO3 @5 meq/L of saline).

Step 715 may comprise: passing the TD through the various layers of tissue to create a path to a target organ. In some implementations, creating a path to a target organ or other target tissue may comprise creating a path from the incision to the target organ or other target tissue and/or creating a path around the target organ or other target tissue to allow for access to other regions of the target organ or other target tissue. In some implementations step 715 may further comprise activating the lysing segments and/or energy window to reduce bleeding or tissues traversed on the way to the target organ. In some implementations, the lysing segments and/or energy window may be used to induce fibrosis along the path, including along a path that may traverse the perimeter of the target organ/tissue. In some implementations, the TD and/or the anticipated path may be visualized using for example an endoscope, a fiberoptic or camera, an antenna(s) or other such device. In some implementations, such a device or devices may be positioned on the TD. In other implementations such a device or devices may be separate from the TD. In some implementations, heat may be produced or energy may otherwise be released in the tissues through which the TD is passed. In some implementations, heating portions of the tissues the TD passes by may be undesirable. As such, in some implementations, undesirable heating of such layers may be mitigated by applying a cooling step antecedent and or concurrent with energy delivery with the TD. Such steps may comprise use of one or more cooling fluids delivered via the TD or one or more separate catheters or cannulas or endoscopes. Such cooling mechanism(s) may comprise for example, a closed water bag. Such a bag may be at a temperature of less than 37° C. In some implementations, cooling objects such as fluid or gel filled bags may be used that may range in temperature between about 1° C. to about 20° C. In some such implementations, the fluid or gel may be about 15° C. Other cooling mechanisms may comprise a dynamic cooling system wherein a cool liquid or gel is actively pumped into or through a contact cooling object. Step 720 may comprise identifying important blood vessels, nerves, ducts, organs or other anatomy in the area surrounding the target tissue. Step 725 may comprise: adding additional fluids of the types previously described to the target and/or surrounding tissues via the TD port(s) or via one or more separate catheters or cannulas or endoscopes. Step 730 may comprise: expanding one or more regions of the path to the target tissue. In some implementations, step 730 may comprise expanding one or more path(s) from the incision to the target tissue. In some implementations, step 730 may comprise expanding a region around the target tissue such as for example, via a fanning motion. In some implementations, one or more of the other steps described herein using the TD may also be performed with a fanning motion. In implementations using TDs with axially oriented protrusions, such a fanning motion may comprise a to and from spokewheel pattern. In implementations using TDs with nonaxially oriented protrusions, such a fanning motion may comprise a side-to-side fanning motion; one example of a fanning motion using a TD having at least one nonaxially oriented protrusion may comprise a 'windshield wiper' motion. In some implementations, step 730 may further comprise activating the energy to the TD for example the energy to the lysing segments and/or one or more energy windows. Step 735 may comprise: observing for bleeding from larger vessels and achieving hemostasis as needed. In some implementations achieving hemostasis may be accomplished by cautery, electrifying, ligating, or chemical methods. In some implementations, the lysing segment and/or the energy window can be used to achieve the hemostasis. In some implementations, one or more other devices and/or suture and/or surgeon's hands may be used to achieve hemostasis for larger vessels. Step 740 may comprise: removing the TD with power off and suturing the wound in the standard fashion. In some implementations, the tissues traversed may require closure by suturing and/or stapling. In some implementations, organs and/or organ systems that the TD may be useful to access may include but not limited to muscle, and/or parotid, and/or salivary gland, and/or thyroid, and/or lung, and/or heart, and/or gastrointestinal, and/or liver, and/or pancreas, and/or spleen, and/or gallbladder, and/or kidney, and/or adrenal, and/or prostate, and/or ovary, and/or uterus, and/or bladder, and/or vascular, and/or lymph nodes and/or skeleton, and/or lung.

Figure 8:
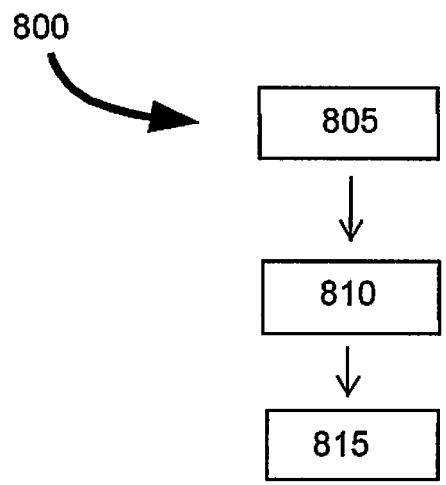
FIG. 8 is a flow chart illustrating an implementation of a method for sampling and/or testing tissue
Figure 9:
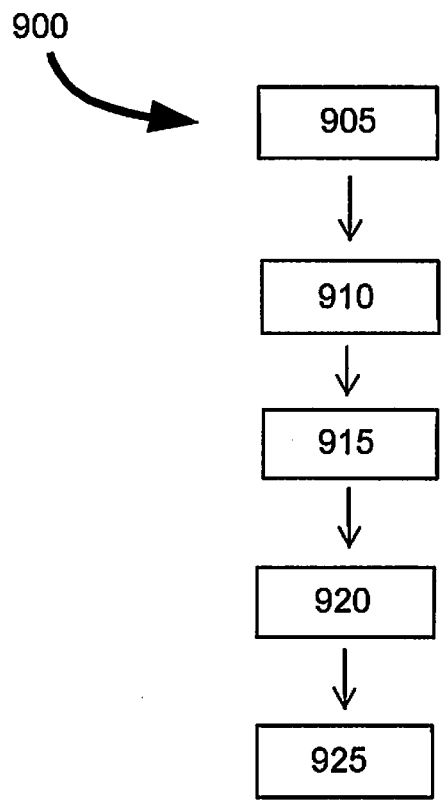
FIG. 9 is a flow chart illustrating an implementation of a method comprising detection functionality.

FIG. 8 depicts a flow chart of an implementation of a method 800 for sampling and/or testing tissue using a TD. In this particular implementation, the use of combined data from the tissue dissecting wand generated from at least the sensor and the antenna(s) may be used to provide suitable feedback to a user during treatment. In some implementations, the TD Wand may comprise a tip comprising a plurality of protrusions. One or more lysing segments may be positioned between at least two adjacent protrusions among the plurality of protrusions. A sensor, such as a nanosensor, may be positioned on the TD. The sensor may be configured to sense a concentration of a chemical and/or biological compound contained in at least one of tissue and fluid adjacent to the tissue dissecting wand during an operation. The fluid of which a concentration of a chemical and/or biological compound reading is taken may comprise, for example, fluid from adjacent tissue(s) and/or fluid introduced during the procedure by way of the TD and/or another device or procedure. The TD may also comprise an antenna(s) such as an RFID tag positioned on the TD. In some implementations, the antenna(s) may be positioned on the tip and/or distal end of the shaft, such as on a bottom surface of the tip and/or distal end of the shaft. The antenna(s) may be configured to provide location data regarding a location of the TD, such as a particular portion or region of the TD for example, during an operation or procedure. Although method 800 is shown in the figure beginning with step 805, it should be understood that any of the preliminary steps described above in connection with other implementations may be performed in method 800 as well. For example, one or more of steps (705-730) from method 700 may be performed in method 800 if desired. Similarly, one or more other steps of any of the other implementations described herein may also be included in the method depicted in FIG. 18. In some implementations, step 805 may comprise: receiving data from the tissue dissecting wand sensor. Step 810 may comprise receiving data from the antenna(s) such as RFID tag data. Step 815 may comprise combining the data generated from at least the sensor and the antenna(s). In some implementations, the data from the sensor and the antenna(s) may be combined before it is received. In other words, a step of "receiving combined data from the tissue dissecting wand generated from at least the sensor and the antenna(s) may comprise receiving precombined data (data from the sensor and the antenna(s) that was combined before it was received) or, alternatively, may comprise separately receiving sensor data and antenna(s) data that may be combined to allow for one or more particular features or functionalities. The combined data may be used to allow a surgeon or other user to determine one or more regions within a patient's body that have been adequately tested and or sampled using the TD wand. For example, in some implementations, the combined data may allow a user to visualize one or more regions within a patient's body, such as one or more regions that have been sufficiently treated. This may be accomplished, for example, by creating an image corresponding with one or more regions of a patient's body. Such image or images may be highlighted, receive color changes, or otherwise modified on a display to indicate to the user which regions have been adequately tested and or sampled. In some implementations, such regions may correspond with regions comprising tissue that has reached a predetermined threshold chemical and/or biological compound and/or biomarker concentration.

Some embodiments may be configured with a detector and/or optical scanner configured to detect reflected light from a particular organ or tissue. For example, some embodiments may be configured to emit and direct light or another electromagnetic radiation to an organ or tissue and scan the reflected light to assess the type of organ/tissue that reflected the light/radiation. Some such embodiments may comprise, for example, a polarized multispectral light scattering/scanning system, such as are disclosed in U.S. Patent Application Publication No. 2012/0041290 titled "Endoscopic Polarized Multispectral Light Scattering Scanning Method," which is hereby incorporated by reference in its entirety.

In some such embodiments, data from the detector/scanner may be coupled with data from one or more other devices/components, such as an RFID tag or another antenna, to provide addition detail/information to a surgeon during a procedure with the TD/TDM. For example, in some embodiments comprising a light detector/scanner, as described above, data from the reflected radiation source may be used to identify an organ adjacent to the TD/TDM. This data may be combined with location data from the antenna in order to provide precise information to a surgeon regarding a current location of the TD/TDM within a patient's body and its location in relation to a detected organ or tissue. For example, a surgeon might be provided with visual and/or audible information indicating that the TD/TDM is approaching or being withdrawn from the liver. In some embodiments, the surgeon may be provided with additional detail, such as the current distance to the organ, directions for reaching the organ without causing undue harm to other organs/tissues along the way, etc. In some embodiments, one or more of the sensors 110, 114, 210, 214, 310, and/or 314 may comprise such a detector/scanner. In some embodiments, some of the processing of reflected radiation may be done on the TD/TDM. In other embodiments, however, the TD/TDM may simply comprise one or more fiber optic elements, as discussed elsewhere herein, which may be configured to receive the reflected radiation and transfer it outside of the body to another system, such as a computer system configured to process data gathered from analysis of the reflected radiation. In some embodiments, the one or more fiber optic elements may also be configured to emit the radiation to be reflected. Alternatively, additional fiber optic elements and/or other radiation-emitting elements may be provided for this purpose.

Examples of electromagnetic reflectance technology that may be useful for some of the embodiments disclosed herein such as for electromagnetic delivery element(s) 115 and/or sensors 110, 114, 210, 214, 310, and/or 314 may be found in Laser Reflectance Imaging of Human Chest for Localization of Internal Organs (Contact Fiber Probes For In-Vivo Optical Spectroscopy (Kumaravel, Singh; Biomedical Engineering, IEEE, 2010, 57(5) 1167-1175.) which is hereby incorporated by reference in its entirety.

In an example of an implementation of a method 900 comprising such detection functionality, a TD/TDM may be inserted within a patient's body at 905. At step 910, a radiation source may be activated to emit light or another form of electromagnetic radiation to be used in detecting an organ or tissue. In some implementations, step 910 may further comprise directing the radiation towards an organ or tissue to be identified. At step 915, reflected light from the radiation source may be received and analyzed. As discussed above, in some implementations, such analysis may comprise a spectral analysis, such as using a polarized multi-spectral light scattering/scanning system. At step 920, location data, such as from an antenna, may be received. In some implementations, such location data may be combined with data obtained from analysis of the reflected radiation. Thus, at step 925, information may be provided to a user that may comprise location data and organ/tissue identification data. For example, as discussed above, in some implementations step 925 may comprise providing information to a surgeon regarding what organ/tissue has been identified and a current distance from the identified organ/tissue.

Figure 10:
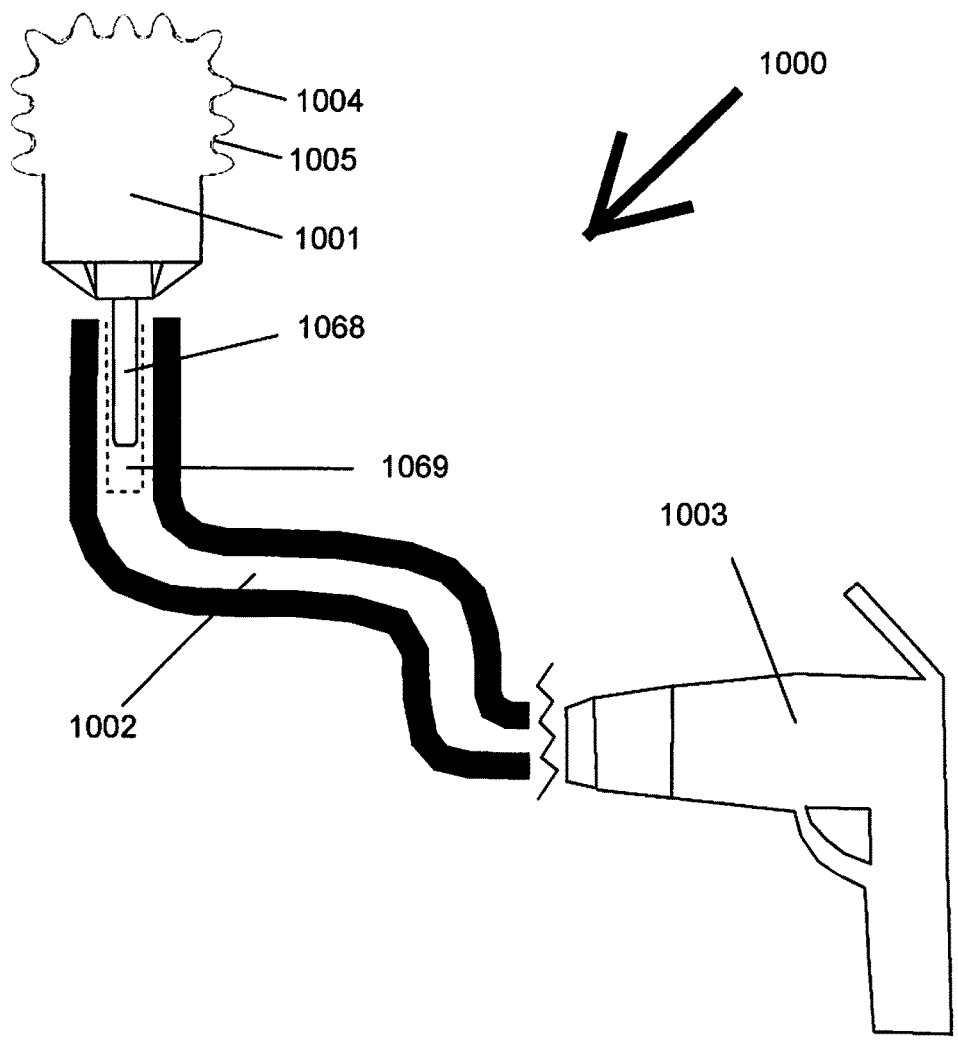
FIG. 10 depicts an embodiment comprising a modular, removable tip and a flexible shaft.

FIG. 10 depicts an embodiment of a modular TD 1000 comprising a tip 1001, a flexible shaft 1002, and an endoscope handle 1003. Tip 1001 is modular in that it is removable from flexible shaft 1002. More particularly, tip 1001 comprises a means for removably coupling the tip with a shaft at 1068. In the depicted embodiment, this coupling means comprises a tip plug 1068. In some embodiments, tip plug 1068 may be threaded to facilitate a secure coupling between modular tip 1001 and shaft 1002. However, in other embodiments, the coupling means may comprise a recess configured to receive a plug formed on the shaft. In still other embodiments, the coupling means may comprise a snap-fit coupling, a friction fit coupling, a bayonet clip, etc.

In the depicted embodiment, tip plug 1068 is configured to be received within a corresponding recess 1069 formed within shaft 1002. In some embodiments, tip plug 1068 may be configured to electrically couple tip 1001 with shaft 1002. In this manner, in embodiments comprising, for example, lysing segments, electricity from a power source may be transmitted through the coupling between plug 1068 and recess 1069 to allow for energizing the lysing segments. Other embodiments may be configured to transfer additional electricity, data, or materials through such coupling. For example, in embodiments comprising one or more sensors on tip 1001, a signal from such sensor(s) may be transmitted through shaft 1002 by way of the coupling means 1068.

In some embodiments, tip 1001 may be disposable as well, such that a surgeon can place an appropriate tip on the shaft and remove and dispose of the tip after surgery. Alternatively or additionally, a plurality of different tips may be provided, each of which may be disposable, or may be configured for sterilization and re-use, and an appropriate tip may be selected as needed for a particular surgery.

In the depicted embodiment, tip 1001 comprises a plurality of protrusions 1004, some of which are non-axial, and a plurality of recessions 1005 positioned therebetween, as described above. In some embodiments a tip comprising only axial protrusions may be swapped for tip 1001 as desired to suit a particular surgical procedure.

Figure 11:
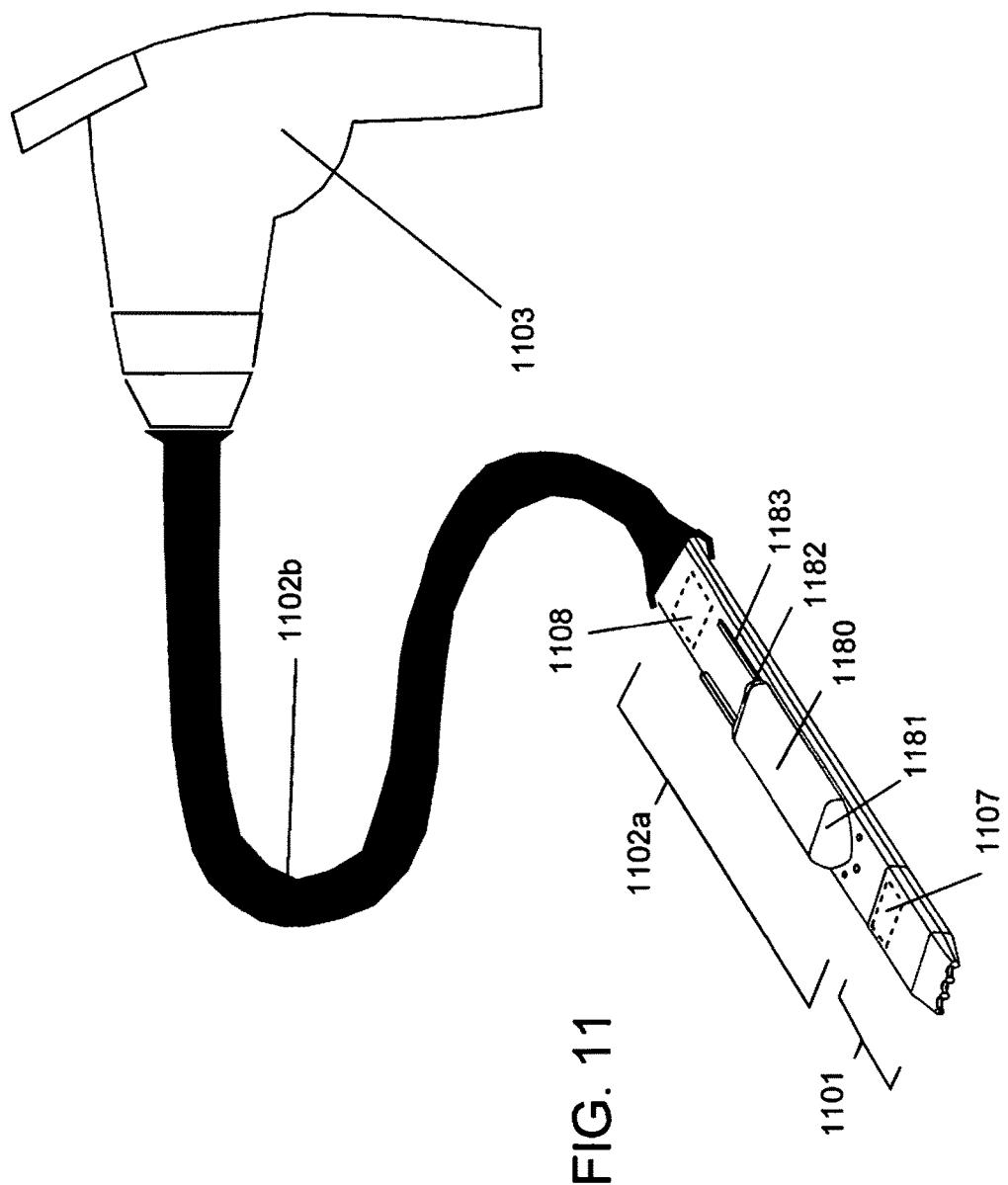
FIG. 11 depicts an embodiment comprising a shaft having a flexible segment and a rigid segment.

FIG. 11 depicts an alternative embodiment of a TD 1100 comprising a tip 1101 and an endoscope handle 1103. TD 1100 comprises a shaft comprising a rigid segment 1102a and a flexible segment 1102b.

The embodiment of FIG. 11 further comprises a biosensor dock 1184. In the embodiment of FIG. 11, dock 1184 is positioned along rigid segment 1102a of shaft 1102. Dock 1184 also comprises a cover 1180 that is selectively movable via means for selectively moving a cover 1183 which may be positioned adjacent dock 1184. Examples of such cover moving means may include rails, grooves, tracks, ratchets, cables, arms, lines, etc. In the depicted embodiment the cover moving means comprises a rail. In some embodiments a portion of the shaft may comprise cover moving means 1183. It is contemplated that in alternative embodiments, cover moving means 1183 may be omitted. Cover 1180 comprises a rear end 1182 and a pointed front end 1181. Rigid segment 1102a further comprises a second energy window 1108. Similarly, an energy window, such as first energy window 1107, may be positioned on the modular tip 1101. Biosensor dock 1184 may further comprise any of the features and components of any of the other docks described in connection with other embodiments presented herein, including fluid delivery ports, fluid extraction ports, sensors, seats, heaters, mixing elements, etc. In contemplated embodiments, first energy window 1107 and/or second energy window 1108 may be omitted. As with the embodiment of FIG. 10, the embodiment of FIG. 11 may comprise a modular and/or disposable tip 1101, such that a surgeon can place an appropriate tip on the shaft and remove and dispose of the tip after surgery. Alternatively or additionally, a plurality of different tips may be provided, each of which may be disposable, or may be configured for sterilization and re-use, and an appropriate tip may be selected as needed for a particular surgery. In the embodiment of FIG. 11, tip 1101 may be removably attached to rigid shaft segment 1102a to provide for such functionality.

It will be understood by those having skill in the art that changes may be made to the details of the above-described embodiments without departing from the underlying principles presented herein. For example, any suitable combination of various embodiments, or the features thereof, is contemplated.

Any methods disclosed herein comprise one or more steps or actions for performing the described method. The method steps and/or actions may be interchanged with one another. In other words, unless a specific order of steps or actions is required for proper operation of the embodiment, the order and/or use of specific steps and/or actions may be modified.

Throughout this specification, any reference to "one embodiment," "an embodiment," or "the embodiment" means that a particular feature, structure, or characteristic described in connection with that embodiment is included in at least one embodiment. Thus, the quoted phrases, or variations thereof, as recited throughout this specification are not necessarily all referring to the same embodiment.

Similarly, it should be appreciated that in the above description of embodiments, various features are sometimes grouped together in a single embodiment, figure, or description thereof for the purpose of streamlining the disclosure. This method of disclosure, however, is not to be interpreted as reflecting an intention that any claim require more features than those expressly recited in that claim. Rather, inventive aspects lie in a combination of fewer than all features of any single foregoing disclosed embodiment. It will be apparent to those having skill in the art that changes may be made to the details of the above-described embodiments without departing from the underlying principles set forth herein.

Furthermore, the described features, components, structures, steps, or characteristics may be combined in any suitable manner in one or more alternative embodiments and/or implementations. In other words, any of the features, components, structures, steps, or characteristics disclosed in any one disclosed embodiment may be combined with features, components, structures, steps, or characteristics of other disclosed embodiments.

The invention claimed is:

1. A surgical tool for biological tissue analysis and delivery of electrosurgical energy, comprising:
a shaft;
a tip positioned at a distal end of the shaft;
a biosensor dock positioned on the tool, wherein the biosensor dock is configured to sample at least one of biological tissue and biological fluid from a patient during a surgical procedure;
a biosensor positioned in the biosensor dock, wherein the biosensor is configured to provide information relating to the at least one of biological tissue and biological fluid within a patient during an electrosurgical procedure;
a biosensor seat, wherein the biosensor seat is configured to hold the biosensor, and wherein the biosensor seat is configured to allow the biosensor to be tilted relative to the biosensor dock; and
an actuator configured to move the biosensor seat.

2. The surgical tool of claim 1, wherein the biosensor dock is positioned on the shaft.

3. The surgical tool of claim 2, wherein the biosensor dock is positioned on an upper surface of the shaft.

4. The surgical tool of claim 1, further comprising a biosensor dock cover configured to cover the biosensor.

5. The surgical tool of claim 4, wherein the cover is selectively movable relative to the biosensor.

6. The surgical tool of claim 5, further comprising cover moving means for selectively moving the cover relative to the biosensor.

7. The surgical tool of claim 6, wherein the cover moving means comprises at least one of a rail, groove, track, ratchet, and cable.

8. The surgical tool of claim 4, wherein the cover is configured to seal an interior space defined at least in part by the biosensor dock while in a closed position.

9. The surgical tool of claim 4, wherein the cover comprises a portion of the shaft.

10. The surgical tool of claim 9, wherein the biosensor dock is encased within the shaft while in a closed position, and wherein a first portion of the shaft is movable relative to a second portion of the shaft to expose the biosensor dock in an open position.

11. The surgical tool of claim 4, wherein the cover comprises at least one groove configured to direct fluid flow within the biosensor dock.

12. The surgical tool of claim 4, wherein the cover comprises at least one projection configured to direct fluid flow within the biosensor dock.

13. The surgical tool of claim 4, wherein the cover comprises at least one opening positioned therein.

14. The surgical tool of claim 13, further comprising a vacuum port positioned within the biosensor dock, wherein the cover is configured to define an interior space such that a vacuum applied via the vacuum port results in suction through the at least one opening.

15. The surgical tool of claim 13, wherein the biosensor is configured such that at least a portion of the biosensor extends through the at least one opening.

16. The surgical tool of claim 15, wherein the biosensor is configured such that the at least a portion of the biosensor is selectively positionable through the at least one opening.

17. The surgical tool of claim 16, wherein the biosensor seat is configured to selectively raise the biosensor to selectively position the at least a portion of the biosensor through the at least one opening.

18. The surgical tool of claim 15, wherein the at least a portion of the biosensor comprises a fiber optic element.

19. The surgical tool of claim 4, further comprising an electromagnetic delivery element positioned within the biosensor dock.

20. The surgical tool of claim 19, wherein the cover comprises an interior surface configured to reflect electromagnetic radiation from the electromagnetic delivery element.

21. The surgical tool of claim 20, wherein the interior surface is mirrored.

22. The surgical tool of claim 1, wherein the biosensor seat is configured to releasably hold the biosensor.

23. The surgical tool of claim 1, wherein the biosensor seat is configured to seal at least a portion of the biosensor.

24. The surgical tool of claim 23, wherein the biosensor seat comprises a skirt configured to seal a perimeter of the biosensor.

25. The surgical tool of claim 23, wherein the biosensor seat comprises an opening comprising a self-sealing material.

26. The surgical tool of claim 1, wherein the biosensor comprises at least one of a nanobiosensor, a biological microarray, an optical biosensor, an electrochemical biosensor, and a piezoelectric biosensor.

27. The surgical tool of claim 26, wherein the biosensor comprises at least one of a DNA biosensor and a DNA microarray.

28. The surgical tool of claim 1, further comprising an antenna positioned on the surgical tool and configured to provide location data regarding a location of at least a portion of the surgical tool during an operation.

29. The surgical tool of claim 28, wherein the antenna comprises a radiofrequency identification tag.

30. The surgical tool of claim 1, wherein the tip comprises a plurality of protrusions and at least one recessed region positioned between at least a subset of the adjacent protrusions.

31. The surgical tool of claim 30, wherein the at least one recessed region comprises a lysing segment.

32. The surgical tool of claim 30, wherein each of the plurality of protrusions is oriented to extend along an axis of the shaft.

33. The surgical tool of claim 1, further comprising a fluid delivery port for delivering a fluid therethrough.

34. The surgical tool of claim 33, wherein the fluid delivery port is positioned within the biosensor dock for delivering a fluid into the biosensor dock.

35. The surgical tool of claim 33, further comprising a vacuum port for extracting fluid therethrough.

36. The surgical tool of claim 35, wherein the vacuum port is positioned within the biosensor dock for extracting fluid from the biosensor dock.

37. The surgical tool of claim 1, further comprising a temperature modification means for modifying a temperature within the biosensor dock.

38. The surgical tool of claim 37, wherein the temperature modification means comprises a heater.

39. The surgical tool of claim 1, further comprising a mixing element positioned within the biosensor dock.

40. The surgical tool of claim 1, further comprising an energy window, wherein the energy window is configured to deliver energy to tissue adjacent to the surgical tool during a surgical procedure.

41. The surgical tool of claim 40, wherein the energy window is positioned on the shaft outside of the biosensor dock.

42. The surgical tool of claim 41, wherein the energy window comprises an ultrasonic energy window.

43. The surgical tool of claim 40, wherein the energy window comprises a radiofrequency energy window.

44. The surgical tool of claim 42, wherein the ultrasonic energy window is configured to allow for selective adjustment of at least one of the power and frequency of the ultrasound energy delivered by the ultrasonic energy window.

45. The surgical tool of claim 1, further comprising a vibration means for vibrating the surgical tool during a surgical procedure.

46. The surgical tool of claim 45, wherein the vibration means comprises at least one of a piezoelectric actuator, an ultrasonic motor, and a vibration motor.

47. The surgical tool of claim 45, further comprising a handle, wherein the shaft is positioned at a distal end of the handle, and wherein the vibration means is positioned on or in the handle.

48. The surgical tool of claim 1, wherein the biosensor dock comprises at least one groove configured to direct fluid flow within the biosensor dock.

49. The surgical tool of claim 1, wherein the biosensor dock comprises at least one projection configured to direct fluid flow within the biosensor dock.

50. The surgical tool of claim 1, wherein the biosensor seat is positioned on an external surface of the shaft such that the biosensor seat is configured to allow for direct contact between the biosensor and the at least one of biological tissue and biological fluid during the electrosurgical procedure.

\* \* \* \* \*